(12) United States Patent
Crews

(10) Patent No.: US 11,123,284 B2
(45) Date of Patent: *Sep. 21, 2021

(54) METHOD OF TREATING DISEASE

(71) Applicant: Thomas M Crews, Statesboro, GA (US)

(72) Inventor: Thomas M Crews, Statesboro, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/978,742

(22) Filed: May 14, 2018

(65) Prior Publication Data

US 2018/0360745 A1   Dec. 20, 2018

Related U.S. Application Data

(63) Continuation-in-part of application No. 14/931,581, filed on Nov. 3, 2015, now Pat. No. 9,968,589, which is a continuation-in-part of application No. PCT/US2014/036855, filed on May 5, 2014, application No. 15/978,742, filed on May 14, 2018, which is a continuation-in-part of application No. 14/270,238, filed on May 5, 2014.

(60) Provisional application No. 61/819,023, filed on May 3, 2013.

(51) Int. Cl.
| | |
|---|---|
| A61K 9/00 | (2006.01) |
| A61K 45/06 | (2006.01) |
| A61K 9/08 | (2006.01) |
| A61K 31/439 | (2006.01) |
| A61K 31/245 | (2006.01) |
| A61K 31/4152 | (2006.01) |
| A61K 31/167 | (2006.01) |
| A61P 11/06 | (2006.01) |
| A61P 3/04 | (2006.01) |
| A61P 1/00 | (2006.01) |
| A61P 11/00 | (2006.01) |
| A61P 29/00 | (2006.01) |
| A61P 1/04 | (2006.01) |
| A61K 31/047 | (2006.01) |
| A61K 31/137 | (2006.01) |
| A61K 31/445 | (2006.01) |
| A61K 31/47 | (2006.01) |

(52) U.S. Cl.
CPC ............. *A61K 9/0046* (2013.01); *A61K 9/08* (2013.01); *A61K 31/047* (2013.01); *A61K 31/137* (2013.01); *A61K 31/167* (2013.01); *A61K 31/245* (2013.01); *A61K 31/4152* (2013.01); *A61K 31/439* (2013.01); *A61K 31/445* (2013.01); *A61K 31/47* (2013.01); *A61K 45/06* (2013.01); *A61P 1/00* (2018.01); *A61P 1/04* (2018.01); *A61P 3/04* (2018.01); *A61P 11/00* (2018.01); *A61P 11/06* (2018.01); *A61P 29/00* (2018.01)

(58) Field of Classification Search
CPC .................................................. A61K 9/0046
USPC .......................................................... 514/407
See application file for complete search history.

(56) References Cited

U.S. PATENT DOCUMENTS

| | | | |
|---|---|---|---|
| 6,093,417 A | 7/2000 | Petrus | |
| 6,465,442 B2 | 10/2002 | El Khoury | |
| 2008/0288016 A1 | 11/2008 | Amurthur et al. | |
| 2012/0252720 A1 | 10/2012 | Eilat | |

FOREIGN PATENT DOCUMENTS

WO   2013/040352   3/2013

OTHER PUBLICATIONS

Alejandro Hoberman et al.; Efficacy of Auralgan for Treating Ear Pain in Children With Acute Otitis Media; Arch. Pediatr. Adolesc. Med. 1997, 151, 675-678; Jul. 1997.
Bausch and Lomb Florida, Drugs.com (Sep. 30, 1990), pp. 1-5.
Butz N, Ossent, P and Homberger FR. Pathogenesis of guinea pig adenovirus infection. Lab Anim Sci 49(6):600-604, 1999.
ClinicalTrials.gov, Identifier NCT02153541; "Assessing the Efficacy of CREWS01 to Decrease Usage of Rescue Inhalers in Moderate to Sever Asthmatic Adults"; May 21, 2014.
Crean, Neurological Complications of Local Anaesthetic in Dentistry, Dental Update Oct. 1999, pp. 344-349.
Daniel N. Wood et al.; Clinical trials assessing ototopical agents in the treatment of pain associated with acute otitis media in children; Int. J. Pediatr. Otorhinol. 76 (2012) 1229-1235.
Drug Discontinuation: Benzocaine and Antipyrine (Auralgan) Otic Drops emailed to Seton Med-Staff Oct. 26, 2015.
Yagi M, Magal E, Sheng Z, Ang KA and Raphael Y. Hair cell protection from aminoglycoside ototoxicity by adenovirus-mediated overexpression of GDNF. Human Gene Therapy, 10:813-823, 1999.
Extended European Search Report, EP14791131.7, dated Dec. 8, 2016.
Food and Drug Administration: Good Laboratory Practice for Nonclinical Laboratory Studies. Code of Federal Regulations, Title 21, Part 58.
Food and Drug Administration: Use Only Approved Prescription Ear Drops; Consumer Updates; www.fda.gov; updated: Jul. 10, 2015.
International Search Report, PCT/US2014/036855 dated Oct. 7, 2014.
International Search Report, PCT/US2016/060085 dated Dec. 8, 2016.

(Continued)

*Primary Examiner* — Taofiq A Solola
(74) *Attorney, Agent, or Firm* — Baker Donelson

(57) ABSTRACT

The present disclosure relates to methods for treating a variety of diseases and/or ameliorating pain by administering to the ear canal of a subject a composition.

3 Claims, 20 Drawing Sheets

(10 of 20 Drawing Sheet(s) Filed in Color)

(56) References Cited

OTHER PUBLICATIONS

Jewett DL and Willistow JS. Auditory evoked far fields averaged from the scalp of humans. Brain 94:681-696, 1971.
Le Prell CG, Yagi M, Kawamoto K, Beyer LA, Atkin G, Raphael Y, Dolan DF and Bledsoe SC Jr, Moody DB. Chronic excitotoxicity in the guinea pig cochlea induces temporary functional deficits without disrupting optoacoustic emissions. J Acoust Soc AM 116(2): 1044-56, 2004.
Mayo Clinic; Vagus Nerve Stimulation Overview.
Orozco CR, Niparko JK, Richardson BC, Dolan DF, Ptok MU and Altschuler RA. Experimental model of immune-mediated hearing loss using cross-species immunization. Laryngoscope 100:941-947, 1990.
Schweitzer VG, Rarey KE, Dolan DF, Abrams G, Litterst CJ and Sheridan C. Ototoxicity of cisplatin vs. platinum analogs CBDCA (JM-8) and CHIP (JM-9). Otolaryngol Head Neck Surg 94:458-470, 1986.
Smith (Med. Chronicle, Mar. 1889, p. 1).
Yamasoba T, and Dolan DF. Chronic strychnine administration into the cochlea potentiates permanent threshold shift following noise exposure. Hear Res 112:13-20, 1997.
Written Opinion, PCT/US2014/036855 dated Oct. 7, 2014.
Written Opinion, PCT/US2016/060085 dated Dec. 8, 2016.
"About Preeclampsia and Eclampsia", NICHD-Eunice Kennedy Shriver National Institute of Child Health and Human Development; date last updated—Nov. 19, 2018.

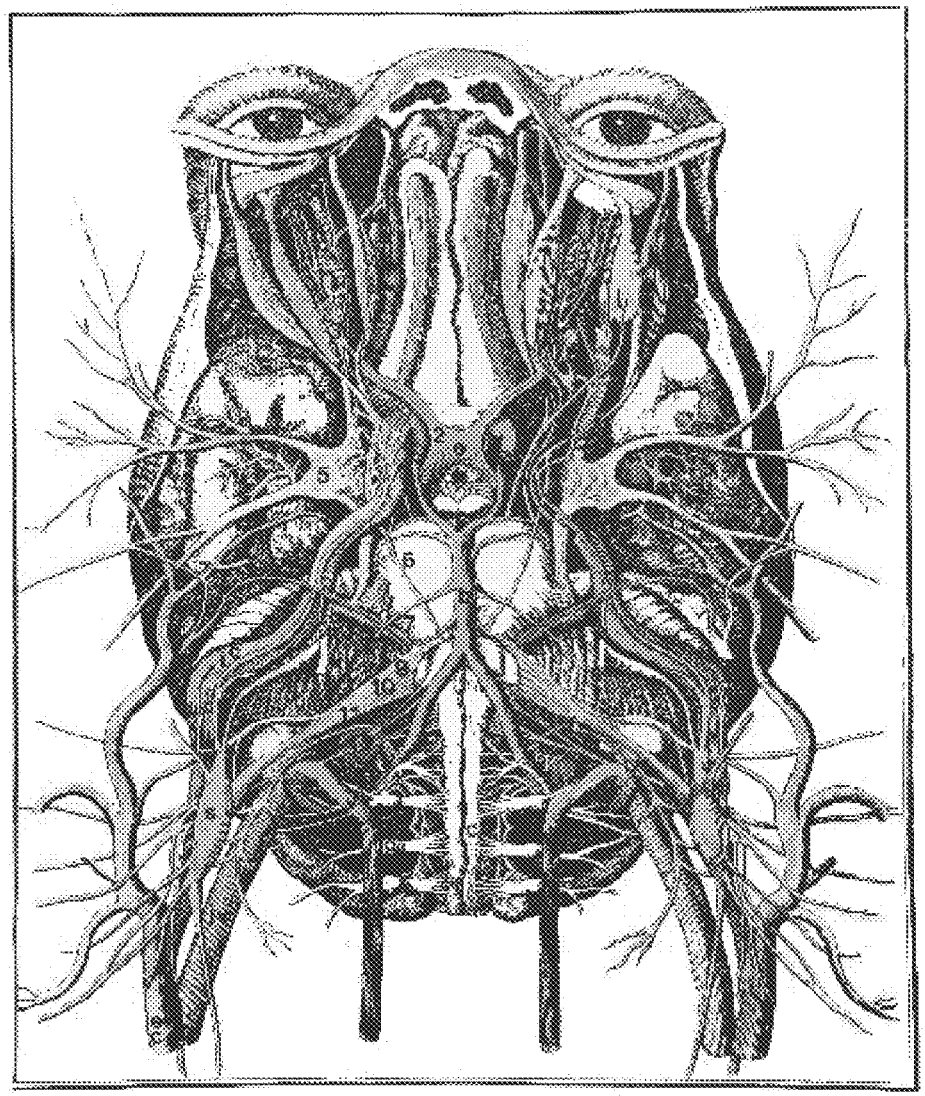
*FIG. 18 - CONT.*

METHOD OF TREATING DISEASE

This application is a continuation-in-part of U.S. patent application Ser. No. 14/931,581, which is a continuation-in-part of International Application No. PCT/US2014/036855, filed May 5, 2014, which claims priority to U.S. Provisional Application Ser. No. 61/819,023, filed May 3, 2013; and this application is also a continuation-in-part of U.S. patent application Ser. No. 14/270,238, filed on May 5, 2014, which claims benefit and priority to U.S. Provisional Application Ser. 61/819,023, filed on May 3, 2013, the contents of each of which are hereby incorporated by reference in their entireties. The specification, figures and complete disclosure of U.S. Provisional Application No. 61/819,023, PCT/US2014/036855, U.S. patent application Ser. No. 14/270,238 and U.S. patent application Ser. No. 14/931,581 are incorporated herein by specific reference for all purposes.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

The present disclosure relates to methods for treating a variety of diseases and/or ameliorating pain by administering to the ear canal of a subject a composition.

BACKGROUND OF THE INVENTION

Sympathetic presynaptic nerve cell bodies are located in the lateral horn of spinal cord segments T1-L2. Sympathetic postsynaptic cell bodies are in ganglia, either sympathetic chain ganglia or prevertebral ganglia. Sympathetic presynaptic fibers get to the sympathetic chain via white rami communicantes and either synapse at the level they enter, ascend or descend to synapse, or leave the sympathetic trunk without synapsing as a splanchnic nerve to go to a prevertebral ganglion. Sympathetic postsynaptic fibers may enter the spinal nerves via gray rami communicantes to be distributed with dorsal and ventral primary rami, may form perivascular plexuses to be distributed with blood vessels, or may travel to the target organ directly. The sympathetic nervous system provides sympathetic innervation to essentially every part of the body.

Parasympathetic presynaptic cell bodies are located in the brainstem and the lateral horns of spinal cord segments S2, S3, and S4 and leave the CNS in cranial nerves III, VII, IX and X, and in pelvic splanchnic nerves arising from the ventral primary rami of spinal nerves S2, S3, and S4. The parasympathetic postsynaptic cell bodies are located in four pairs of ganglia in the head (associated with cranial nerves III, VII and IX), and otherwise in microscopic ganglia either on or in the wall of the target organ. The distribution of the parasympathetic nervous system is more limited than the sympathetic nervous system, with cranial nerves III, VII and IX supplying smooth muscle and glands of the head, the vagus nerve supplying the visceral organs up to the left colic flexure, and the pelvic splanchnics supplying the descending and sigmoid colon, rectum and pelvic viscera. With the exception of the external genitalia, the parasympathetic nervous system does not reach the body wall.

The autonomic nervous system allows vertebrate species to go about their daily business without having to think about the mechanics of their organs. Hearts beat, intestines digest, blood vessels change diameter, and vertebrates adapt appropriately to any situation, all without our having to think about it.

SUMMARY OF THE INVENTION

The invention provides for methods for treating a variety of diseases that comprises performing topical auricular anesthesia of the external auditory canal for the purposes of anesthetizing cranial nerves 5, 7, 9, 10, 11, and 12, along with the parasympathetic nervous system, the sympathetic nervous system. In one embodiment, the invention provides for auricular anesthesia of the autonomic nervous system. In one embodiment, auricular anesthesia is performed on the trigeminal nerve, facial nerve, glossopharyngeal nerve, vagus nerve, accessory nerve, hypoglossal nerves, or a combination thereof. The invention further provides for modulation of the general somatic nervous system and the general visceral nervous system by administering an otic pharmaceutical composition comprising one or more anesthetics (such as lidocaine and/or tetracaine) in solution with a pharmaceutical carrier (such as an excipient) glycerine, and with or without epinephrine. In some embodiments, the otic pharmaceutical composition further comprises an analgesic, such as a pyrazolone derivative. In some embodiments, the pyrazolone derivative is antipyrene. The invention provides methods for treating a variety of diseases that comprises performing auricular anesthesia of the sympathetic nervous system via the vagus nerve to the sympathetic plexus. The invention also provides methods for treating pain from any variety of diseases disclosed herein by performing auricular anesthesia of the vagus nerve directly and the sympathetic nerve indirectly thus blocking general somatic afferent signals and general visceral afferent signals. The invention further provides methods of blocking pain from a variety of diseases that comprises performing auricular anesthesia of the vagus nerve with resultant anesthesia to the thalamic nuclei resulting in modulation of general visceral afferent pain and general somatic afferent pain. In various embodiments, the disease is a neurology-psychiatry-related affliction, an ear-nose-throat (ENT)-related affliction, a GU-related affliction, a gastrointestinal (GI)-related affliction, a cardiac-related affliction, a pulmonary-related affliction, or a metabolic-related affliction.

In various embodiments, the present invention provides a safe and non-invasive procedure, by which to treat a host of human diseases, and their symptoms, that are associated with the fifth cranial nerve (trigeminal nerve), the seventh cranial nerve (facial nerve), ninth cranial nerve (glossopharyngeal nerve), and the tenth cranial nerve (vagus nerve). The present disclosure provides a method of disrupting the normal physiological function of the nerve that does not rely upon an invasive and costly surgical procedure. The disclosed methods are able to "block" the transduction of both afferent and efferent signals from being transmitted via the trigeminal, facial, glossopharyngeal or vagus nerves. Such blockage of the transduction of signals on the nerve is achieved by a topical auricular anesthesia procedure, whereby a pharmaceutical composition is administered to the ear canal of a subject. It is the cutaneous auricular anesthesia of those nerves and their particular close proximity and relationship to their respective ganglia that allows for their modulation in function. It is that modulation of function which results in the modulation of expression of specific disease processes.

In an embodiment, the present disclosure provides a method for treating symptoms of a disease, which comprises topically administering to an ear canal of a subject a pharmaceutical composition, comprising: (i) an analgesic and (ii) an anesthetic. In an embodiment, the analgesic is at least one pyrazolone derivative selected from the group consisting of ampyrone, dipyrone, antipyrine, aminopyrine, and propyphenazone. In a preferred embodiment, the analgesic is antipyrine. In an embodiment, the anesthetic is at least one selected from the group consisting benzocaine, chloroprocaine, cocaine, cyclomethycaine, dimethocaine, larocaine, piperocaine, propoxycaine, procaine, novocaine, proparacaine, tetracaine, amethocaine, articaine, bupivacaine, cinchocaine, dibucaine, etidocaine, levobupivacaine, lidocaine, lignocaine, mepivacaine, prilocaine, ropivacaine, trimecaine, and pharmaceutically acceptable derivatives thereof. In a preferred embodiment, the anesthetic is benzocaine.

An aspect of the invention provides for an otic pharmaceutical composition, comprising: (i) at least one analgesic comprising a pyrazolone derivative. In other aspects of the invention, the otic pharmaceutical composition further comprises (ii) at least one anesthetic comprising Formula I:

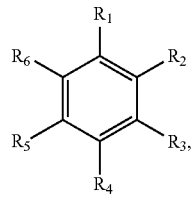

wherein $R_1$ comprises:

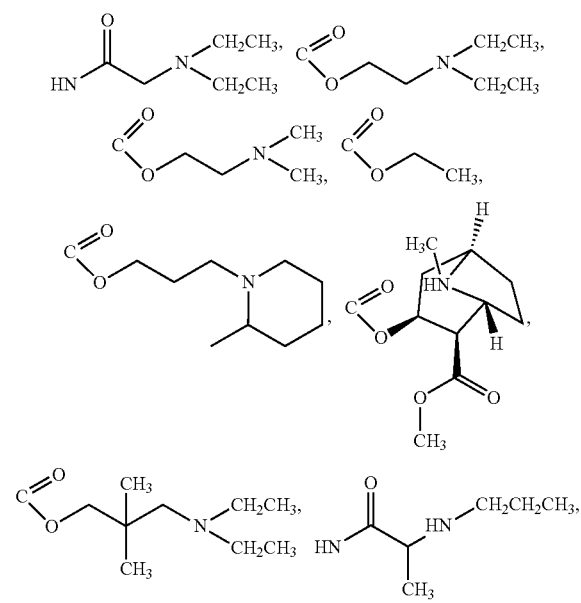

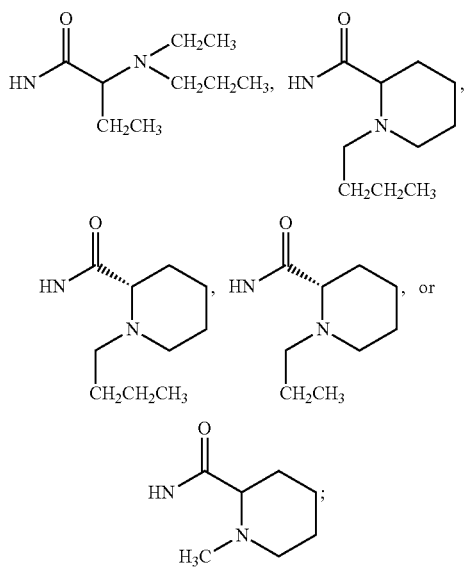

wherein $R_2$ comprises H, $CH_3$, Cl, or

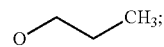

wherein $R_3$ comprises H or $NH_2$; wherein $R_4$ comprises H, $NH_2$, $CH_3$,

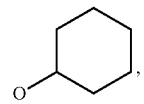

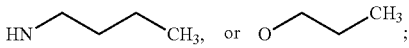

wherein $R_5$ comprises H; and wherein $R_6$ comprises H or $CH_3$. An aspect of the invention further provides an otic pharmaceutical composition comprising at least 2 anesthetic compounds having Formula I as described herein. For example, the otic pharmaceutical composition can comprise the anesthetics tetracaine

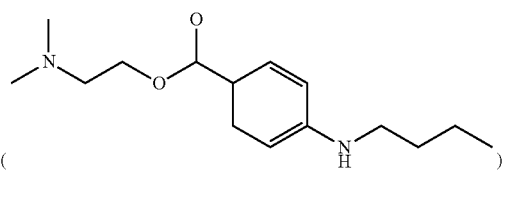 [SMILES: CCCCNC1=CCC(C(O)OCCN(C)C)C=C1]

and lidocaine

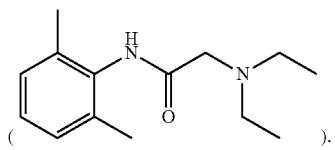 [SMILES: CCN(CC)CC(=O)Nc1c(C)cccc1C]

An aspect of the invention provides for a method for treating or ameliorating symptoms in a subject with a disease associated with a particular cranial nerve, wherein the disease is a neurology-psychiatry-related affliction, an ear-nose-throat (ENT)-related affliction, a GU-related affliction, a gastrointestinal (GI)-related affliction, a cardiac-related affliction, a pulmonary-related affliction, or a metabolic-related affliction, the method comprising administering to an ear canal of a subject in need of such treatment an effective amount of a pharmaceutical composition, comprising: (i) at least one analgesic comprising a pyrazolone derivative, and/or (ii) at least one anesthetic comprising Formula I, and wherein said pharmaceutical composition is administered to the ear canal of the subject in a concentration sufficient to physiologically alter the activity of the subject's particular cranial nerve compared to the physiological activity of that particular cranial nerve in a subject not administered the pharmaceutical composition.

An aspect of the invention a method for treating or ameliorating symptoms in a subject with a disease associated with a particular cranial nerve, wherein the disease is a neurology-psychiatry-related affliction, an ear-nose-throat (ENT)-related affliction, a GU-related affliction, a gastrointestinal (GI)-related affliction, a cardiac-related affliction, a pulmonary-related affliction, or a metabolic-related affliction, the method comprising administering to an ear canal of a subject in need of such treatment an effective amount of an otic pharmaceutical composition, wherein the pharmaceutical composition comprises at least 2 anesthetic compounds having Formula I as described herein. For example, the otic pharmaceutical composition can comprise the anesthetics tetracaine

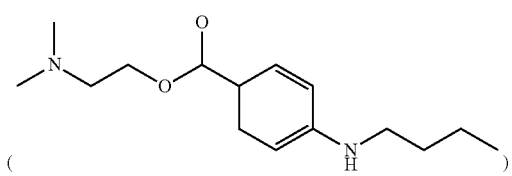 [SMILES: CCCCNC1=CCC(C(O)OCCN(C)C)C=C1]

and lidocaine

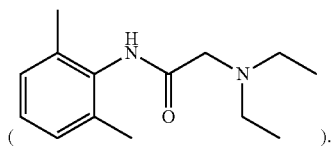 [SMILES: CCN(CC)CC(=O)Nc1c(C)cccc1C]

In one embodiment, $R_1$ of Formula I comprises

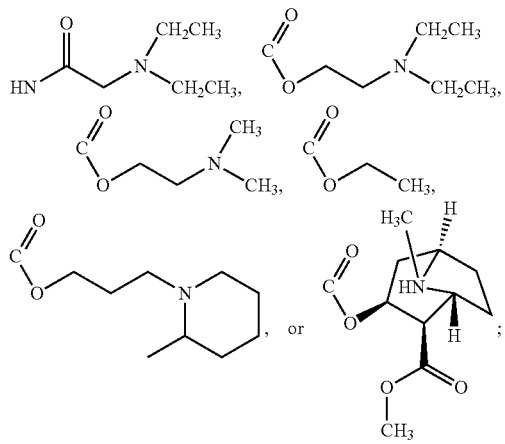

wherein $R_2$ comprises H or $CH_3$; wherein $R_3$ comprises H; wherein $R_4$ comprises H, $NH_2$,

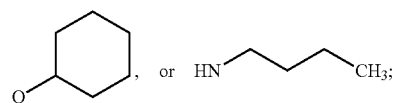 [SMILES: OC1CCCCC1 ; CCCCN]

wherein $R_5$ comprises H; and wherein $R_6$ comprises H or $CH_3$. In one embodiment, $R_1$ of Formula I comprises

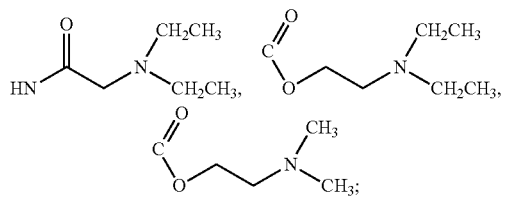

wherein $R_2$ comprises H or $CH_3$; wherein $R_3$ comprises H; wherein $R_4$ comprises H, $NH_2$, or

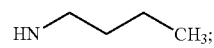

wherein $R_5$ comprises H; and wherein $R_6$ comprises H or $CH_3$.

In one embodiment, the analgesic is at least one pyrazolone derivative selected from the group consisting of ampyrone, dipyrone, antipyrine, aminopyrine, and propyphenazone. In a preferred embodiment, the analgesic is antipyrine. In one embodiment, the anesthetic comprises benzocaine

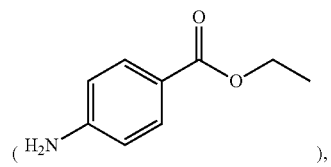

chloroprocaine
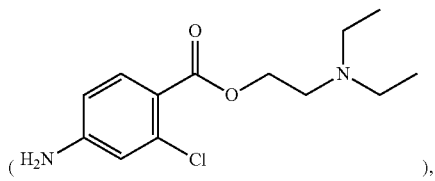 [SMILES: CCN(CC)CCOC(=O)c1ccc(N)cc1Cl]
cocaine
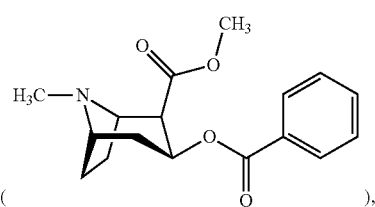
cyclomethycaine
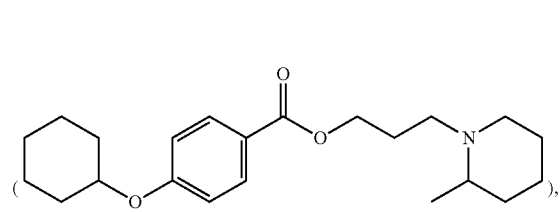 [SMILES: CC1CCCCN1CCCOC(=O)c1ccc(OC2CCCCC2)cc1]
dimethocaine
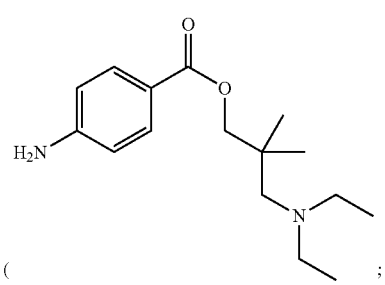 [SMILES: CCN(CC)CC(C)(C)COC(=O)c1ccc(N)cc1]
also referred to as larocaine), piperocaine
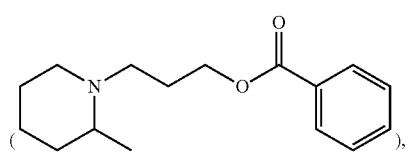 [SMILES: CC1CCCCN1CCCOC(=O)c1ccccc1]
propoxycaine
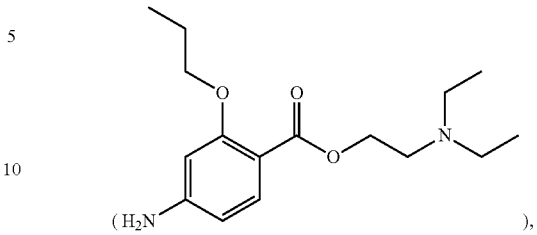
procaine
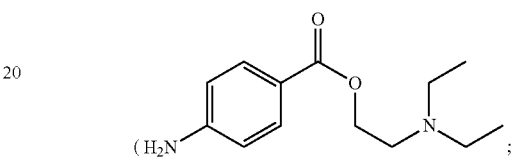
also referred to as novocaine), proparacaine
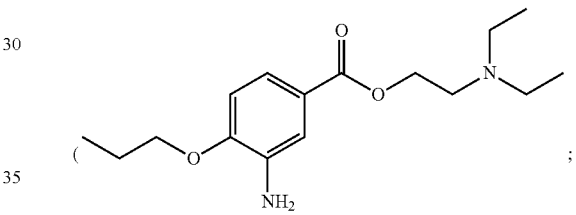
also referred to as proxymetacaine), tetracaine
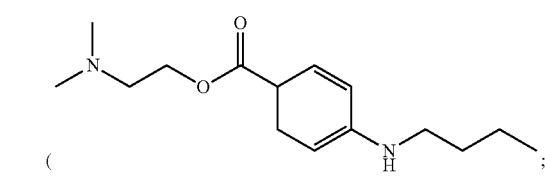 [SMILES: CCCCNC1=CCC(C(=O)OCCN(C)C)C=C1]
also referred to as amethocaine), articaine
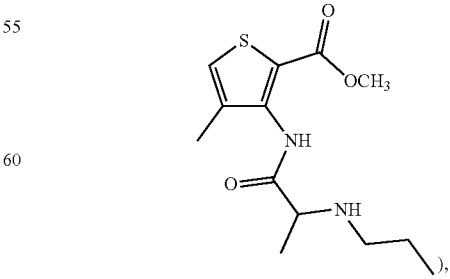

bupivacaine

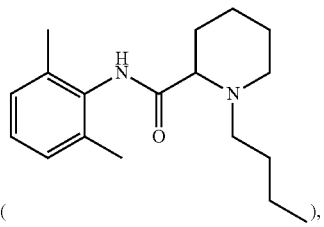 [SMILES: CCCCN1CCCCC1C(=O)Nc1c(C)cccc1C]

cinchocaine

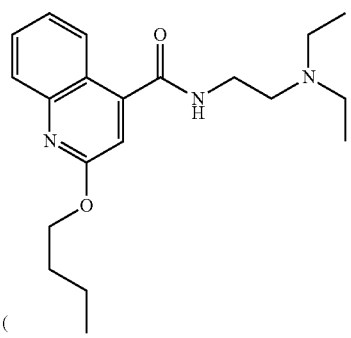

also referred to as dibucaine),
etidocaine

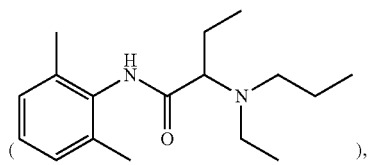 [SMILES: CCCN(CC)C(CC)C(=O)Nc1c(C)cccc1C]

levobupivacaine

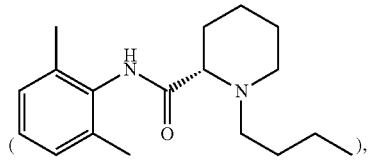 [SMILES: CCCCN1CCCC[C@H]1C(=O)Nc1c(C)cccc1C]

lidocaine

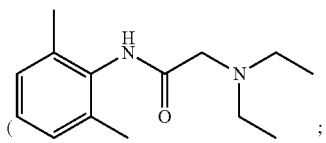 [SMILES: CCN(CC)CC(=O)Nc1c(C)cccc1C]

also referred to as lignocaine and xylocaine), mepivacaine

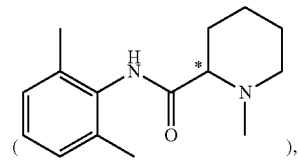 [SMILES: Cc1cccc(C)c1NC(=O)C1CCCCN1C]

prilocaine

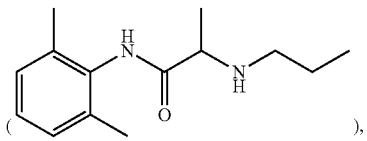 [SMILES: CCCNC(C)C(=O)Nc1c(C)cccc1C]

ropivacaine

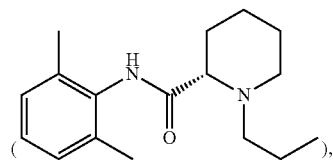 [SMILES: CCCN1CCCC[C@H]1C(=O)Nc1c(C)cccc1C]

farmocaine

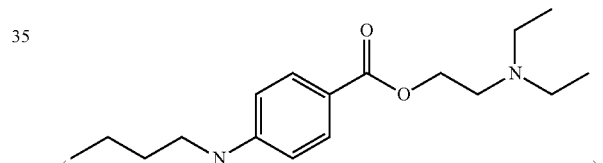

trimecaine

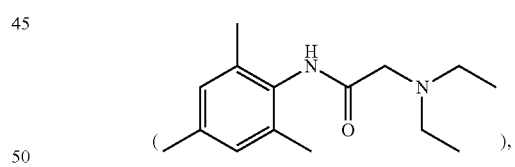

bupivacaine, marcaine, a combination of the anesthetics listed herein, or pharmaceutically acceptable derivatives thereof. In another embodiment, the anesthetic is not benzocaine. In one embodiment, the anesthetic is lidocaine. In one embodiment, the anesthetic is tetracaine. In one embodiment, the anesthetic is tetracaine and lidocaine. In one embodiment, the anesthetic is lidocaine and bupivacaine.

In one embodiment, the invention is directed to a method for treating or ameliorating symptoms in a subject with a disease associated with a particular cranial nerve where auricular anesthesia is performed on the trigeminal nerve (cranial nerve 5), the facial nerve (cranial nerve 7), the glossopharyngeal nerve (cranial nerve 9), the vagus nerve (cranial nerve 10), the spinal accessory nerve (cranial nerve 11), the hypoglossal nerve (cranial nerve 12), or a combination thereof.

The diseases that are treatable by the disclosed methodology are numerous and described herein. Any disease that is associated with an organ or bodily tissue that is innervated by the particular nerve could potentially be treated by the present methods. Particular mention of the following diseases treatable by the present methods is made: asthma, neurogenic cough, globus hystericus, spasmodic dysphonia, gastroesophageal reflux disease, and obesity. The present methods are also suitable for treating post-tonsillectomy or post-adenoidectomy pharyngeal pain, or oropharyngeal pain.

In one embodiment, the disease is a neurology-psychiatry-related affliction, an ear-nose-throat (ENT)-related affliction, a GU-related affliction, a gastrointestinal (GI)-related affliction, a cardiac-related affliction, a pulmonary-related affliction, a metabolic-related affliction, an infection-related affliction, a skin-related affliction, a cell proliferation-related affliction, and/or a blood flow-related affliction.

In one embodiment, the neurology-psychiatry-related affliction is at least one selected from the group consisting of: chronic fatigue syndrome, fibromyalgia, epilepsy, Obsessive Compulsive Disorder, panic attack, Post-Traumatic Stress Disorder, Tourette's Syndrome, Focal Dystonia, Tic Doloreaux, Bulimia, Anxiety, Depression, Restless Leg Syndrome, Dysautonomia, Familial Intentional Tremor, Migraine pain, Autism Spectrum Disorder, Anxiety Headache, sleeplessness, Reticular Activating System (RAS) dysregulation, Multiple Sclerosis, Peripheral Neuropathy, Apraxia, Neck and Shoulder Pain, Parkinson's Disease, General Somatic Afferent Pain, General Visceral, Afferent Pain, opiate withdrawal, Dysarthria, ADHD, Nonspecific hand tremor, Stuttering, cerebral palsy, Raynaud's Phenomenon, and excessive sweating, reflex sympathetic dystrophy, sensory processing disorder, and decreased libido. In one embodiment, the General Somatic Afferent Pain comprises Neuromuscular Pain of the neck, back, arms, legs, or shoulders; Joint Pain; Sciatica pain; Arthritis pain; Shingles Pain; Reflex Sympathetic Dystrophy pain; or a combination thereof. In one embodiment, a symptom of opiate withdrawal comprises Generalized Pain, Muscle Aches, Nausea, vomiting, Sweating, Diarrhea, or a combination thereof.

In one embodiment, the ear-nose-throat (ENT)-related affliction is at least one selected from the group consisting of: Palatal Myoclonus, Post Tonsillectomy Pain, Pharyngeal Pain, Laryngeal Pain, Neurogenic Cough, Globus Hystericus, Spasmodic Dysphonia, Snoring, Allergic Rhinitis, Chronic Sinusitis, Chronic Nasal Congestion, Allergic Conjunctivitis, Sneezing, Hiccups, Rhinitis, Tinnitus, Dysphagia, ear pain, neck pain, Dry Eye Syndrome, Trigeminal Neuralgia pain, and Temporomandibular Joint Pain.

In one embodiment, the Gastroenterology/Urology (GU)-related affliction is at least one selected from the group consisting of: bladder spasm, dysmenorrhea, pelvic pain, Premature Labor, interstitial cystitis, Prostatitis, Eclampsia, pre-eclampsia, HELLP (hemolysis, elevated liver enzymes, and low platelets) Syndrome, cystitis, Kidney Pain, enuresis, dysuria, dyspareunia, encopresis, heavy flow menstruation, frequent urination, Prolonged Vaginal Bleeding, decreased renal blood flow, and chronic renal failure.

In one embodiment, the gastrointestinal (GI)-related affliction is at least one selected from the group consisting of: irritable bowel syndrome (IBS), ulcerative colitis, acid reflux, Gastritis, Gastroenteritis, Hyperemesis Gravidarum, Pediatric Colic, Hepato-Renal Syndrome, Appetite Suppression, Gall Bladder Pain, Chronic constipation, Chronic diarrhea, and Pancreatitis.

In one embodiment, the cardiac-related affliction is at least one selected from the group consisting of: Paroxysmal (Lone) (Vagal) Atrial Fibrillation, Orthostatic (Neurogenic) Hypotension, Reflex Asystolic Syncope, Postural Orthostatic Tachycardia Syndrome (POTS), Vasovagal Reflex, cardiac surgery derived cough, heart block, Atrial Contractions, Tachycardia, Congestive Heart Failure, premature atrial contraction, and atrial tachycardia.

In one embodiment, the pulmonary-related affliction is at least one selected from the group consisting of: asthma, chronic obstructive pulmonary disease (COPD), bronchitis, cystic fibrosis, and Bronchospasm.

In one embodiment, the metabolic-related affliction is at least one selected from the group consisting of: hypertension, diabetes, septic shock, neurogenic shock, hyperglycemia, hypercholesteremia, and insulin resistance.

In one embodiment, the infection-related affliction is at least one selected from the group consisting of: Herpes Simplex 1 infection, Herpes, Simplex 2 infection, and Varicella Zoster infection.

In one embodiment, the skin-related affliction is at least one selected from the group consisting of: facial flushing, facial blushing, alopecia areata, atopic dermatitis, chronic eczema, acne vulgaris, oily skin, rosacea, and morgellons disease.

In one embodiment, the cell proliferation-related affliction is at least one selected from the group consisting of: cancer and mastocytosis.

In one embodiment, the blood flow-related affliction is at least one selected from the group consisting of erectile dysfunction, open wound healing, and sickle cell disease.

In yet other embodiments, the diseases treatable by the disclosed methodology include, but are not limited to: cardiac diseases, paroxysmal (lone) (vagal) atrial fibrillation, reflex systolic syncope, postural orthostatic tachycardia syndrome (POTS), excessive gag reflex, esophageal dysphagia, vomiting, nausea, odynophagia, esophageal pain, esophageal neuralgia, gastritis, dyspepsia, gall bladder disease, colecistitis pain, abdominal pain, esophageal motility disorder or esophageal dysmotility, spastic colon, pancreatic pain or spasms, pediatric colic, rectal spasms and pain, bladder spasm (overactive bladder), interstitial cystitis, dysmenorrhea, premature labor, pelvic pain, chronic pelvic pain, chronic prostatitis pain, eclampsia, preeclampsia, HELLP syndrome, cystitis pain, irritable bowel syndrome, Cohn's disease, ulcerative colitis, reflux disease, gastritis, gastroenteritis symptoms, hyperemesis gravidarum, pediatric colic, hepato-renal syndrome, appetite suppression, gall bladder pain, inflammation of the esophagus, inflammation of the stomach, inflammation of the colon, kidney pain (from stone, infection, or tumor), enuresis, dysuria, dyspareunia, encopresis, heavy flow periods, frequent urination, prolonged vaginal bleeding, inhibit erections, prevention of premature ejaculation, inhibit excessive sweating, ureteral spasms, menstrual cramps, uterine spasms, ovarian pain and spasms, fallopian tube pain and spasms, pediatric asthma, adult asthma, chronic obstructive pulmonary disease (COPD), bronchial mucus, acute bronchitis, asthmatic bronchitis, chronic bronchitis, bronchospasm, cystic fibrosis, inflammation of the lung, emphysema, pleuritic chest pain, intercostal muscle pain, nerve pain, bronchospasm secondary to intubation and extubation, angina pectoris, cardiac vagal blockage, vasovagal reflex blockage, bradycardia, hypotension, orthostatic hypotension, hypertension, diabetes, shock, septic shock, reduction of blood sugar, inflammation of the pancreas, syncope secondary to vagal or cardiac reasons, vasovagal syncope, bradyarrhythmias, vasodilation of the skin, neuralgia, laryngospasm, acute laryngitis, laryngeal pain, chronic laryngitis, post extubation and intubation laryngospasms, palatal myoclonus, post-tonsillectomy pain, snoring, allergic rhinitis, vasomotor rhinitis, inflammatory polyposis (nasal), chronic sinusitis, chronic nasal congestion, allergic conjunctivitis, sneezing, hiccups, rhinitis, tinnitus, dysphagia, croup, chronic fatigue syndrome, fibromyalgia (chronic), epilepsy, obsessive compulsive disorder, panic attacks, post-traumatic stress disorder, Tourette's syndrome, focal dystonia, tic doloreaux, bulimia, anxiety, depression, restless leg syndrome, dysautonomia, familial intentional tremor, migraines, autism spectrum, anxiety headaches, insomnia or sleep disorders, multiple sclerosis, modulation of the reticular activating system, peripheral neuropathy, apraxia, neck and shoulder pain, and Parkinson's disease.

Thus, the present method applies generally to the treatment of any disease, ailment, or bodily condition that may benefit from the "blockage" of the particular nerve function. That is, any condition that would benefit from the hampered ability of the nerve to transmit neurological signals are encompassed by the disclosed method.

In methods disclosed herein, the pharmaceutical composition is administered to the ear canal of a subject in a concentration sufficient to physiologically alter the activity of the subject's nerve compared to the physiological activity of a nerve in a subject not administered the pharmaceutical composition. Thus, the present pharmaceutical composition utilized in a method as disclosed, is able to disrupt the natural ability of the nerve to transmit neurological signals along its length. These signals, both afferent and efferent, are blocked or hampered by the present methods.

The amount of analgesic present in the pharmaceutical composition comprises from about: 1 to 100 mg per mL, 10 to 100 mg per mL, 20 to 100 mg per mL, 30 to 100 mg per mL, 40 to 100 mg per mL, 50 to 100 mg per mL, 60 to 100 mg per mL, 70 to 100 mg per mL, 80 to 100 mg per mL, 90 to 100 mg per mL, or 100 mg per mL. In some embodiments, the amount of analgesic present is from about 50 to 60 mg per mL, or about 54 mg per mL, or about 50 to 55 mg per mL, or about 55 to 60 mg per mL.

The amount of anesthetic present in the pharmaceutical composition comprises from about: 1 to 100 mg per mL, 10 to 100 mg per mL, 20 to 100 mg per mL, 30 to 100 mg per mL, 40 to 100 mg per mL, 50 to 100 mg per mL, 60 to 100 mg per mL, 70 to 100 mg per mL, 80 to 100 mg per mL, 90 to 100 mg per mL, or 100 mg per mL. In some embodiments, the amount of anesthetic present is from about 1 to 20 mg per mL, or about 1 to 15 mg per mL, or about 5 to 15 mg per mL, or about 10 to 20 mg per mL, or about 10 to 15 mg per mL, or about 14 mg per mL.

The total amount of the pharmaceutical composition administered to a patient during one dosage may comprise from about: 0.001 to 0.01 mL of solution, or 0.01 to 0.1 mL of solution, or 0.1 to 0.5 mL of solution, or 0.1 to 1 mL of solution, or 1 to 1.5 mL of solution, or 1.5 to 2 mL of solution, or 2 to 5 mL of solution, or 5 to 10 mL of solution. The administration may comprise using a "dropper" bottle that applies "drops" of solution to the patients ear canal during a typical dosage. Such administration may comprise 1 mL 15-20 drops, 0.5 mL 10 drops, 0.25 mL 5 drops.

The pharmaceutical composition can comprise at least one anesthetic, at least one analgesic, or any combination thereof. For example, the composition can comprise one anesthetic, such as lidocaine; two anesthetics, such as lidocaine and bupivacaine; or an anesthetic and an analgesic, such as benzocaine and antipyrine.

The pharmaceutical composition can be provided in a solution comprising 1%, 2%, 3%, 4%, 5%, 6%, 7%, 8%, 9%, 10%, 20%, 30%, 40%, 50%, 60%, 70%, 80%, 90%, or 95% of one or more anesthetics. In one example, the composition comprises 4% lidocaine and 2% bupivacaine.

As used herein, unless otherwise expressly specified, all numbers such as those expressing values, ranges, amounts, or percentages may be read as if prefaced by the word "about," even if the term does not expressly appear. Any numerical range recited herein is intended to include all sub-ranges subsumed therein. Plural encompasses singular and vice versa; e.g., the singular forms "a," "an," and "the" include plural referents unless expressly and unequivocally limited to one referent.

In certain embodiments, the subject treated by the present methods does not have an ear infection. Furthermore, in certain embodiments, the subject treated by the present methods does not have an ear ache or is not experiencing ear pain.

In particular aspects, the present method is utilized on patients with ear infections. That is the present methods in certain embodiments specifically are utilized on patients with an external ear canal infection, with otalgia or with a middle ear infection, associated with or without purulence. Certain embodiments specifically utilize the methods on subjects experience an ear ache or ear pain. In these embodiments, a first step of method may comprise an ear examination by a treating physician to assure a patient does have an ear infection or is experiencing ear pain, or has a hole in the eardrum. It may consist of redness, middle ear effusion or swelling of the tissues of the external canal or distortion of the ear drum. In some aspects after ascertaining that the patient does indeed have an ear infection, whether it is in the ear drum, ear canal or middle ear, topical anesthesia in the form of Antipyrene/benzocaine dissolved in an excipient may be inserted in the ear canal in the form of an eardrop to reduce ear pain. This may also be done with lidocaine and tetracaine in a similar excipient of glycerine, with or without the presence of epinephrine. What is contraindicated is the usage of any topical anesthetic in the ear canal in the presence of an ear tube or pressure equalization tube or an active on going perforation.

The disclosed pharmaceutical compositions utilized in the present methods may comprise additional components such as: antibiotics, vasoconstrictors, glycerin, and acetic acid.

The pharmaceutical compositions may comprise any pharmaceutically acceptable carrier, or adjuvant, and may be formulated as: solutions, foams, gels, creams, pastes, lotions, emulsions, and combinations of the aforementioned.

The pharmaceutical composition may be administered once a day, twice a day, three times a day, four times a day, five times a day, six times a day, seven times a day, eight times a day, nine times a day, 10 to 20 times a day, or up to continuously throughout the day as needed. Further, in certain embodiments, the pharmaceutical composition is administered upon the onset of an asthma attack. In other embodiments, the pharmaceutical composition is administered upon a person feeling hungry. Some aspects of the methods entail administration of the pharmaceutical composition upon a patient feeling pain in their pharyngeal region. Certain embodiments contemplate not utilizing the taught compositions on patients that are experiencing ear pain, or that have an ear infection, or swelling in the ear associated with an ear infection. In these embodiments, the disclosed method of treating diseases associated with the vagus nerve may be immediately halted or stopped upon a patient developing ear pain.

A specifically preferred ailment to be treated by the disclosed method is the pharyngeal or oropharyngeal pain associated with a post-operative tonsillectomy or a post-operative adenoidectomy. These embodiments treat pain that patients feel after the aforementioned surgical procedures. In these embodiments, the pharmaceutical composition is applied to the ear canal of a subject that has had a tonsillectomy or adenoidectomy within: the preceding 168 hours (or 7 days), preceding 48 hours, preceding 24 hours, preceding 12 hours, preceding 4 hours, or immediately post-operation, prior to administering the pharmaceutical composition. Thus, the present method contemplates doctors prescribing the disclosed procedure and pharmaceutical composition to patients to utilize immediately upon feeling pain in the pharyngeal or oropharyngeal regions post-surgery.

Another particularly preferred ailment, or disease, to be treated by the disclosed method is asthma. In certain embodiments, acute asthma attacks are treated by the present methods. These embodiments involve administering the pharmaceutical composition to the ear canal of a subject that is presently experiencing an acute asthma attack. Further, these embodiments may comprise treatment of a subject that has experienced an asthma attack in the last 48, 24, 12, 6, or 1 hours. Thus, the methods taught herein may be used in conjunction with normal bronchodilators and corticosteroids for the treatment and management of a patient's asthma. The methods may be suitable for use on asthma patients experiencing a peak expiratory flow rate (PEFR) of 50 to 79% of the patient's normal peak flow readings, i.e. "the yellow zone" as classified by the American Lung Association. The methods are also suitable for use on a patient experiencing a peak expiratory flow rate of less than 50% of the patient's normal peak flow reading, i.e. "the red zone." The methods can be utilized in conjunction with a rescue inhaler when a patient experiences a severe asthma attack. Consequently, in some embodiments, the present pharmaceutical composition is a component of a kit, wherein said kit comprises a rescue inhaler and a pharmaceutical composition comprising antipyrine and benzocaine. The kit is intended to be kept with a patient that is in danger of suffering a severe asthma attack. Further, in some embodiments, the pharmaceutical composition is part of an emergency first aid kit that is kept in school classrooms, for example. In these embodiments, teachers could utilize the present pharmaceutical composition in times of emergency, such as when a student suffers a severe asthma attack, but yet there is no rescue inhaler readily available.

The present methods are also suitable for use in treating chronic asthma. In these embodiments, patients utilize the disclosed compositions as taught in the present disclosure to prevent the onset of an acute asthma attack. In these methods, chronic asthma is managed by continuous use of the present methods. Thus, in certain embodiments, patients with asthma are administered the pharmaceutical compositions presented herein before the onset of an asthma attack. For example, certain embodiments of the present methods are effective at controlling asthma in patients that play sports. Often, patients suffering from asthma will experience a decreased ability to breathe upon physical exertion, which in some cases may lead to a severe asthma attack requiring the use of an inhaler. The present methods allow the treatment of a subject's ear canal with a pharmaceutical composition comprising antipyrine and benzocaine before the subject engages in playing a sport. In this manner, the present methods may be an effective therapy for patient's to utilize before engaging in physical activity, in order to reduce the likelihood of having an asthma attack.

Another particularly preferred condition, or disease, to be treated by the disclosed method is obesity. The present methods treat obesity by providing a mechanism to suppress a patient's appetite. By suppressing a patient's appetite, the present methods provide another tool for doctor's to utilize in managing a patient's weight. Thus, obesity may be treated by administering the taught pharmaceutical composition to a subject's ear canal. In some embodiments, subjects are treated with the taught pharmaceutical composition whenever the subjects experience a sensation of hunger. Further, some embodiments administer the disclosed pharmaceutical compositions to the subject's ear canal immediately before a meal is eaten, or 10 minutes to 60 minutes before a meal is eaten, or 20 to 60 minutes before a meal is eaten, or 30 to 60 minutes before a meal is eaten, or concurrently with the consumption of a food. Thus, in some aspects, the present method of auricular anesthesia of the vagus nerve is utilized on a patient within an hour prior to the patient eating any food. In this way, the patient's appetite is satiated and less food will be consumed. Further, some embodiments administer the disclosed pharmaceutical compositions to the subject's ear canal in the morning, preferably before the subject eats breakfast, thus providing an effective appetite suppressant that lasts until at least lunch.

In some embodiments, the present pharmaceutical compositions and treatment methodology are part of a comprehensive weight loss program that involves not only utilization of the pharmaceutical composition to curb a patient's appetite, but also may include a specific diet and exercise regime.

In some aspects, a person applying the topical pharmaceutical composition to a patient's ear canal should have good light, so as to get a superficial look into the patient's ear, so as to check for any gross obstructions, i.e. wax, skin, infection, purulence, or swelling. The person may gently pull the ear pinna outward and upward, so as to straighten out the ear canal. Ear drops comprising the taught pharmaceutical composition that have been previously warmed and are quite viscid should be applied to the posterior or back wall of the lateral ear opening. The drops should be applied very slowly and deliberately, one drop at a time, allowing for each drop to slowly migrate down the ear canal. The patient's head should be resting on its side on a flat soft surface for optimal application. The back wall of the canal and eardrum have a large portion of the vagal nerve fibers, and thus pointed application to this area is desired. In some aspects, children under 10 will require 4 to 8 drops per ear, while adults and children over 12 usually require 6 to 10 drops for anesthesia. In some embodiments, drops are always followed by a cotton ball in the lateral ear canal for about one hour to insure the maintenance of the medicine in the ear canal to provide the required topical anesthesia to the vagus nerve. After an hour the cotton may be removed.

The administration of a pharmaceutical composition to a patient's ear canal for the purpose of auricular anesthesia of the vagus nerve to treat a disease affected by vagus nerve physiological alteration is referred to in some embodiments as the "Crews Maneuver." The Crews Maneuver of utilizing the ear canal as a conduit to anesthetizing the vagus nerve does not suffer from the drawbacks present in the art.

Aspects further comprise methods for ameliorating pain in a subject by administering to an ear canal of the subject afflicted with a distal pain an effective amount of a pharmaceutical composition comprising at least one anesthetic comprising Formula I described herein. In embodiments, a distal pain comprises a non-ear pain. The composition can further comprises at least one analgesic comprising a pyrazolone derivative. Still further, the pharmaceutical composition can comprise one or more of an antibiotic, a vasoconstrictor, glycerin, epinephrine, or acetic acid. In some embodiments, 2 or more anesthetics comprising formula I can be administered to a subject in an effective amount of a pharmaceutical composition.

In embodiments, the anesthetic can comprises benzocaine, chloroprocaine, cocaine, cyclomethycaine, dimethocaine, larocaine, piperocaine, propoxycaine, procaine, novocaine, proparacaine, tetracaine, amethocaine, articaine, bupivacaine, cinchocaine, dibucaine, etidocaine, levobupivacaine, lidocaine, lignocaine, mepivacaine, prilocaine, ropivacaine, farmocaine, trimecaine, marcaine, bupivacaine, or a combination of the anesthetics listed herein.

In embodiments, the pyrazolone derivative is selected from the group consisting of ampyrone, dipyrone, antipyrine, aminopyrine, and propyphenazone.

In embodiments, the amount of anesthetic does not exceed 252 mg/day. In embodiments, the amount of analgesic administered does not exceed 972 mg/day.

In embodiments, the subject does not have an ear infection, ear pain, or a combination thereof.

Non-limiting examples of distal pain (i.e., non-ear pain) comprise post-tonsillectomy pharyngeal or oropharyngeal pain, post-adenoidectomy pharyngeal or oropharyngeal pain, laryngeal pain, migraine pain, anxiety headaches, peripheral neuropathy, neck and shoulder pain, general somatic afferent pain, neuromuscular pain, joint pain, sciatica pain, arthritis pain, shingles pain, reflex sympathetic dystrophy pain, general visceral afferent pain, post tonsillectomy pain, pharyngeal pain, laryngeal pain, neck pain, trigeminal neuralgia pain, temporomandibular joint pain, pelvic pain, chronic prostatitis pain, cystitis pain, kidney pain, gastritis pain, gall bladder pain, and pancreatitis pain.

Aspects are still further directed towards a method for treating a subject suffering from an affliction associated with a particular cranial nerve comprising administering to an ear canal of a subject an effective amount of a pharmaceutical composition comprising at least one anesthetic described herein. The composition can further comprises at least one analgesic comprising a pyrazolone derivative. Still further, the pharmaceutical composition can comprise one or more of an antibiotic, a vasoconstrictor, glycerin, epinephrine, or acetic acid.

In embodiments, the affliction comprises those described herein, such as a neurology-psychiatry-related affliction, ear-nose-throat (ENT)-related affliction, Gastroenterology/Urology (GU)-related affliction, gastrointestinal (GI)-related affliction, cardiac-related affliction, pulmonary-related affliction, metabolic-related affliction, infection-related affliction, skin-related affliction, cell proliferation-related affliction, or blood flow-related affliction.

These and other features, aspects, and advantages of embodiments of the present disclosure will become better understood with regard to the following description, claims, and accompanying drawings explained below.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
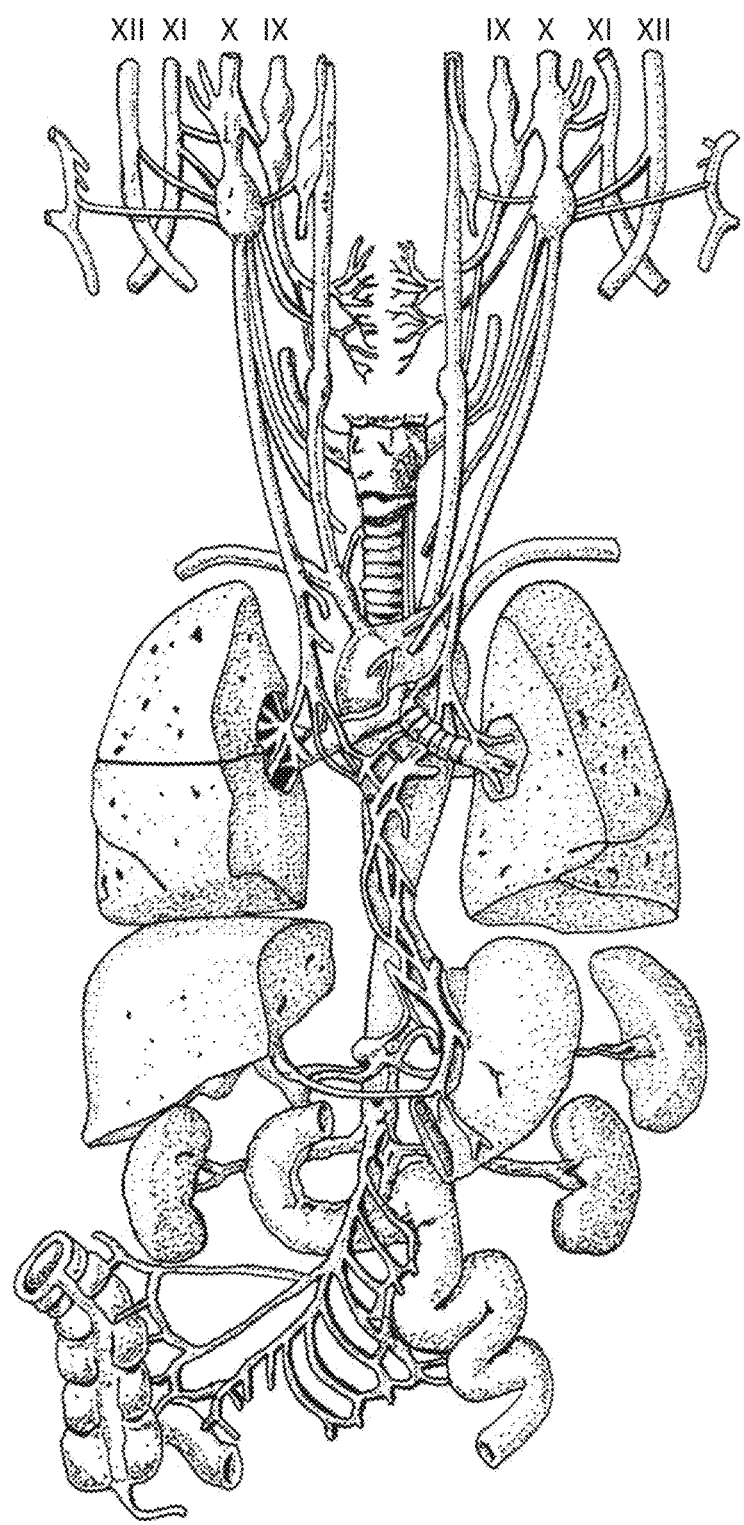
FIG. 1 is an illustration of the complex anatomy of the vagus nerve. The auricular branch is noted.

Detailed descriptions of one or more preferred embodiments are provided herein. It is to be understood, however, that the present disclosure may be embodied in various forms. Therefore, specific details disclosed herein are not to be interpreted as limiting, but rather as a basis for the claims and as a representative basis for teaching one skilled in the art to employ the present disclosure in any appropriate manner.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, for example, to reduce or ameliorate the severity and/or duration of an affliction or condition, or one or more symptoms thereof, prevent the advancement of conditions related to an affliction or condition, prevent the recurrence, development, or onset of one or more symptoms associated with an affliction or condition, or enhance or otherwise improve the prophylactic or therapeutic effect(s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease, a stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

The term "in need thereof" refers to the need for symptomatic or asymptomatic relief from a condition such as, for example, cancer or a neurodegenerative disease. The subject in need thereof may or may not be undergoing treatment for conditions related to, for example, cancer or a neurodegenerative disease.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in Remington: The Science and Practice of Pharmacy, 21$^{st}$ Edition (University of the Sciences in Philadelphia, ed., Lippincott Williams & Wilkins 2005); and Handbook of Pharmaceutical Excipients, 7$^{th}$ Edition (Raymond Rowe et al., ed., Pharmaceutical Press 2012); each hereby incorporated by reference in its entirety.

The terms "animal," "subject," and "patient" as used herein includes all members of the animal kingdom including, but not limited to, mammals, animals (e.g., cats, dogs, horses, swine, etc.) and humans.

Autonomic Nervous System.

The autonomic nervous system is divided into the sympathetic and parasympathetic components. The sympathetic nervous system prepares the body for stress and is called the "fight or flight" system. The parasympathetic system prepares the body for rest and is called the "rest and digest" or "vegetative" system.

The sympathetic nervous system is one of the two main divisions of the autonomic nervous system; the other being the parasympathetic nervous system. Sympathetic nervous system can be modulated or significantly affected by the usage of auricular anesthesia to the external auditory canal. Auricular anesthesia to the external auditory canal can modulate the vagus and glossopharyngeal nerves, which have direct connections to the sympathetic chain or nervous system (see FIG. 12, FIG. 13; see also FIG. 1 and FIG. 5). The primary process of the sympathetic nervous system is to stimulate the body's flight or fight response. It is however constantly active at a basic level to maintain homeostasis. It works as a compliment in intimate conjunction with the parasympathetic nervous system by direct neural communication.

There are two kinds of neurons involved in the transmission of any signal through the sympathetic nervous system: preganglionic or post-ganglionic. The shorter preganglionic neurons originate in the thoracolumbar region of the spinal cord (levels T1 to L2 specifically) to travel to a ganglion often one of the paravertebral ganglion where they synapse with a postganglionic neuron. From there, the long postganglionic neuron extends across most of the body. The sympathetic nerves arise from near the middle of the spinal cord in the intermediolateral nucleus of the lateral gray column, beginning at the first thoracic vertebrae of the vertebral column and are thought to extend to the second or third lumbar vertebrae. Axons of these nerves leave the spinal cord through the anterior root. They pass near the spinal sensory ganglion and they enter the anterior rami of the spinal nerves. However, unlike somatic innervation, they quickly separate out through white rami connectors that connect to either the paravertebral or the prevertebral ganglia extending alongside the spinal column. Presynaptic nerves or axons terminating either of the paravertebral ganglia or the prevertebral ganglia. In all cases, the axon enters the paravertebral ganglia at the level of its originating spinal nerve. After this it can either synapse in this ganglion, ascend to a more superior, or descend to a more inferior paravertebral ganglion and synapse there, or it can descend to a prevertebral ganglion and synapse there with the post-synaptic cell. Post-synaptic cell then goes on to innervate the target and effector, i.e. gland, smooth muscle, etc. Notable exceptions are the routes for innervation of the suprarenal adrenal medulla. In this case, the presynaptic neurons pass through the paravertebral ganglia onto through the prevertebral ganglia and then synapse directly with the suprarenal tissue. Auricular anesthesia to the vagus nerve can send signals to the paravertebral ganglia and affect neural transmission and thus affect sympathetic outflow to various organs, muscles, blood vessels, glands, skin, and nerves thus affecting disease processes.

The sympathetic nervous system is involved in hundreds of disease processes including the following: chronic fatigue syndrome, fibromyalgia, post-traumatic stress disorder, restless leg, anxiety, dysautonomia, hand tremors, migraine headaches, and muscle diseases such as multiple sclerosis, cerebral palsy, and Parkinson disease. Other diseases such as peripheral neuropathies, arthritis, reflex sympathetic dystrophy, muscle aches, sweating, orthostatic hypotension, postural orthostatic tachycardia syndrome, vasovagal reflex, cardiac arrhythmias, hypertension, diabetes, elevated blood sugar, elevated cholesterol, irritable bowel disease, irritable bowel syndrome, chronic constipation, ulcerative colitis, eclampsia, preeclampsia, HELLP syndrome, premature ejaculation, supraventricular tachycardia, and congestive heart failure can all be affected by an overactive sympathetic nervous system. Modulation of this system can be accomplished by directly modulating the parasympathetic nervous system via the auricular branch of the vagus nerve and the glossopharyngeal nerve and its intimate connections with the superior cervical sympathetic ganglion with its connections to the rest of the sympathetic nervous system, please see pending figures. It should also be noted that functions of the sympathetic nervous system also include dilation of pupils, increased in drying of the eyes, increased drying of the nose and the mouth, increasing the heart rate and force of contraction, dilation of bronchials, dilation of skeletal muscles, dilation of blood vessels going to the brain, decreasing blood flow to the kidney, decreasing blood flow to the gastrointestinal tract, increasing activation of sweat glands inhibiting peristalsis, increasing levels of renin, increasing levels of cholesterol and triglycerides, increasing levels of blood pressure, and promoting ignition for ejaculation.

The present invention provides for a method of treating or ameliorating symptoms in a subject with a disease associated with a particular cranial nerve, wherein the disease is a neurology-psychiatry-related affliction, an ear-nose-throat (ENT)-related affliction, a GU-related affliction, a gastrointestinal (GI)-related affliction, a cardiac-related affliction, a pulmonary-related affliction, or a metabolic-related affliction. In one embodiment, the disease is a neurology-psychiatry-related affliction, an ear-nose-throat (ENT)-related affliction, a GU-related affliction, a gastrointestinal (GI)-related affliction, a cardiac-related affliction, a pulmonary-related affliction, or a metabolic-related affliction. In one embodiment, the neurology-psychiatry-related affliction is at least one selected from the group consisting of: chronic fatigue syndrome, fibromyalgia, epilepsy, Obsessive Compulsive Disorder, panic attack, Post-Traumatic Stress Disorder, Tourette's Syndrome, Focal Dystonia, Tic Doloreaux, Bulimia, Anxiety, Depression, Restless Leg Syndrome, Dysautonomia, Familial Intentional Tremor, Migraine pain, Autism Spectrum Disorder, Anxiety Headache, sleeplessness, Reticular Activating System (RAS) dysregulation, Multiple Sclerosis, Peripheral Neuropathy, Apraxia, Neck and Shoulder Pain, Parkinson's Disease, General Somatic Afferent Pain, General Visceral, Afferent Pain, opiate withdrawal, Dysarthria, ADHD, Nonspecific hand tremor, Stuttering, cerebral palsy, Raynaud's Phenomenon, and excessive sweating. In one embodiment, the General Somatic Afferent Pain comprises Neuromuscular Pain of the neck, back, arms, legs, or shoulders; Joint Pain; Sciatica pain; Arthritis pain; Shingles Pain; Reflex Sympathetic Dystrophy pain; or a combination thereof. In one embodiment, a symptom of opiate withdrawal comprises Generalized Pain, Muscle Aches, Nausea, vomiting, Sweating, Diarrhea, or a combination thereof. In one embodiment, the ear-nose-throat (ENT)-related affliction is at least one selected from the group consisting of: Palatal Myoclonus, Post Tonsillectomy Pain, Pharyngeal Pain, Laryngeal Pain, Neurogenic Cough, Globus Hystericus, Spasmodic Dysphonia, Snoring, Allergic Rhinitis, Chronic Sinusitis, Chronic Nasal Congestion, Allergic Conjunctivitis, Sneezing, Hiccups, Rhinitis, Tinnitus, Dysphagia, ear pain, neck pain, Dry Eye Syndrome, Trigeminal Neuralgia pain, and Temporomandibular Joint Pain. In one embodiment, the Gastroenterology/Urology (GU)-related affliction is at least one selected from the group consisting of: bladder spasm, dysmenorrhea, pelvic pain, Premature Labor, interstitial cystitis, Prostatitis, Eclampsia, pre-eclampsia, HELLP Syndrome, cystitis, Kidney Pain, enuresis, dysuria, dyspareunia, encopresis, heavy flow menstruation, frequent urination, Prolonged Vaginal Bleeding, and decreased renal blood flow. In one embodiment, the gastrointestinal (GI)-related affliction is at least one selected from the group consisting of: irritable bowel syndrome (MS), ulcerative colitis, acid reflux, Gastritis, Gastroenteritis, Hyperemesis Gravidarum, Pediatric Colic, Hepato-Renal Syndrome, Appetite Suppression, Gall Bladder Pain, Chronic constipation, Chronic diarrhea, and Pancreatitis. In one embodiment, the cardiac-related affliction is at least one selected from the group consisting of: Paroxysmal (Lone) (Vagal) Atrial Fibrillation, Orthostatic (Neurogenic) Hypotension, Reflex Asystolic Syncope, Postural Orthostatic Tachycardia Syndrome (POTS), Vasovagal Reflex, cardiac surgery derived cough, heart block, Atrial Contractions, Tachycardia, and Congestive Heart Failure. In one embodiment, the pulmonary-related affliction is at least one selected from the group consisting of: asthma, chronic obstructive pulmonary disease (COPD), bronchitis, cystic fibrosis, and Bronchospasm. In one embodiment, the metabolic-related affliction is at least one selected from the group consisting of: hypertension, diabetes, septic shock, neurogenic shock, hyperglycemia, and hypercholesteremia.

General visceral and afferent fibers conduct sensory impulses usually pain and reflex sensations from the viscera, glands, and blood vessels to the central nervous system. They are considered to be part of the visceral nervous system not the autonomic nervous system. However, unlike the efferent fibers of the autonomic nervous system the afferent fibers are not classified as either sympathetic or parasympathetic. General visceral afferent create referred pain to activating general somatic afferent fibers where the two meet in the posterior horn of the spinal cord. The cranial nerves that contain general visceral afferent fibers include the facial nerve, the glossopharyngeal nerve, and the vagus nerve all of which innervate the external auditory canal. General visceral afferent referred pain can be modulated by auricular anesthesia to these cranial nerves as they provide sensory innervation to specific areas of the external auditory canal. Topical anesthesia to these areas can modulate general visceral afferent signals from the body back to the central nervous system.

Figure 12:
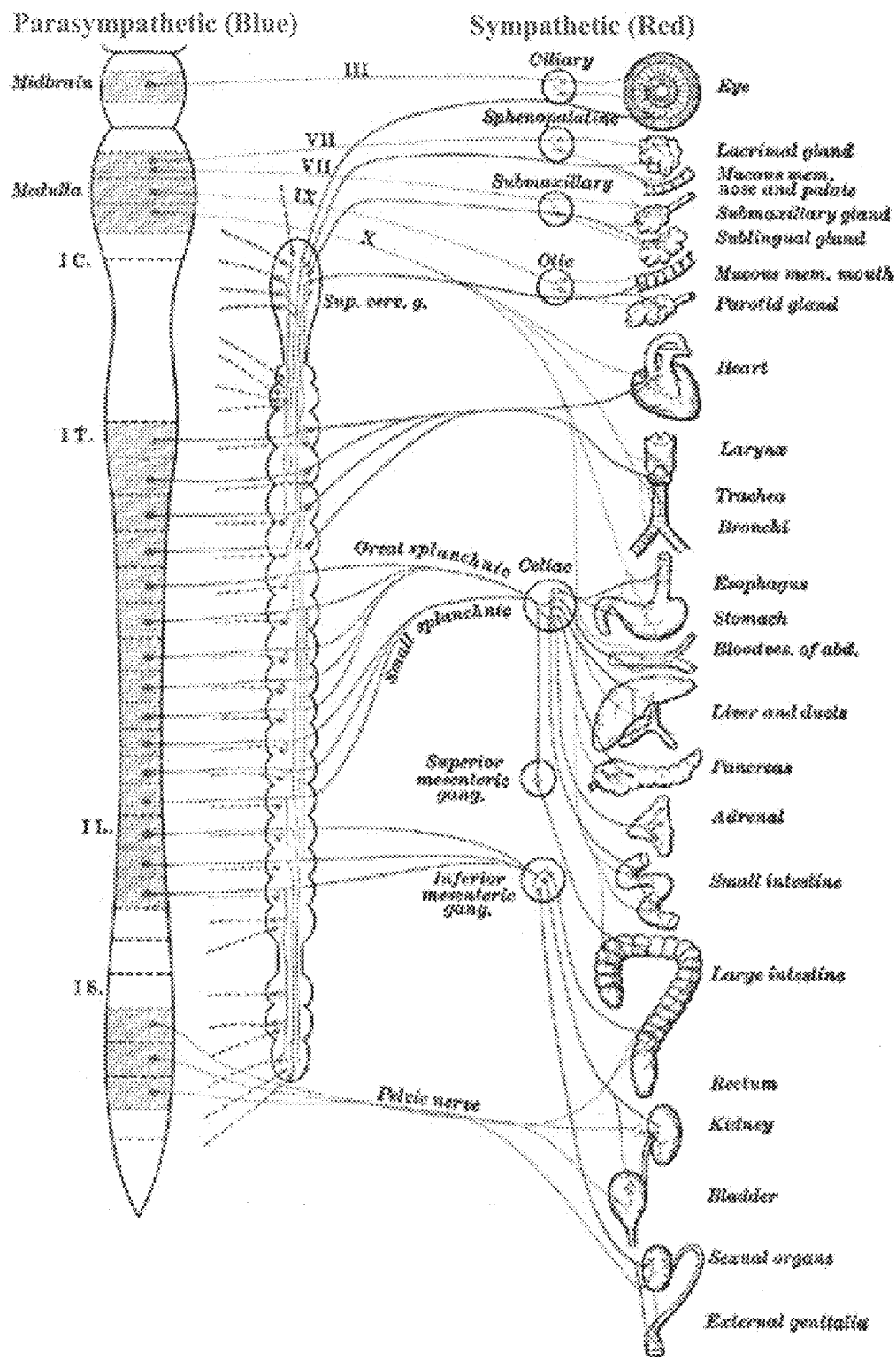
FIG. 12 is an illustration of the anatomy of nerve innervations of the sympathetic (red) and parasympathetic (blue) systems.
Figure 13:
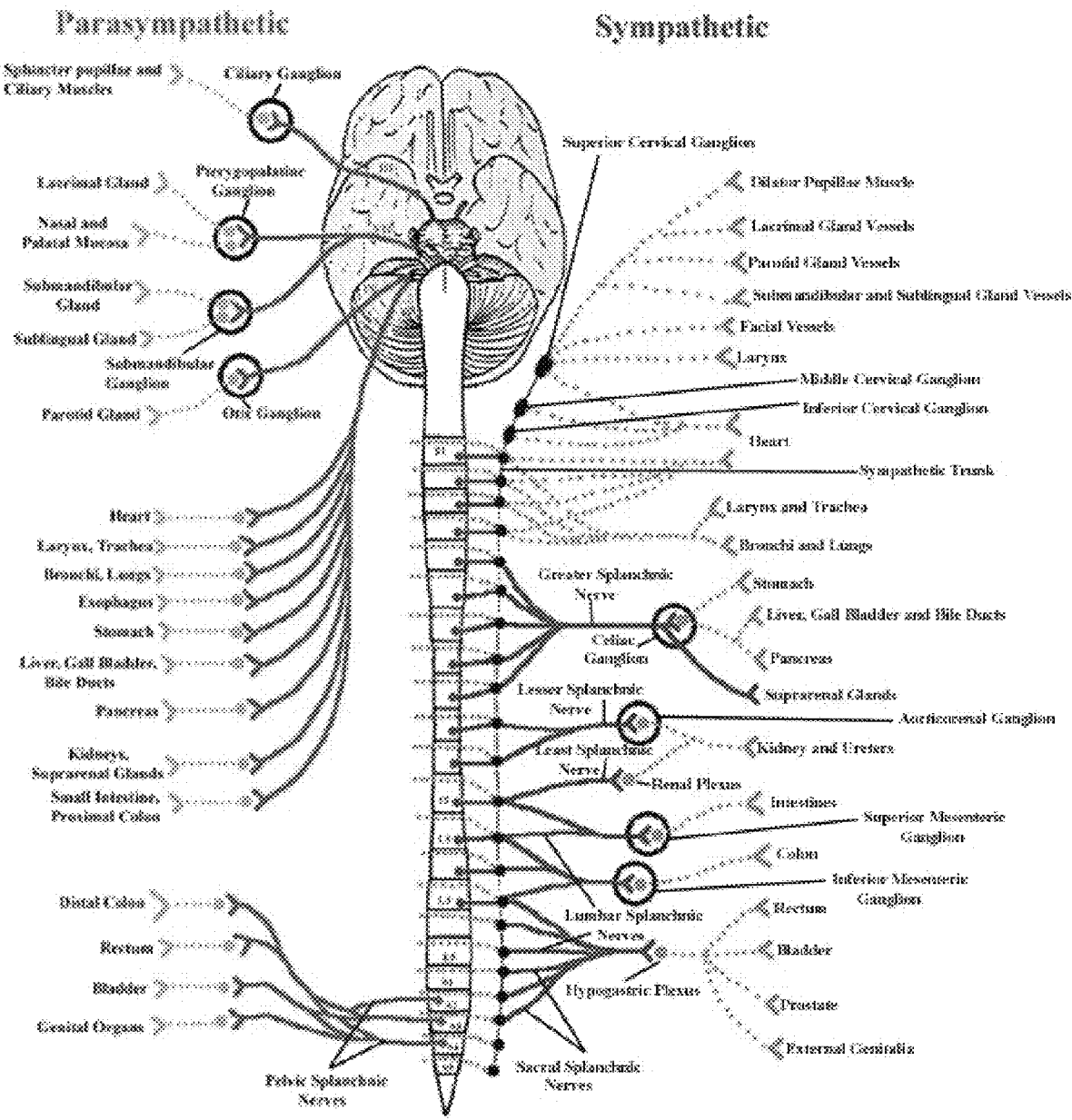
FIG. 13 is an illustration of the anatomy of nerve innervations of the sympathetic (blue) and parasympathetic (red) systems.
Figure 14:
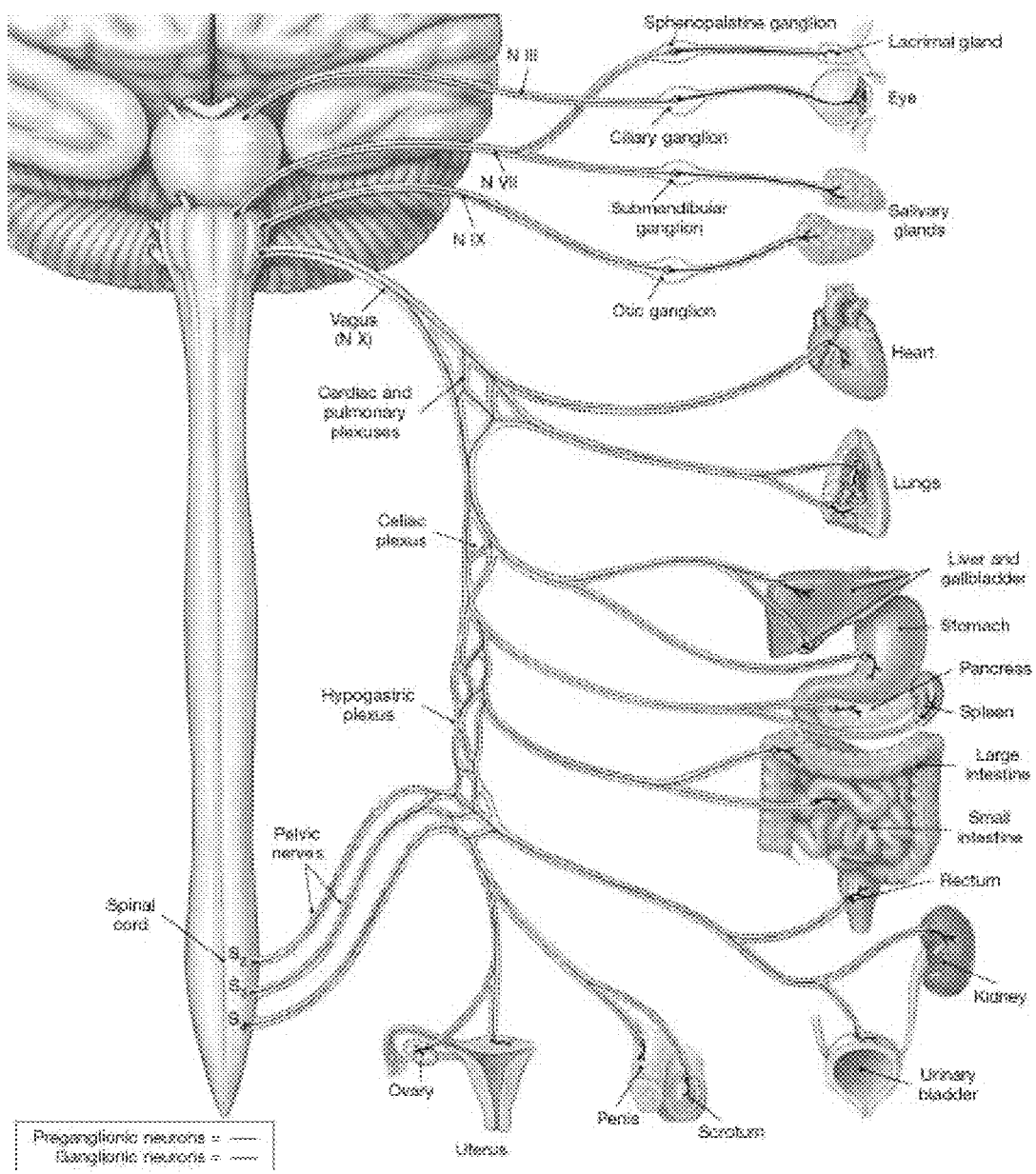
FIG. 14 is an illustration of the anatomy of nerve innervations, and preganglionic and ganglionic neurons.
Figure 15:
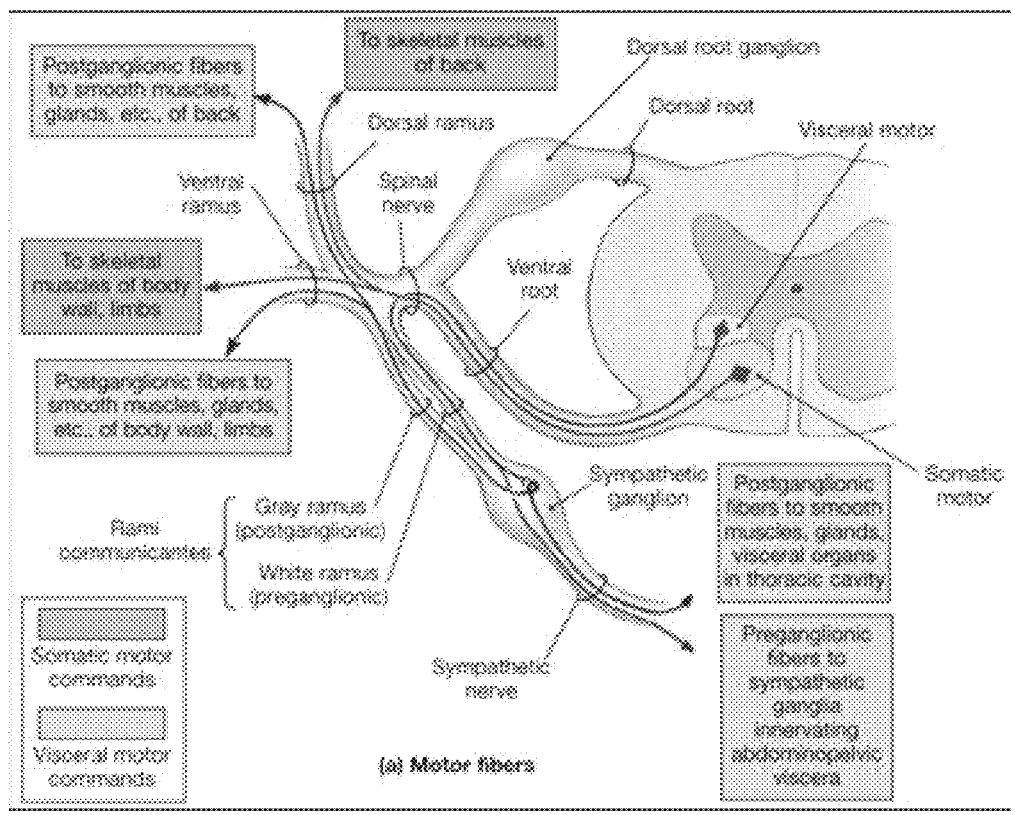
FIG. 15 is an illustration of the anatomy of somatic (orange) and visceral (blue) motor fibers.
Figure 16:
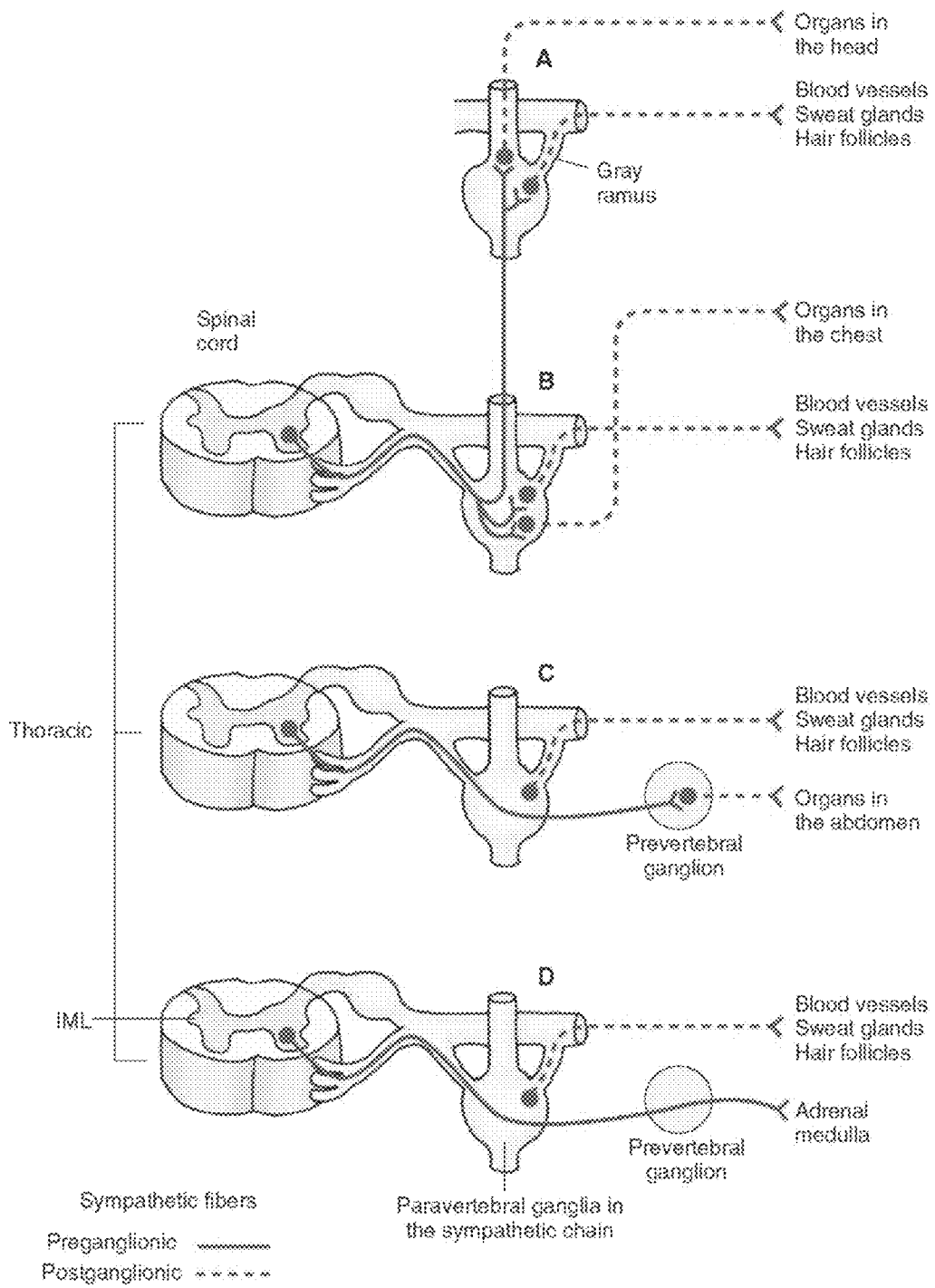
FIG. 16 is an illustration of the anatomy of nerve innervations, and preganglionic and ganglionic neurons.
Figure 17:
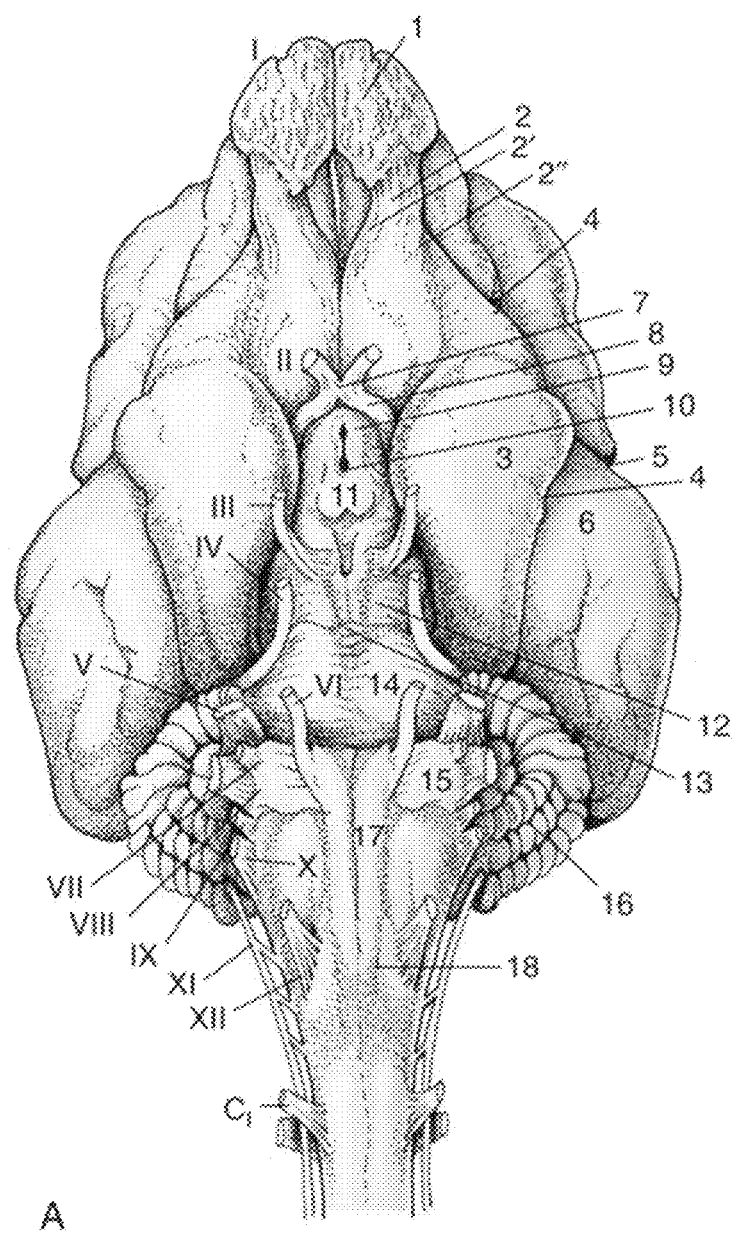
FIG. 17 is an illustration of the anatomy of nerve innervations.
Figure 18:
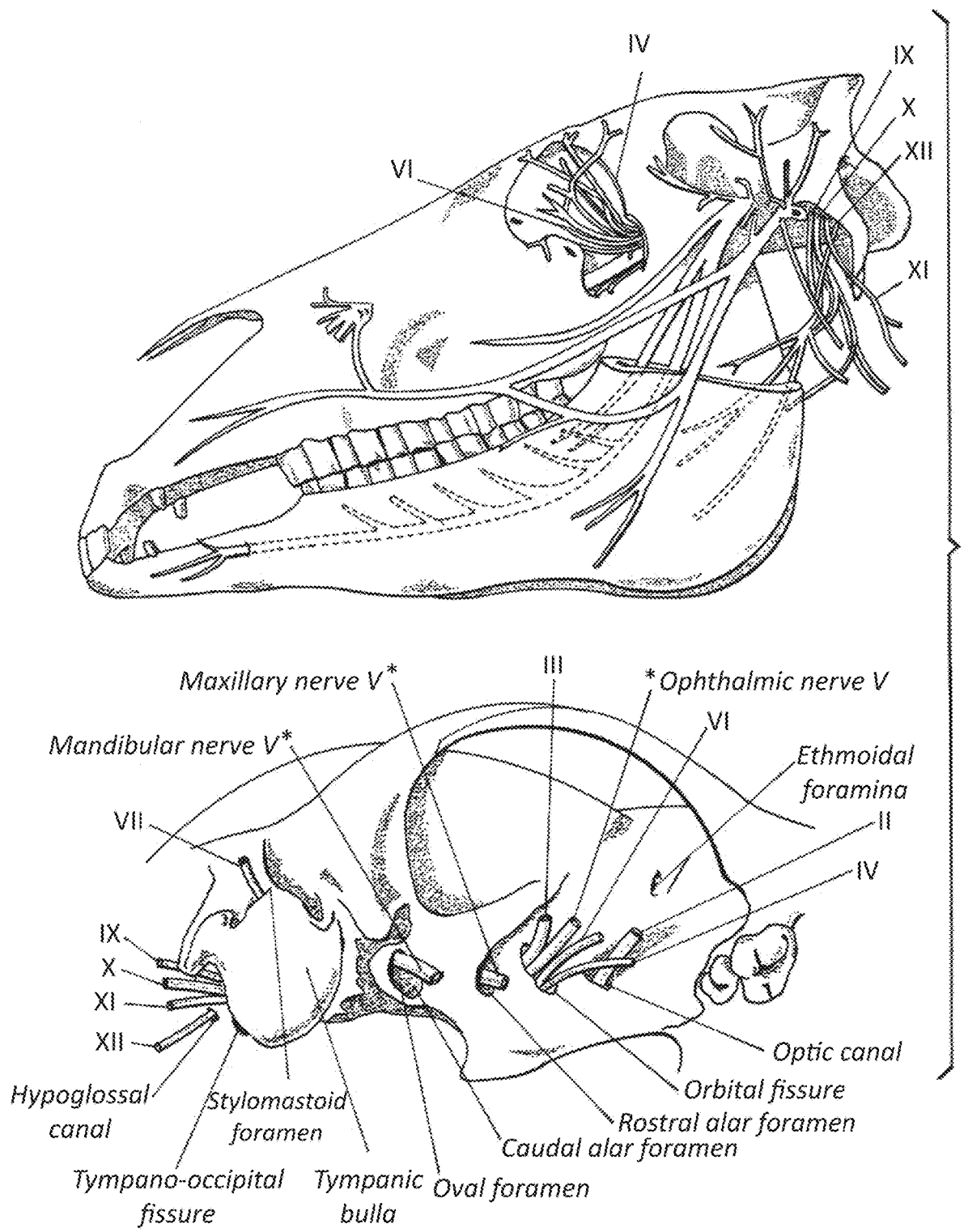
FIG. 18 is a map of cranial nerves in equines (top), canines (bottom), and felines (continuation page).
Figure 19:
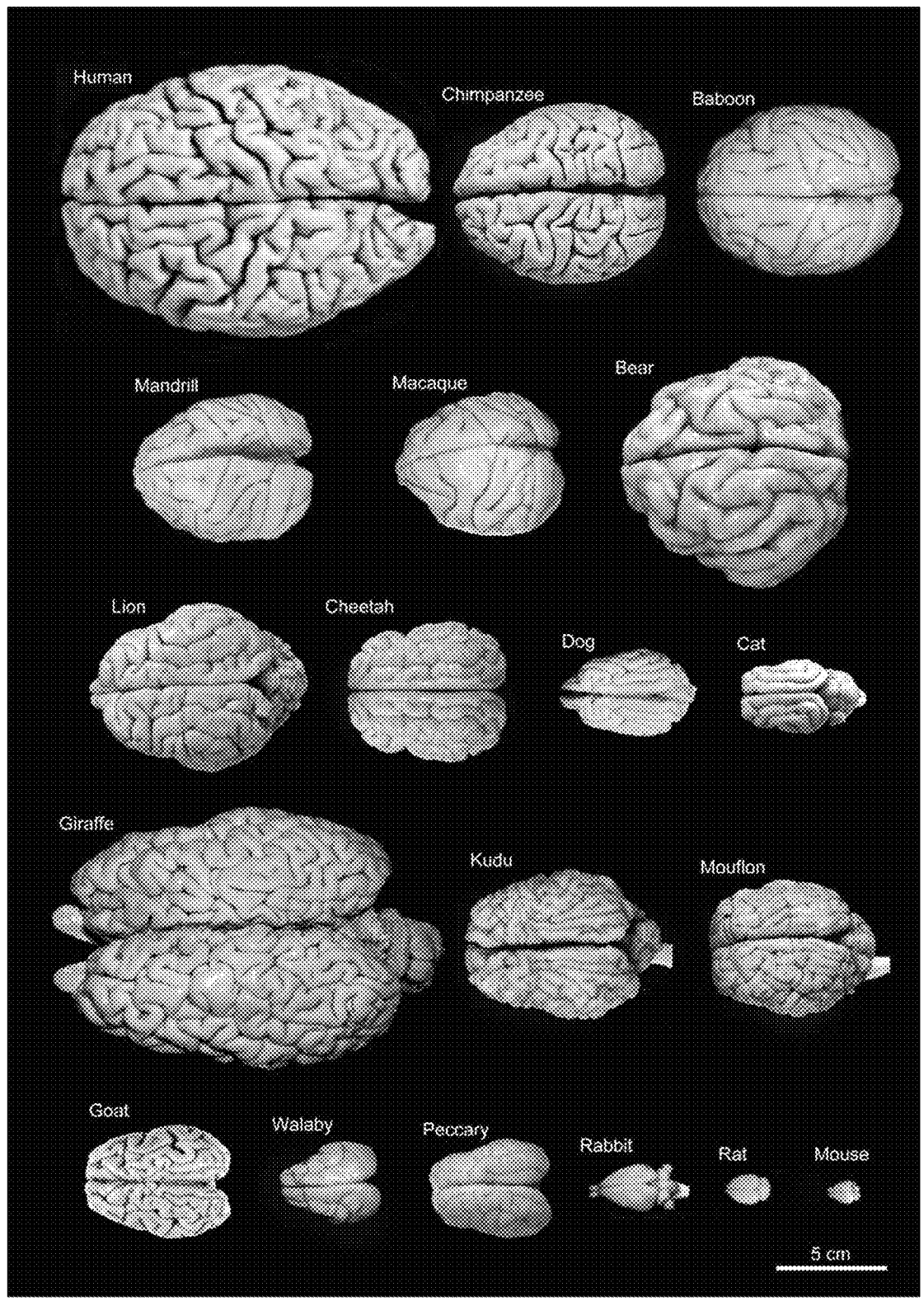
FIG. 19 is an illustration of brains of various vertebrate species.

General somatic afferent fibers (GSA or somatic sensory nerves) afferent fibers arrive from cells in the spinal ganglia and are found in all the spinal nerves, except occasionally the first cervical, and conduct impulses of pain, touch, and temperature from the surface of the body through the posterior roots of the spinal cord and impulses of muscle sense, tendon sense, and joint sense from the deeper structures. General somatic afferent fibers travel through the sympathetic chain into the spinal nerve into the dorsal root ganglion into the dorsal root and into the spinal cord. It can travel up the spinal cord to the central nervous system to the thalamic level and then onto the cerebrum where they can be involved in a reflex arch involving visceral motor and somatic motor nerves which also travel from the ventral root back through the sympathetic chain to their respectful organs. FIGS. 12-13. It is not known at this time whether the modulation of the sympathetic paravertebral and prevertebral nervous system modulates pain at the ganglion or at the thalamic level at this time. Without being bound by theory, general somatic afferent pain and general visceral afferent pain can be modulated through auricular anesthesia topically applied to the external canal modulating the vagus nerve and its attachments to the sympathetic nervous system.

Vertebrate anatomy has many common neurologic anatomic and physiologic aspects. There is no reason to preclude the usage of topical anesthesia or auricular modulation of the external auditory canal for purposes of modulating disease via cranial nerves and the sympathetic nervous system in other vertebrate species namely primates, felines, canines, bovines, and rodent species. Without being bound by theory, other vertebrate species can also benefit from the treatment of specific cranial nerve-associated diseases by way of auricular modulation of the autonomic nervous system. The method comprises topically administering to an ear canal of a vertebrate subject a pharmaceutical composition comprising: i. an analgesic, and/or ii. an anesthetic to the external auditory canal.

Cranial Nerves.

Figure 2:
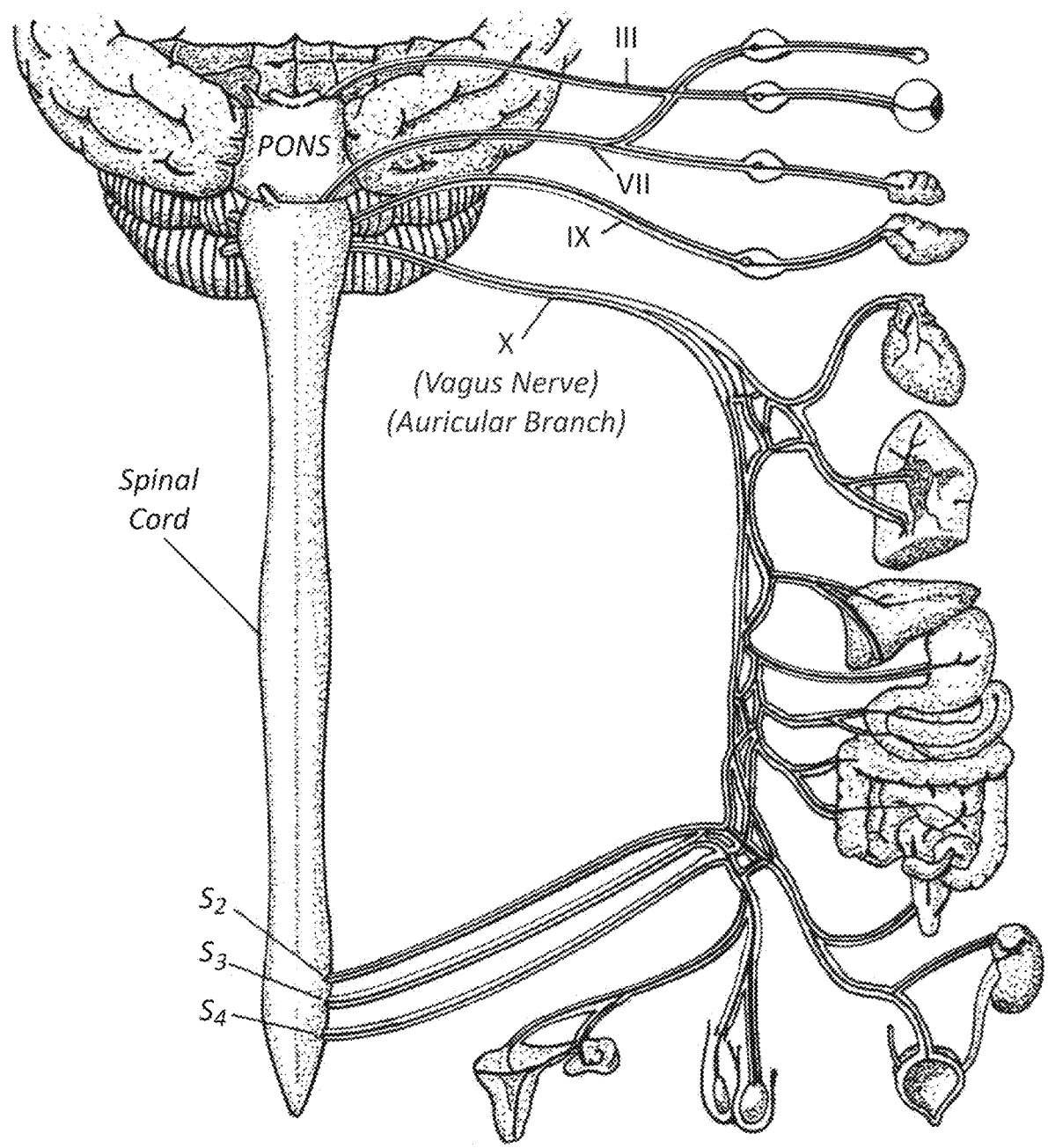
FIG. 2 is an illustration of the complex anatomy of the vagus nerve showing the innervation of the parasympathetic division on one side of the body.

The vagus nerve, also known as cranial nerve X, is the tenth of twelve paired cranial nerves and is the longest of the cranial nerves. Upon leaving the medulla between the medullary pyramid and the inferior cerebellar peduncle, it extends through the jugular foramen, then passes into the carotid sheath between the internal carotid artery and the internal jugular vein down below the head, to the neck, chest and abdomen, where it contributes to the innervation of the viscera. The anatomy of the vagus nerve is illustrated in FIGS. 1 and 2.

Upon exiting the jugular foramen, the vagus nerve forms the jugular ganglion and the ganglion nodosum or the superior and inferior vagal ganglion. The jugular ganglion is joined by filaments from the petrous ganglion of the glossopharyngeal nerve. The auricular branch of the vagus nerve also has connections from the jugular ganglion often and the petrous ganglion of the glossopharyngeal nerve as it enters the mastoid canaliculus from the lateral wall of the jugular fossa. Brushing the temporal bone, the auricular branch of vagas exits the tympanomastoid fissure and divides into two branches; one joins the post-auricular nerve and the other is distributed to the skin of the back of the ear and to the posterior external acoustic meatus.

The vagus nerve conveys sensory information about the state of the body's organs to the central nervous system. Approximately 80% of the nerve fibers in the vagus nerve are afferent, or sensory nerves, communicating the state of the viscera to the brain, while the remaining 20% are efferent, or functional nerves.

The vagus nerve is responsible for regulating a host of bodily functions, including, but not limited to, breathing, speech, sweating, facilitating in keeping the larynx open during breathing, monitoring and regulating heartbeat, and digestion of food in the stomach, along with a host of other physiological functions.

Consequently, manipulation of the vagus nerve and subsequent alteration of its normal physiological function may have profound effects upon a wide range of human ailments that are associated with vagus nerve regulation. However, the present procedures available in the art for altering the function of the vagus nerve are highly invasive. These current procedures often rely upon the implantation of artificial mechanical devices into the body of a patient. Besides being highly invasive surgical procedures, these methods are very costly.

For instance, the United States Food and Drug Administration approved a procedure called vagus nerve stimulation (VNS) in the late 1990s for the treatment of partial onset epilepsy. VNS is performed as a surgical procedure to install a pacemaker-like device into a subject suffering from epileptic seizures. The device, implanted inside a patient's neck area, is used to send mild electrical impulses through the vagus nerve. The device is battery operated, and has an electrical pulse generator. After it is implanted, electrodes with insulated plastic are run into the vagus nerve from under the skin on the patient's neck. The pulse is set to operate alternately, by turning on every few seconds and then turning off.

Researchers have also begun to investigate the possibility of utilizing these pacemaker-like devices in the stomach of obese patients to block the function of the vagus nerve, in order to suppress appetite. Again, these procedures are highly invasive and involve the implantation of artificial devices into the body of a patient.

Some surgeons have even performed vagotomy procedures to treat obesity. In these procedures, the surgeon completely severs a patient's vagus nerve. While these procedures successfully allowed the subjects to lose weight, it is apparent that such an invasive and permanent surgical procedure is problematic for many patients.

Figure 3:
FIG. 3 is an illustration of the anatomy of the facial nerve.

Cranial nerve seven or the facial nerve is one of the twelve paired cranial nerves (see FIG. 3). It is so named because its main function is to supply motor innervation to the muscles of the face. Other muscles it innervates are the platysma, the posterior belly of the digastric, and the stapedius muscle. The sensory and parasympathetic portion of the facial nerve travels in the nervus intermedius and supplies the following components: (1) taste to the anterior two-thirds of the tongue; (2) secretory and vasomotor fibers to the lacrimal gland, the mucus glands of the nose and sinuses, mouth, and the submandibular and sublingual salivary glands; and (3) cutaneous sensory impulses from the external auditory meatus and regions of the back of the ear. It is also thought that a parasympathetic impulse from the nervus intermedius, to the sphenopalatine ganglion, to the mucosa and submucosa of the nose and paranasal sinuses determines their venous capacitance and level of congestion.

The parasympathetic portion of the seventh cranial nerve takes its origin in the nucleus salivatorius in the brain stem and enters the interior acoustic meatus separate from the motor division of the facial nerve. It combines with the facial nerve proximal to the geniculate ganglion. The fibers leave the geniculate ganglion through the great superficial petrosal nerve and are joined by the large deep petrosal nerve to form the vidian nerve, or the nerve of the pterygoid canal, where together they move forward to synapse in the sphenopalatine ganglion. There they provide parasympathetic innervation to the eye, nose, sinus, palate, pharynx, and salivary glands. The geniculate ganglion receives general somatic afferent fibers from the external auditory canal via the auricular branch of the vagus nerve and its connection to the seventh cranial nerve. General somatic sensory afferent fibers synapse in the geniculate ganglion.

Figure 4:
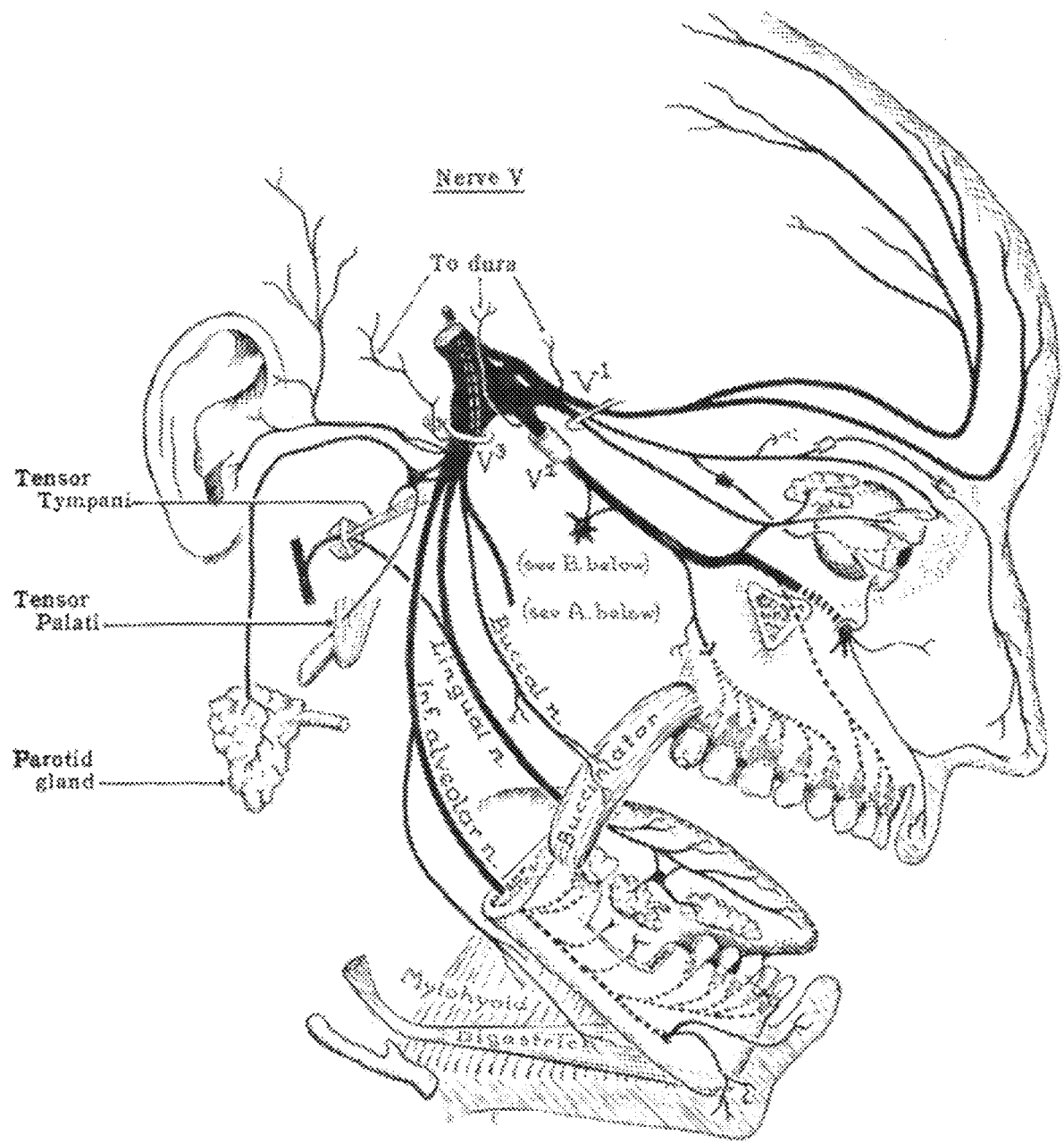
FIG. 4 is an illustration of the anatomy of the trigeminal nerve.

The trigeminal nerve or the fifth cranial nerve is the fifth of twelve paired cranial nerves and is the largest of all the cranial nerves (see FIG. 4). It is the great sensory nerve of the skin of the face, scalp, ear canal, the mucus membranes and other internal structures of the head. It also has functions as motor innervation to the muscles of mastication and contains proprioceptive fibers. It further carries sensory innervation from the dura of the brain with its various branches. The fifth cranial nerve is quite extensive. The main sensory nucleus extends from the pons to the upper spinal cord. The nucleus receives its afferent fibers from the semi-lunar ganglion, also known as the Trigeminal ganglion or the Gasserian ganglion. The Trigeminal ganglion contains the cell bodies of the sensory fibers for its three main divisions. It receives three large sensory division: the ophthalmic, maxillary, and mandibular divisions. The sensory root fibers leave the ganglion posteriorly to pass their insertion into the pons.

Figure 5:
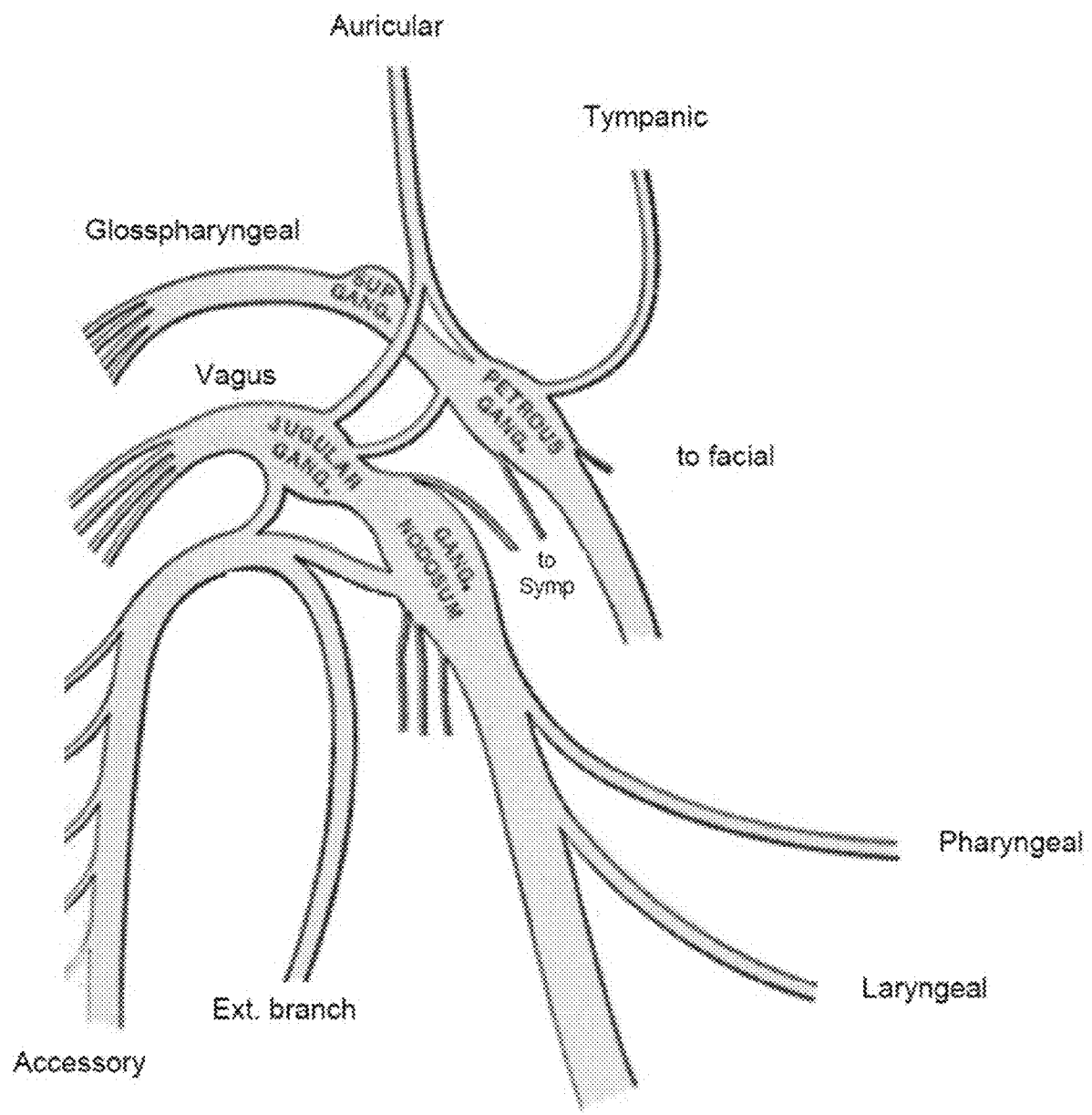
FIG. 5 is an illustration of the anatomy of the glossopharyngeal nerve.
Figure 6:
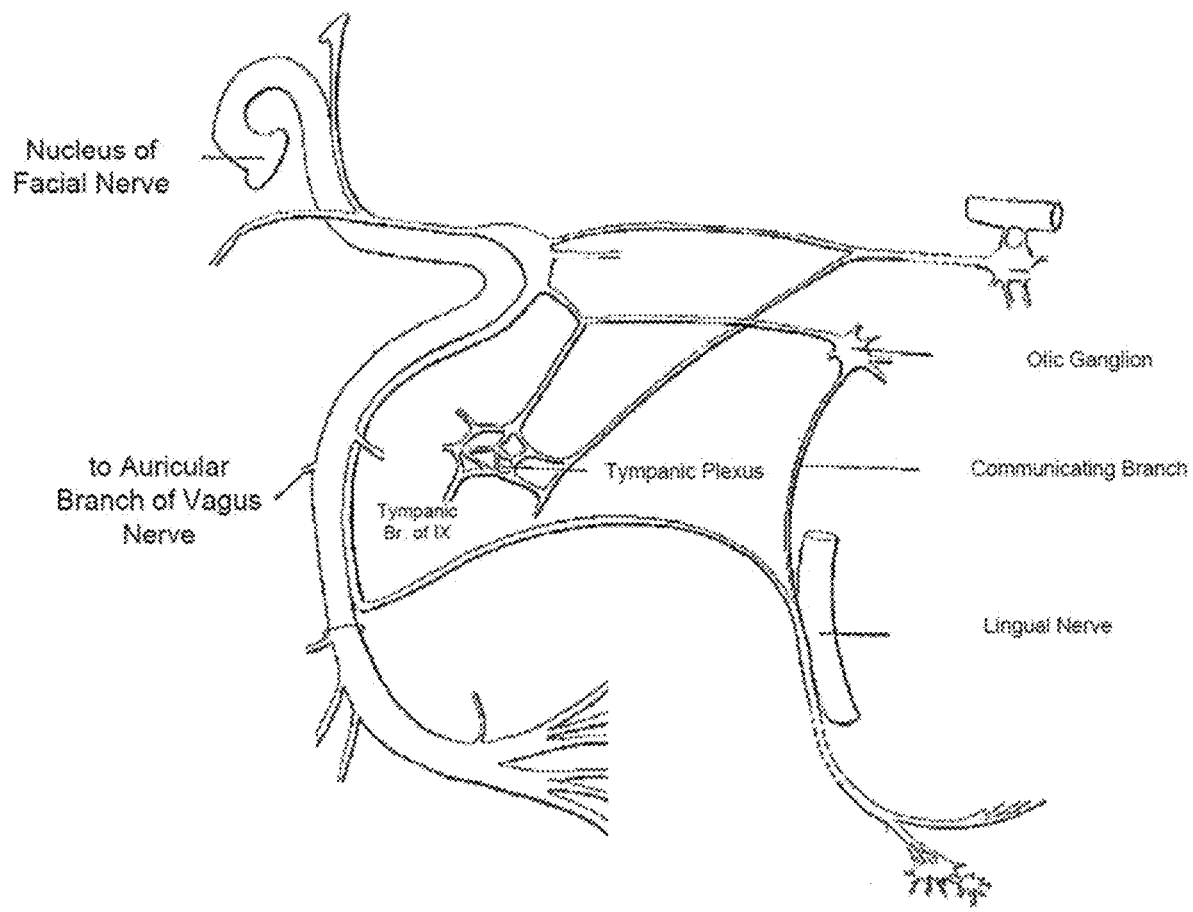
FIG. 6 is an illustration of the glossopharyngeal nerve.

The glossopharyngeal nerve, also known as the ninth cranial nerve, is the ninth of twelve paracranial nerves that is known as the tympanic nerve and has both sensory and secretory fibers (see FIGS. 5 and 6). The nerve is a mixed sensory and motor nerve. The sensory component consists of somatic afferent fibers supplying sensation to the mucus membranes of the pharynx and tonsillar region and back of the tongue. The superficial origin of the glossopharyngeal nerve from the brain stem is by three or four rootlets in the groove between the olive and the inferior peduncle. It exits the skull through the jugular foramen and runs anteriorly between the internal carotid artery and the internal jugular vein. Upon exiting the jugular foramen, it forms a pair of ganglionic swellings: the superior or jugular ganglion, and the inferior or petrosal ganglion. The ganglion contains cell bodies of the sensory fibers of the nerve. The ninth nerve communicates with the vagus nerve or the tenth cranial nerve, the facial nerve, and the sympathetic ganglion. The glossopharyngeal nerve has five distinct general functions: (1) motor (special visceral efferent) supplies the stylopharyngeus muscle; (2) visceral motor (general visceral efferent) provides parasympathetic innervation of the parotid gland; (3) visceral sensory (general visceral afferent) carries visceral sensory information from the carotid sinus and carotid body; (4) general sensory (general somatic efferent) provides general sensory information from the skin of the external ear, internal surface of the tympanic membrane, upper pharynx, and posterior one-third of the tongue; and (5) special sensory (special afferent) provides taste sensation from the posterior one-third of the tongue, including circumvallate papillae.

The accessory nerve or the spinal accessory nerve is cranial nerve 11. The cranial nerve controls the sternocleidomastoid muscle and the trapezius muscle. The sternocleidomastoid muscle tilts and rotates the head while the trapezius muscle has several factors on the scapula including shoulder elevation and abduction of the arm. Range of motion and strength testing in the neck and shoulders can be measured during a neurological exam to assess the function of the spinal accessory nerve. Limited range of motion or poor muscle strength indicate damage to the spinal accessory nerve. This can be the result from a variety of causes of the cranial nerves. The spinal accessory nerve exits the cranium through a specialized hole or foramen. The nerve originates in the majority of individuals in the neurons situated in the upper spinal cord. From there, the fibers enter the foramen magnum and course along the inner wall of the skull toward the jugular foramen through which it exits the skull with the glossopharyngeal (or 9th cranial nerve) and the vagus nerve (or the 10th cranial nerve) owing to is peculiar course the spinal accessory nerve is notable for being the only cranial nerve to both enter and exit the skull (FIG. 1, FIG. 2, and FIG. 5). Once the nerve exits the jugular foramen, it crosses the internal jugular vein around the level of the posterior belly of the digastric muscle. It courses on to innervate the trapezius and sternocleidomastoid muscles. Function of the spinal accessory nerve is special visceral efferent or innervation and function of the motor control of the sternocleidomastoid and trapezius muscle. Abnormalities of the spinal accessory nerve can cause spasm of these two muscles along with fasciculation and weakness or aberrations in head, neck, shoulder, and arm movements and range of motion. The spinal accessory nerve is intimately connected to the vagus nerve that is the superior and inferior ganglion of the vagus nerve. Auricular anesthesia of the vagus nerve directly modulates electrical input and function of the spinal accessory nerve (see FIG. 5).

The hypoglossal nerve is the 12th cranial nerve, and innervates the muscles of the tongue. The nerve arises along with the other cranial nerves in the brain stem. The nerve exits the skull base in the posterior fossa through the hypoglossal canal. As it exits the skull, it gives off a small meningeal branch and picks up a branch from the anterior ramus of C1. It follows in near proximity to the vagus nerve and the spinal position of the accessory nerve and it follows behind the vagus nerve and passes between the internal carotid artery and the interior jugular vein lying on the carotid sheath. It passes deep into the posterior belly of the digastric muscle in the submandibular region. It passes lateral to the hyoglossus muscle in the inferior laryngeal nerve to reach and efferently innervate the tongue. It is intimately involved in speech as it innervates the tongue. It innervates intrinsic and extrinsic muscles of the tongue and is characterized as general somatic efferent nerve type. It can be modulated by indirect modulation or anesthesia to the vagus nerve, which directly communicates to the hypoglossal nerve (see FIG. 1 and FIG. 5). The hypoglossal nerve is involved in speech, as well as swallowing to clear the mouth of saliva and other involuntary activities completed by the tongue. Most functions are voluntary. Voluntary functions require conscious thought and nerve pathways occur in the corticobulbar region of the spinal cord. The hypoglossal nucleus is supplied by innervation from the reticular formation by which it is involved in several reflexive or automatic motions and in aiding unconscious movement required upon engaging in speech and articulation. Modulation of signals to the hypoglossal nerve via the 10th cranial nerve may have profound effects on the improvement of articulation, speech, swallowing, and posterior fossa headaches.

Thus, there is a great need in the medical community for methods of treating vagus and other cranial nerve associated diseases that are not dependent upon altering the function of the vagus nerve or other cranial nerves through invasive surgical procedures or artificial devices. Specifically, there is a great need in the art for procedures to alter the function of the vagus and other cranial nerves that are non-invasive, safe, effective, and economical Disrupting Transduction of Neurological Signals Along the Cranial Nerves.

The present invention provides for methods of treating a variety of diseases disclosed herein that comprises performing auricular anesthesia (e.g., topical anesthesia) of the external auditory canal for the purposes of anesthetizing cranial nerves 5, 7, 9, 10, 11, and/or 12. The present invention also provides for methods of treating a variety of diseases disclosed herein that comprises performing auricular anesthesia (e.g., topical anesthesia) of the sympathetic and/or parasympathetic nervous system(s). The present invention further for methods of treating a variety of diseases disclosed herein that comprises performing auricular anesthesia of general visceral afferent, general somatic afferent, general visceral efferent, and/or general somatic efferent nerves. In some embodiments, auricular anesthesia is performed in a variety of vertebrate species including but not limited to species such as humans, horses, cows, pigs, dogs, cats, etc. In some embodiments, auricular anesthesia is performed by way of administering a combination of lidocaine and tetracaine combined in solution with an excipient glycerin with and without the presents of epinephrine. Antipyrine and Benzocaine can also be used in conducting auricular anesthesia of the external auditory canal for the purpose of treating diseases (see Examples herein). Glycerin is a usp based substance of the excipient. Tetracaine may also be administered without epinephrine to obtain similar results. Other excipients will also be utilized to carry the topical anesthetic or topical analgesic. In one embodiment, the present disclosure provides a method for treating symptoms of a disease which comprises topically administering to an ear canal of a subject a pharmaceutical composition comprising of an anesthetic and another anesthetic. In some embodiments, an analgesic with an anesthetic may also be utilized. This would be a separate eardrop in and of itself. In one embodiment, the analgesic is antipyrine, but could also consist of other known analgesics. In an embodiment, the anesthetic is at least one of a selected group consisting of an amide or an ester compound discussed herein.

The tenth cranial nerve (vagus nerve) is associated with numerous bodily organs and alteration of its normal physiological function can have profound effects on a host of human ailments. That is, by "blocking" or "disrupting" or "numbing" the conduction of neurological signals in the particular nerve, one is able to influence a host of organs that are innervated by that nerve. Consequently, blocking the transduction of signals transmitted along the nerve, whether those signals are afferent or efferent in nature, will alter the normal physiological response of various organs and tissues. This, in turn, can have profound implications for treating a variety of diseases, or ailments that are associated with human organs and tissues that are innervated by the particular nerve.

Auricular anesthesia of the cutaneous portion of the seventh cranial nerve (facial nerve) carry signals back to the geniculate ganglion where parasympathetic fibers and sensory fibers are anesthetized, blocked, or otherwise modulated. Anesthesia of the geniculate ganglion and its connection to the Sphenopalatine ganglion serve to modulate or block transduction of efferent signals through the facial nerve. This can profoundly affect disease processes such as, but not limited to, allergic rhinitis, vasomotor rhinitis, inflammatory nasal polyposis, chronic sinusitis, chronic nasal congestion, allergic conjunctivitis, sneezing, and rhinitis in all forms.

The sensory aspect of the fifth cranial nerve (trigeminal nerve) deals with information from the dura, the mucus membranes of the eyes, the mucus membranes of the nose and sinuses, the skin of the external auditory canal eardrum. Auricular anesthesia of the skin of the ear canal then signals to the trigeminal ganglion via the auriculotemporal branch of the mandibular division of the trigeminal nerve. Modulation of afferent signals through the trigeminal ganglion has profound effects on multiple disease processes. Modulating those afferent signals from the dura, the eye, the nose and sinuses leads to modulation of various disease processes. Manipulation of dural signals that pass through the ophthalmic, maxillary, and mandibular divisions have profound effects in the treatments of headaches and migraine headaches. Manipulation or modulation or blockage of afferent signals from the ophthalmic and maxillary divisions of the trigeminal nerve will result in modulated efferent signals from the motor division of the seventh cranial nerve that deal with allergic rhinitis, vasomotor rhinitis, all forms of rhinitis, inflammatory nasal polyposis, chronic sinusitis, chronic nasal congestion, allergic conjunctivitis and sneezing.

Auricular anesthesia of the cutaneous portion of the ninth cranial nerve (glossopharyngeal nerve) and its proximity to the petrous ganglion and its connection to the seventh cranial nerve and tenth cranial nerve can have profound effect on certain disease processes. Because of neural connections between the glossopharyngeal nerve and those of the seventh and tenth cranial nerves, disease processes specific to those nerves may also be modulated. Diseases specific to the glossopharyngeal nerve that may be affected by topical auricular anesthesia include, but are not limited to, pharyngeal pain, post tonsillectomy pain, sneezing, and parotid salivation.

Thus, several embodiments of the present invention comprise a method that blocks the transduction of efferent signals via the vagus, trigeminal, facial, or glossopharyngeal nerves. Another embodiment of the disclosure blocks the afferent transduction of signals via the vagus, trigeminal, facial, or glossopharyngeal nerves. The present disclosure also provides a methodology by which both the afferent and efferent signal transduction via the vagus, trigeminal, facial, or glossopharyngeal nerves is blocked.

In one embodiment, the invention provides for a method of treating or ameliorating symptoms in a subject with a disease associated with a particular cranial nerve, wherein the disease is a neurology-psychiatry-related affliction, an ear-nose-throat (ENT)-related affliction, a GU-related affliction, a gastrointestinal (GI)-related affliction, a cardiac-related affliction, a pulmonary-related affliction, or a metabolic-related affliction, the method comprising administering to an ear canal of a subject in need of such treatment an effective amount of a pharmaceutical composition, comprising: (i) at least one analgesic comprising a pyrazolone derivative, and (ii) at least one anesthetic comprising Formula I:

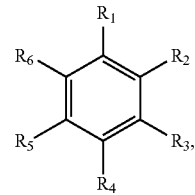

wherein $R_1$ comprises:

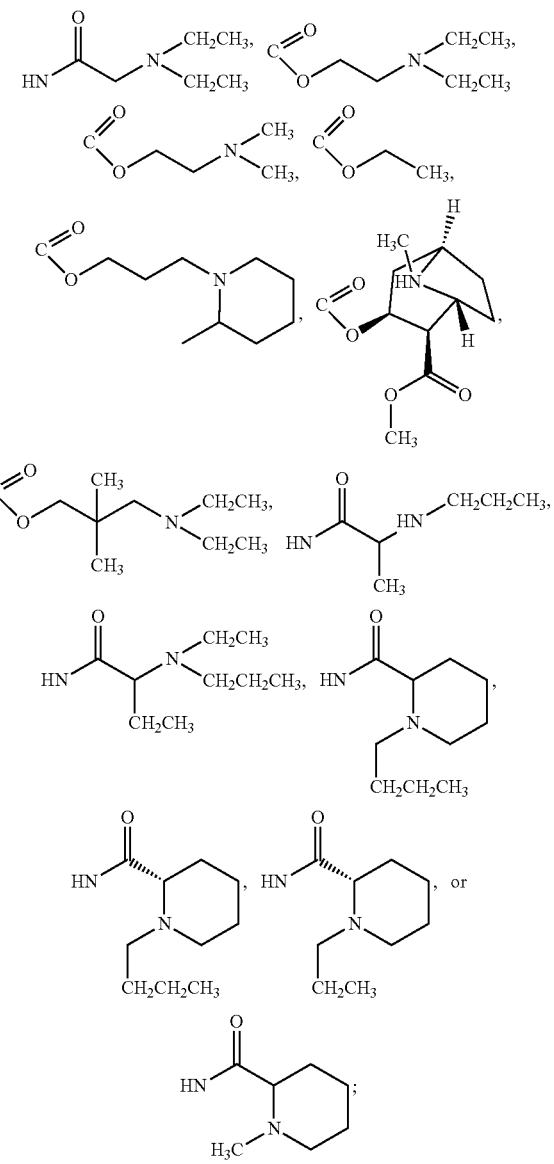

wherein $R_2$ comprises H, $CH_3$, Cl, or

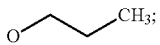

wherein $R_3$ comprises H or $NH_2$; wherein $R_4$ comprises H, $NH_2$, $CH_3$,

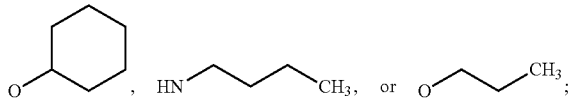

wherein $R_5$ comprises H; and wherein $R_6$ comprises H or $CH_3$, and wherein said pharmaceutical composition is administered to the ear canal of the subject in a concentration sufficient to physiologically alter the activity of the subject's particular cranial nerve compared to the physiological activity of that particular cranial nerve in a subject not administered the pharmaceutical composition. In one embodiment, the particular cranial nerve is the trigeminal nerve, the facial nerve, the glossopharyngeal nerve, the accessory nerve, the hypoglossal nerve, the vagus nerve, or a combination thereof.

Pharmaceutical Compositions.

Figure 7:
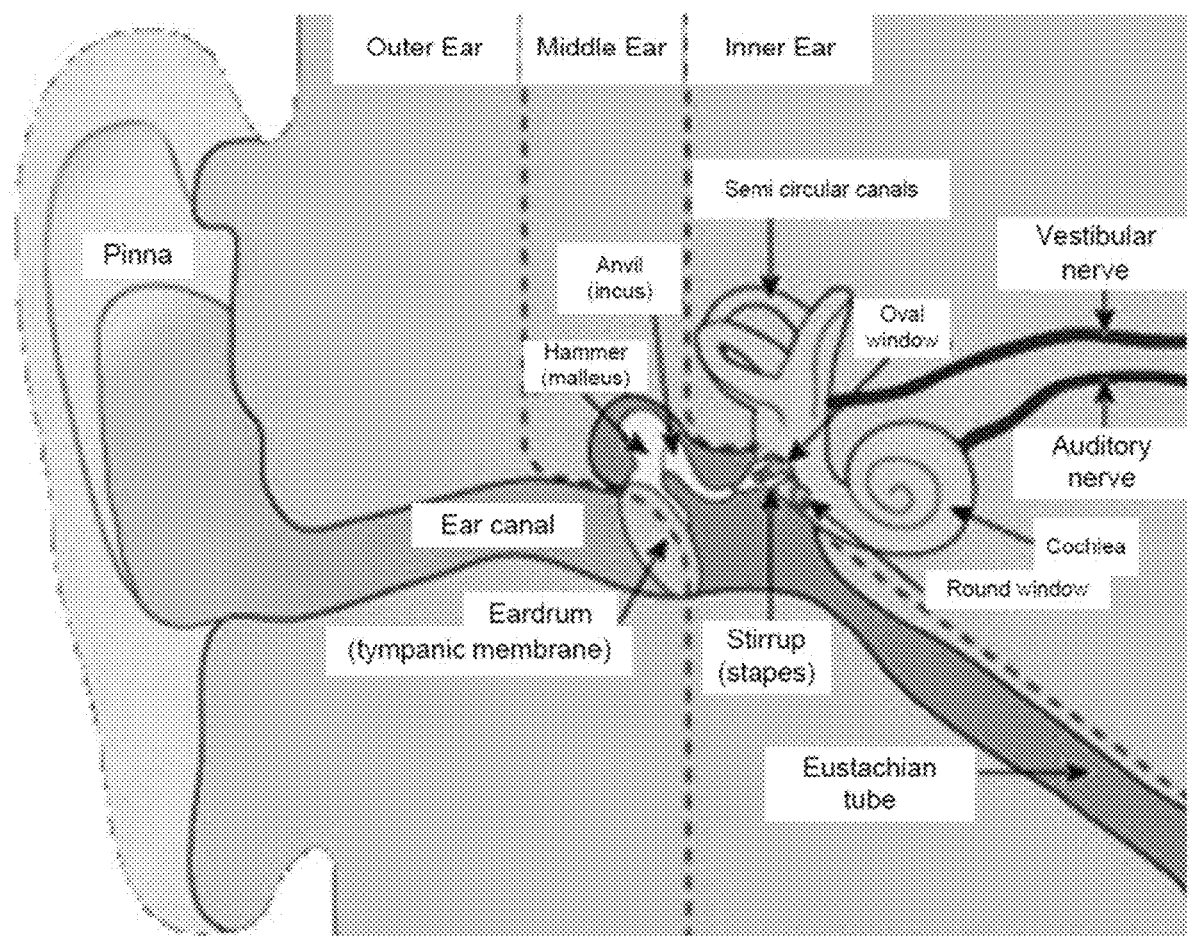
FIG. 7 is an illustration of the interior of a human ear. The ear canal is noted.
Figure 8:
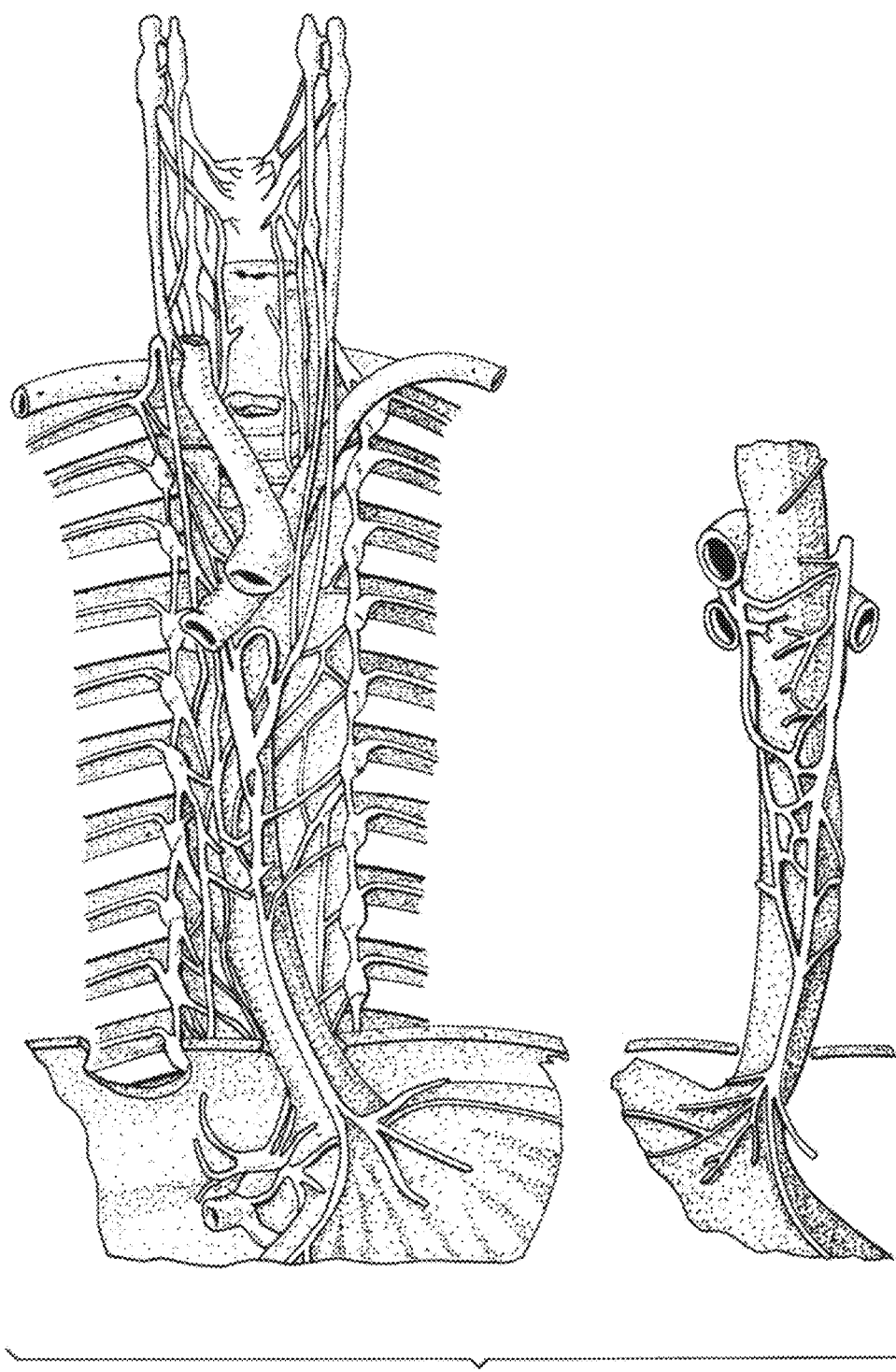
FIG. 8 is an illustration of the nerves of the Esophagus.
Figure 9:
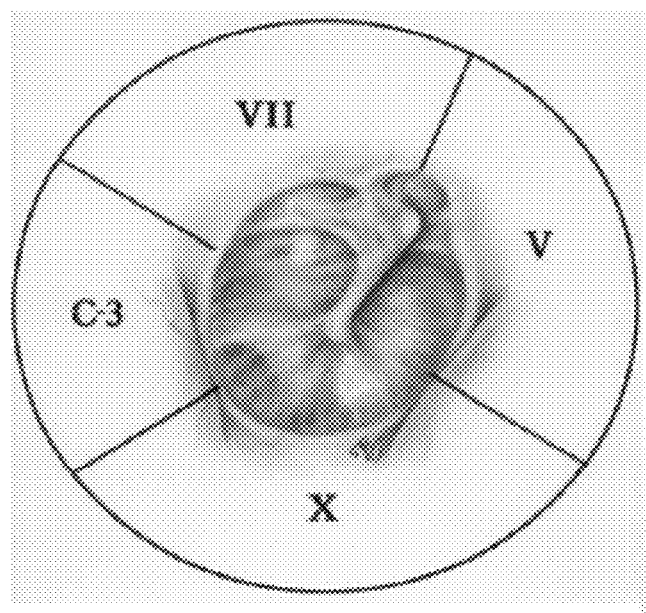
FIG. 9 is an illustration of cranial nerves C-3, 5, 7, and 10.
Figure 10:
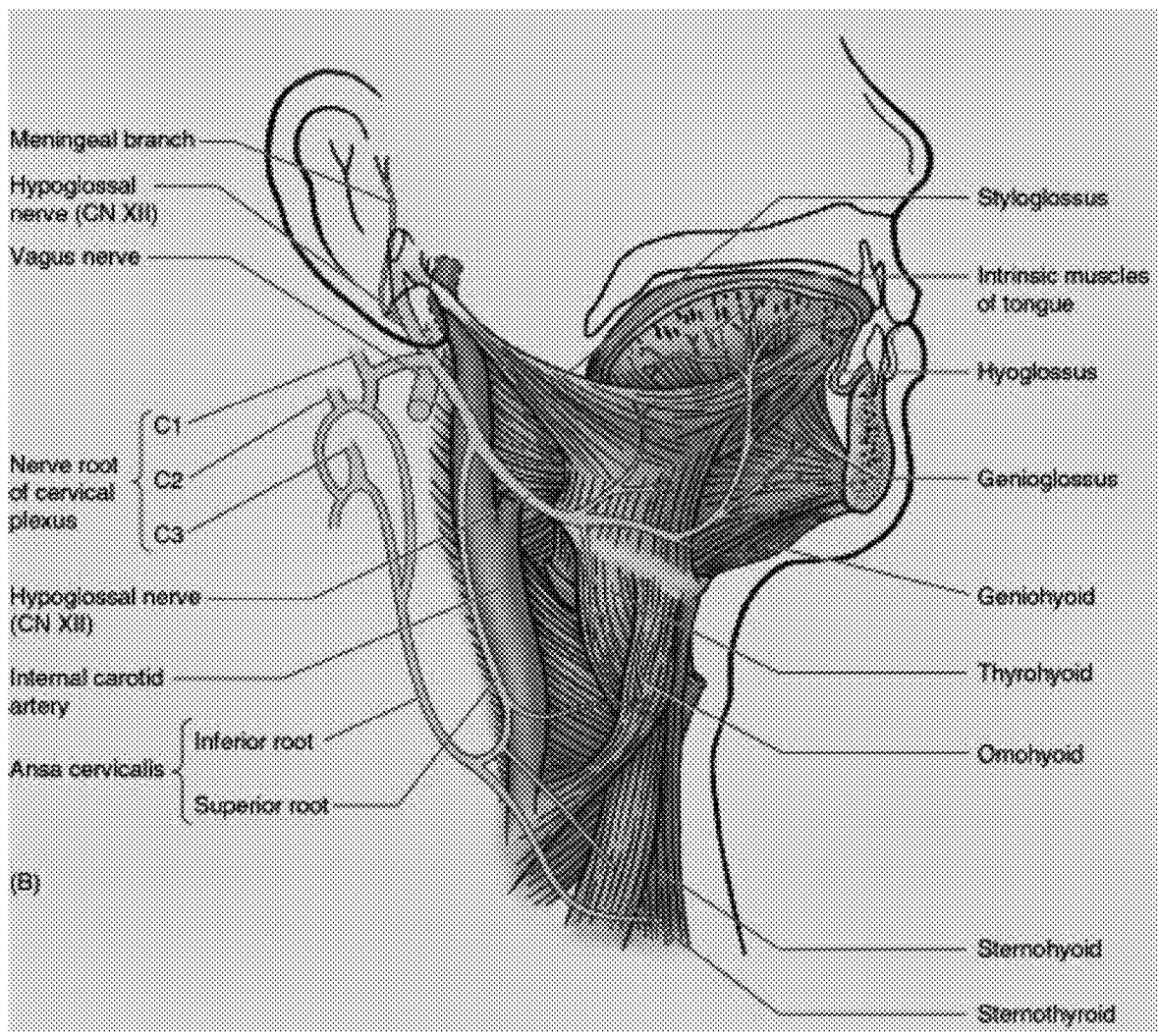
FIG. 10 is an illustration of the distribution of the hypoglossal nerve (cranial nerve 12).
Figure 11:
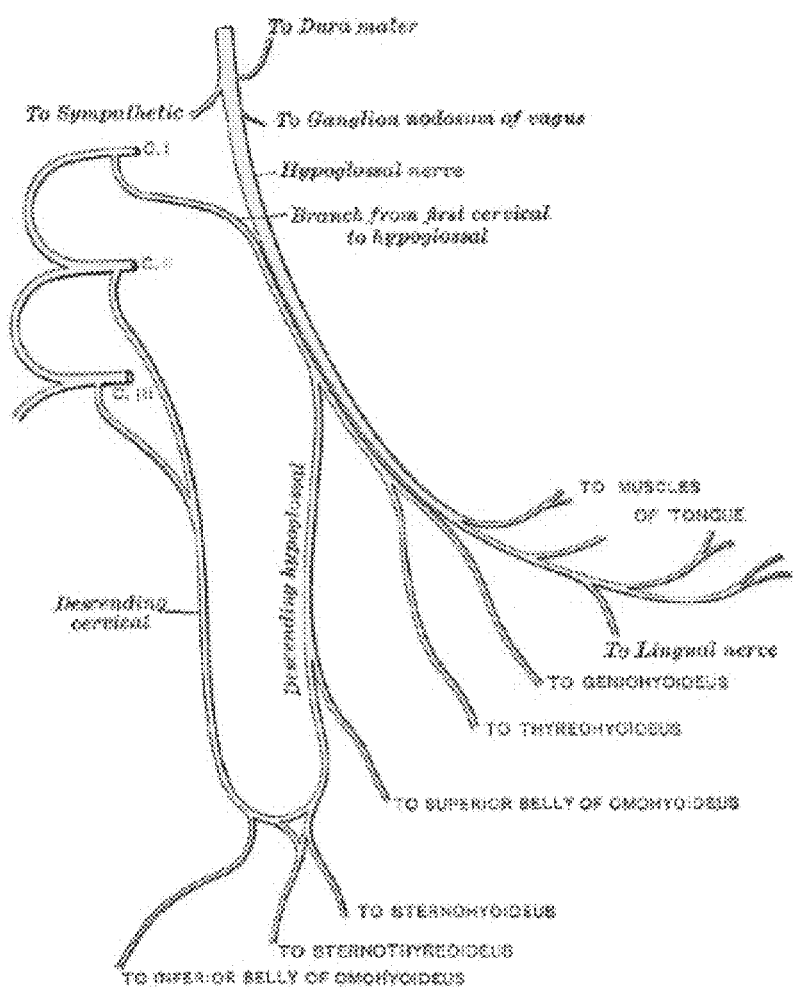
FIG. 11 is an illustration of the anatomy of nerve innervations.

The methods of the present disclosure utilize the application of a pharmaceutical composition to the ear canal of subject in need of such treatment. The ear canal is illustrated in FIG. 7. The pharmaceutical compositions comprise an analgesic and an anesthetic, one or more analgesics, or one or more anesthetics. For example, the composition can comprise one anesthetic, such as lidocaine; two anesthetics, such as lidocaine and bupivacaine; or an anesthetic and an analgesic, such as benzocaine and antipyrine.

The analgesic present in embodiments of the disclosure are pyrazolone ($C_3H_4N_2O$) derivatives. The molecular structure of 3-pyrazolone is as follows:

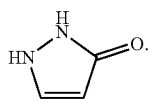

Derivatives of the isomeric form 5-pyrazolone are also encompassed by the disclosure.

Particular embodiments of the present methods utilize antipyrine as the pyrazolone derivative. Antipyrine ($C_{11}H_{12}N_2O$) is also referred to as phenazone. The molecular structure of antipyrine is as follows:

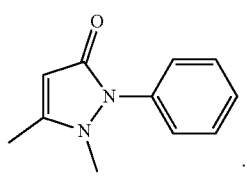

In one embodiment, the methods and pharmaceutical compositions comprise at least one anesthetic comprising Formula I:

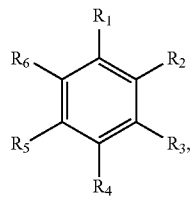

wherein $R_1$ comprises:

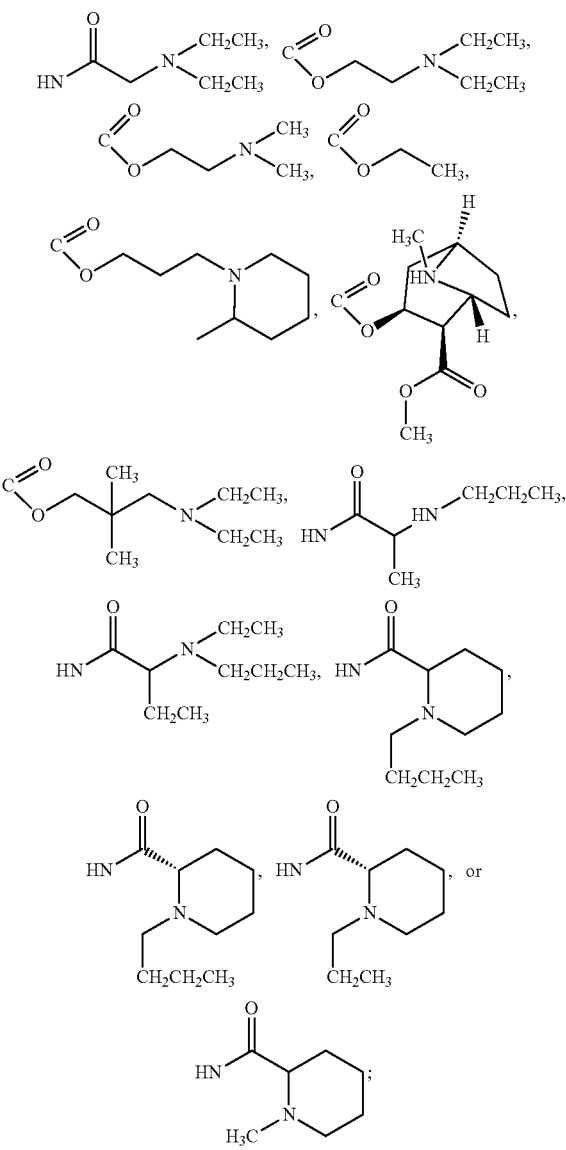

wherein $R_2$ comprises H, $CH_3$, Cl, or

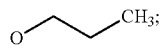

wherein $R_3$ comprises H or $NH_2$; wherein $R_4$ comprises H, $NH_2$, $CH_3$,

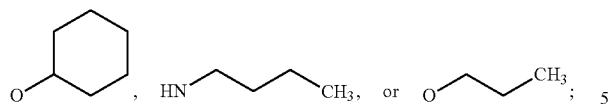

wherein $R_5$ comprises H; and wherein $R_6$ comprises H or $CH_3$.

In another embodiment, $R_1$ of Formula I comprises

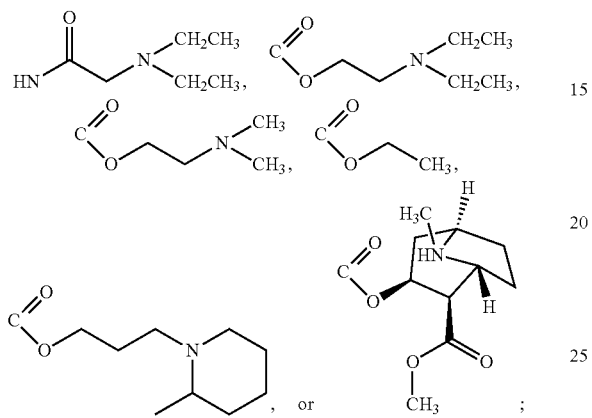

wherein $R_2$ comprises H or $CH_3$; wherein $R_3$ comprises H; wherein $R_4$ comprises H, $NH_2$,

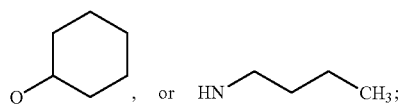

wherein $R_5$ comprises H; and wherein $R_6$ comprises H or $CH_3$.

In one embodiment, the anesthetic comprises

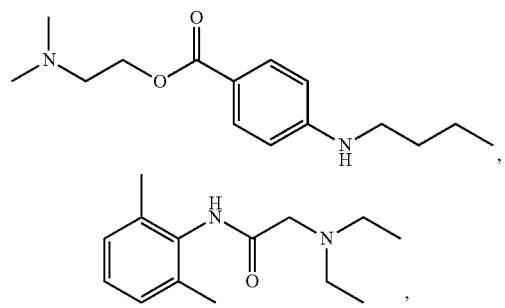

or a combination thereof.

In one embodiment, the anesthetic comprises benzocaine

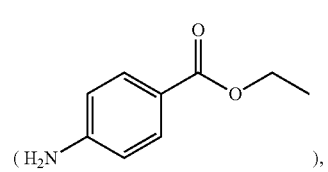

chloroprocaine

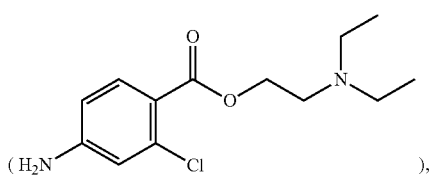 [SMILES: CCN(CC)CCOC(=O)c1ccc(N)cc1Cl]

cocaine

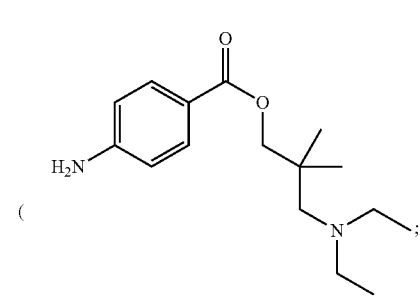 [SMILES: CCN(CC)CC(C)(C)COC(=O)c1ccc(N)cc1]

cyclomethycaine

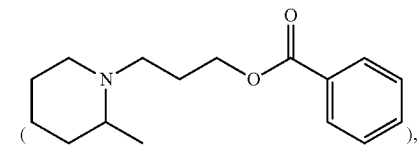

dimethocaine also referred to as larocaine), piperocaine propoxycaine
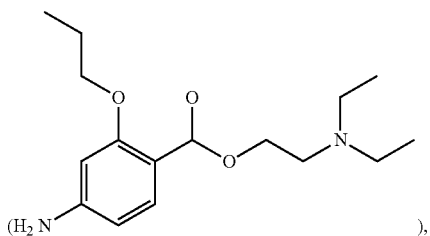
procaine
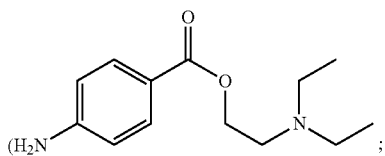
also referred to as novocaine), proparacaine
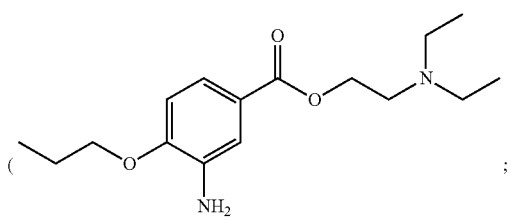 [SMILES: CCCOc1ccc(C(=O)OCCN(CC)CC)cc1N]
also referred to as proxymetacaine), tetracaine
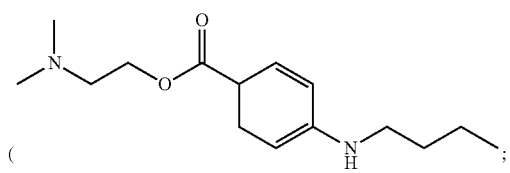 [SMILES: CCCCNC1=CCC(C(=O)OCCN(C)C)C=C1]
also referred to as amethocaine), articaine
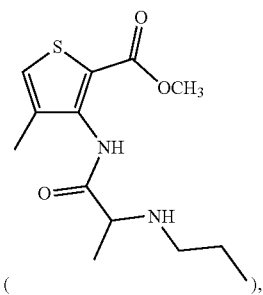 [SMILES: CCCNC(C)C(=O)Nc1c(C)csc1C(=O)OC]
bupivacaine
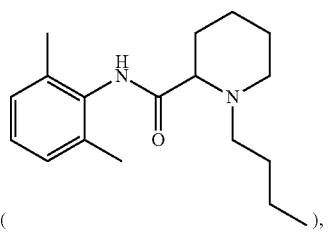 [SMILES: CCCCN1CCCCC1C(=O)Nc1c(C)cccc1C]
cinchocaine
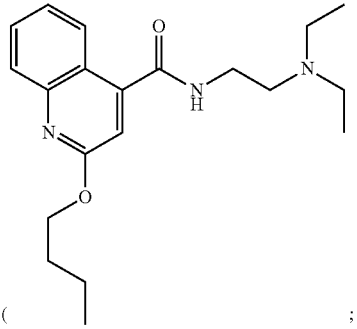 [SMILES: CCCCOc1cc(C(=O)NCCN(CC)CC)c2ccccc2n1]
also referred to as dibucaine), etidocaine
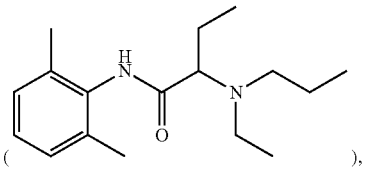 [SMILES: CCCN(CC)C(CC)C(=O)Nc1c(C)cccc1C]
levobupivacaine
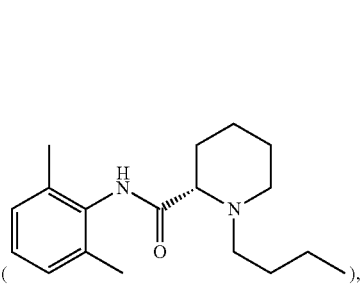 [SMILES: CCCCN1CCCC[C@H]1C(=O)Nc1c(C)cccc1C]
lidocaine
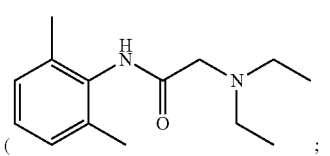

also referred to as lignocaine and xylocaine), mepivacaine

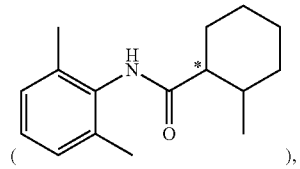 [SMILES: Cc1cccc(C)c1NC(=O)C1CCCCC1C]

prilocaine

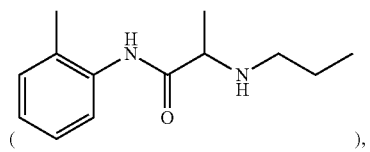 [SMILES: CCCNC(C)C(=O)Nc1ccccc1C]

ropivacaine

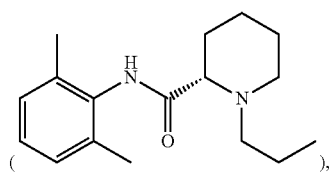 [SMILES: CCCN1CCCC[C@H]1C(=O)Nc1c(C)cccc1C]

farmocaine

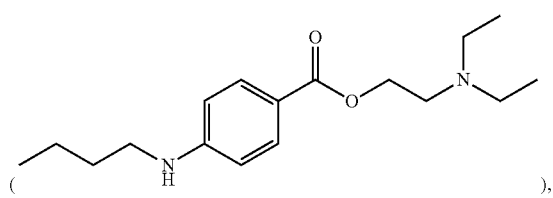 [SMILES: CCCCNc1ccc(C(=O)OCCN(CC)CC)cc1]

trimecaine

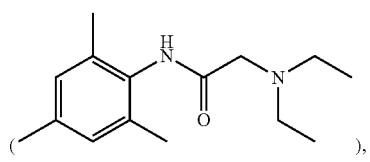 [SMILES: CCN(CC)CC(=O)Nc1c(C)cc(C)cc1C]

a combination of the anesthetics listed herein, or pharmaceutically acceptable derivatives thereof. In another embodiment, the anesthetic is not benzocaine.

In one embodiment, the anesthetic is lidocaine.
In one embodiment, the anesthetic is tetracaine.
In one embodiment, the anesthetic is tetracaine and lidocaine.
In one embodiment, the anesthetic is lidocaine and bupivacaine.

The anesthetic present in some embodiments of the disclosure are ester based anesthetics. In a particular embodiment, the anesthetic is benzocaine ($C_9H_{11}NO_2$), the molecular formula of which is as follows:

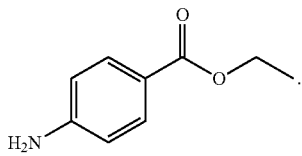

In another embodiment, the anesthetic is not benzocaine.

Further embodiments of the method utilize amide based anesthetics.

In a preferred embodiment of the present methods, the disclosed pharmaceutical compositions comprise antipyrine as the analgesic and benzocaine as the anesthetic.

In some embodiments, the disclosed pharmaceutical compositions comprise antipyrine as the analgesic and tetracaine and/or lidocaine as the anesthetic. In some embodiments, the disclosed pharmaceutical compositions comprise tetracaine and lidocaine as the anesthetic.

In one embodiment, the invention is directed to an otic pharmaceutical composition. In various embodiments, the otic pharmaceutical composition comprises (i) at least one analgesic comprising a pyrazolone derivative, and/or (ii) at least one anesthetic comprising Formula I:

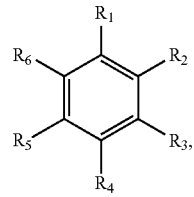

wherein $R_1$ comprises:

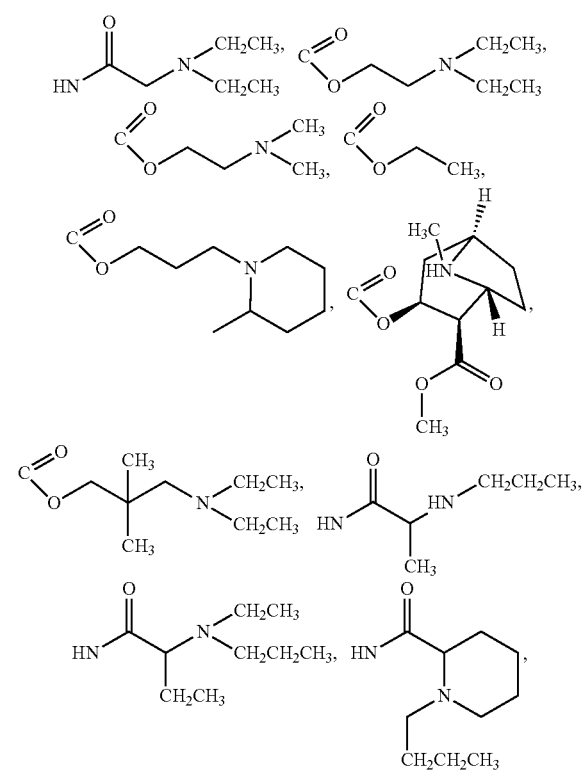

-continued

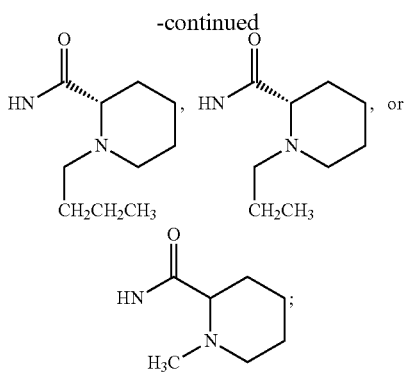

wherein $R_2$ comprises H, $CH_3$, Cl, or

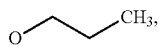

wherein $R_3$ comprises H or $NH_2$; wherein $R_4$ comprises H, $NH_2$, $CH_3$,

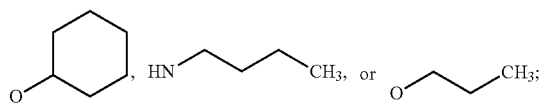

wherein $R_5$ comprises H; and wherein $R_6$ comprises H or $CH_3$, and
wherein the analgesic is present in the pharmaceutical composition in a concentration of from about 50 to about 60 mg per mL, and wherein the anesthetic is present in the pharmaceutical composition in a concentration of from about 10 to about 20 mg per mL.

In one embodiment, $R_1$ of Formula I comprises

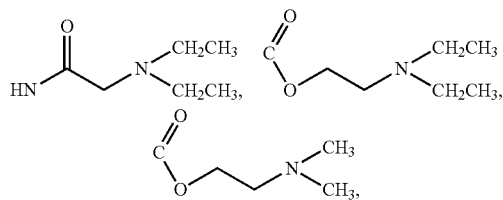

wherein $R_2$ comprises H or $CH_3$; wherein $R_3$ comprises H; wherein $R_4$ comprises H, $NH_2$, or

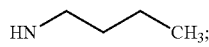

wherein $R_5$ comprises H; and wherein $R_6$ comprises H or $CH_3$.

In some embodiments, the otic pharmaceutical composition further comprises an antibiotic, a vasoconstrictor, glycerin, epinephrine, acetic acid, or a combination thereof. In some embodiments, the anesthetic comprises lidocaine, tetracaine, benzocaine, or a combination thereof. In some embodiments, the anesthetic is not benzocaine. In further embodiments, the anesthetic comprises lidocaine, tetracaine, or a combination thereof.

In one embodiment, the pyrazolone derivative of the otic pharmaceutical composition comprises ampyrone, dipyrone, antipyrine, aminopyrine, or propyphenazone. In some embodiments, the analgesic is antipyrine.

The pharmaceutical compositions may be formulated in a host of ways, including, but not limited to, the following: solutions, foams, gels, creams, pastes, lotions, emulsions, and combinations of the aforementioned.

Furthermore, the present disclosure contemplates that active ingredients of the pharmaceutical composition, such as antipyrine and benzocaine, may be infused into material that is then placed into a patient's ear canal. For instance, cotton gauze material could be composed to contain the present pharmaceutical composition, said gauze providing a convenient application method by which to expose the ear canal to the present pharmaceutical composition.

In one embodiment, an otic pharmaceutical composition is administered to an ear canal of a subject in need of such treatment, wherein the subject is a vertebrate species that includes but is not limited to a human, horse, cow, pig, dog, cat, etc. In some embodiments, the otic pharmaceutical composition comprises a topical anesthetic alone or in combination with other topical anesthetics with or without analgesics. In one embodiment, the analgesic is antipyrine. In another embodiment, the anesthetic is at least one selected from the group consisting of benzocaine, formacaine, cocaine, and cyclomethycaine. In other embodiments, the anesthetic comprises tetracaine and/or lidocaine. In some embodiments, the otic pharmaceutical composition further comprises the presence or absence of epinephrine, suspended in solution of various pharmaceutical carriers. The otic pharmaceutical composition is subsequently administered to the ear canal for the desired effect.

Anatomical Site of Application of the Pharmaceutical Composition

The invention provides for methods for treating a variety of diseases that comprises performing topical auricular anesthesia of the external auditory canal for the purposes of anesthetizing cranial nerves 5, 7, 9, 10, 11, and 12, along with anesthetizing the parasympathetic nervous system, and/or the sympathetic nervous system. In one embodiment, the invention provides for treating a variety of diseases that comprises performing topical auricular anesthesia of the autonomic nervous system. In one embodiment, auricular anesthesia is performed on the trigeminal nerve (cranial nerve 5), the facial nerve (cranial nerve 7), the glossopharyngeal nerve (cranial nerve 9), the vagus nerve (cranial nerve 10), the spinal accessory nerve (cranial nerve 11), the hypoglossal nerve (cranial nerve 12), or a combination thereof. The invention further provides for modulation of the general somatic nervous system and the general visceral nervous system by administering an otic pharmaceutical composition comprising one or more anesthetics (such as lidocaine and/or tetracaine) in solution with a pharmaceutical carrier (such as an excipient) glycerine, and with or without epinephrine. In some embodiments, the otic pharmaceutical composition further comprises an analgesic, such as a pyrazolone derivative. In some embodiments, the pyrazolone derivative is antipyrene.

The present method contemplates applying the disclosed pharmaceutical composition to the ear canal of a patient. It has been found that the ear canal serves as a convenient point in the human anatomy in which to apply the present pharmaceutical composition and achieve disruption of neurological signals along the vagus or other cranial nerves. That is, by placing a pharmaceutical composition, as described herein, into the ear canal of a patient, it has been discovered that the body will absorb the composition and the vagus or other cranial nerve will be "blocked," such that the normal physiological function of the nerve will be altered. The present methodology of utilizing the ear canal as a conduit to anesthetizing the particular nerve does not suffer from the drawbacks present in the prior art.

The present methods of applying a pharmaceutical composition as described are not invasive and do not pose the risks associated with surgical procedures. Furthermore, the present methods do not rely upon inserting artificial devices into the body of patient. It is evident that the present methods represent a significant advancement over the state of the art, as the disclosed non-invasive procedure is able to alter the function of the vagus or other cranial nerve without artificial devices or surgery. The present methods are also economical and would therefore provide access to treatment to the vast majority of a population.

The presently disclosed embodiments of a method of blocking signal transduction upon the vagus nerve will now be further elaborated upon by reference to the following examples. In each of these examples, the disclosed method was able to successfully treat a human disease, or ailment, that was associated with a particular cranial nerve. Without being bound by theory, the methods are also useful to treat a disease or ailment associated with a particular cranial nerve in a variety of vertebrate species including but not limited to horses, cows, pigs, dogs, cats, etc. Conditions treated in the examples disclosed herein were able to be controlled to a clinically effective degree by the disclosed method of performing auricular anesthesia on the vagus or other cranial nerve, or by performing auricular anesthesia of the autonomic nervous system, i.e. referred to as the "Crews Maneuver." In one embodiment, the disease is a neurology-psychiatry-related affliction, an ear-nose-throat (ENT)-related affliction, a GU-related affliction, a gastrointestinal (GI)-related affliction, a cardiac-related affliction, a pulmonary-related affliction, or a metabolic-related affliction. In one embodiment, the neurology-psychiatry-related affliction is at least one selected from the group consisting of: chronic fatigue syndrome, fibromyalgia, epilepsy, Obsessive Compulsive Disorder, panic attack, Post-Traumatic Stress Disorder, Tourette's Syndrome, Focal Dystonia, Tic Doloreaux, Bulimia, Anxiety, Depression, Restless Leg Syndrome, Dysautonomia, Familial Intentional Tremor, Migraine pain, Autism Spectrum Disorder, Anxiety Headache, sleeplessness, Reticular Activating System (RAS) dysregulation, Multiple Sclerosis, Peripheral Neuropathy, Apraxia, Neck and Shoulder Pain, Parkinson's Disease, General Somatic Afferent Pain, General Visceral, Afferent Pain, opiate withdrawal, Dysarthria, ADHD, Nonspecific hand tremor, Stuttering, cerebral palsy, Raynaud's Phenomenon, and excessive sweating. In one embodiment, the General Somatic Afferent Pain comprises Neuromuscular Pain of the neck, back, arms, legs, or shoulders; Joint Pain; Sciatica pain; Arthritis pain; Shingles Pain; Reflex Sympathetic Dystrophy pain; or a combination thereof. In one embodiment, a symptom of opiate withdrawal comprises Generalized Pain, Muscle Aches, Nausea, vomiting, Sweating, Diarrhea, or a combination thereof. In one embodiment, the ear-nose-throat (ENT)-related affliction is at least one selected from the group consisting of: Palatal Myoclonus, Post Tonsillectomy Pain, Pharyngeal Pain, Laryngeal Pain, Neurogenic Cough, Globus Hystericus, Spasmodic Dysphonia, Snoring, Allergic Rhinitis, Chronic Sinusitis, Chronic Nasal Congestion, Allergic Conjunctivitis, Sneezing, Hiccups, Rhinitis, Tinnitus, Dysphagia, ear pain, neck pain, Dry Eye Syndrome, Trigeminal Neuralgia pain, and Temporomandibular Joint Pain. In one embodiment, the Gastroenterology/Urology (GU)-related affliction is at least one selected from the group consisting of: bladder spasm, dysmenorrhea, pelvic pain, Premature Labor, interstitial cystitis, Prostatitis, Eclampsia, pre-eclampsia, HELLP Syndrome, cystitis, Kidney Pain, enuresis, dysuria, dyspareunia, encopresis, heavy flow menstruation, frequent urination, Prolonged Vaginal Bleeding, and decreased renal blood flow. In one embodiment, the gastrointestinal (GI)-related affliction is at least one selected from the group consisting of: irritable bowel syndrome (MS), ulcerative colitis, acid reflux, Gastritis, Gastroenteritis, Hyperemesis Gravidarum, Pediatric Colic, Hepato-Renal Syndrome, Appetite Suppression, Gall Bladder Pain, Chronic constipation, Chronic diarrhea, and Pancreatitis. In one embodiment, the cardiac-related affliction is at least one selected from the group consisting of: Paroxysmal (Lone) (Vagal) Atrial Fibrillation, Orthostatic (Neurogenic) Hypotension, Reflex Asystolic Syncope, Postural Orthostatic Tachycardia Syndrome (POTS), Vasovagal Reflex, cardiac surgery derived cough, heart block, Atrial Contractions, Tachycardia, and Congestive Heart Failure. In one embodiment, the pulmonary-related affliction is at least one selected from the group consisting of: asthma, chronic obstructive pulmonary disease (COPD), bronchitis, cystic fibrosis, and Bronchospasm. In one embodiment, the metabolic-related affliction is at least one selected from the group consisting of: hypertension, diabetes, septic shock, neurogenic shock, hyperglycemia, and hypercholesteremia.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention.

As will be apparent to one of ordinary skill in the art from a reading of this disclosure, the embodiments of the present disclosure can be embodied in forms other than those specifically disclosed above. The particular embodiments described herein are, therefore, to be considered as illustrative and not restrictive. Those skilled in the art will recognize, or be able to ascertain, using no more than routine experimentation, numerous equivalents to the specific embodiments described herein. The scope of the invention is as set forth in the appended claims and equivalents thereof, rather than being limited to the examples contained in the foregoing description.

All publications and other references mentioned herein are incorporated by reference in their entirety, as if each individual publication or reference were specifically and individually indicated to be incorporated by reference. Publications and references cited herein are not admitted to be prior art.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1: Treatment of Post-Tonsillectomy Pharyngeal or Oropharyngeal Pain

Protocol

A test of a preferred embodiment of the present method was conducted to evaluate the efficacy of the method for treating patients suffering from post-tonsillectomy pharyngeal, or oropharyngeal pain.

500 patients that had previously undergone a tonsillectomy were instructed to utilize six drops of a pharmaceutical composition comprising antipyrine ($\approx 54.0$ mg) and benzocaine ($\approx 14.0$ mg), in each ear three times per day, for a duration of ten days after the tonsillectomy.

Results

Out of the 500 patients treated, 495 patients reported significant reduction in pharyngeal and/or oropharyngeal pain.

Example 2: Treatment of Post Adenoidectomy Pharyngeal or Oropharyngeal Pain

Protocol

A test of a preferred embodiment of the present method was conducted to evaluate the efficacy of the method for treating patients suffering from post-adenoidectomy pharyngeal, or oropharyngeal pain.

200 patients that had previously undergone an adenoidectomy were instructed to utilize six drops of a pharmaceutical composition comprising antipyrine ($\approx 54.0$ mg) and benzocaine ($\approx 14.0$ mg), in each ear two times per day, for a duration of seven days after the adenoidectomy.

Results

Out of the 200 patients treated, 200 patients reported significant reduction in pharyngeal and/or oropharyngeal pain.

Example 3: Treatment of Asthma

Protocol

A test of a preferred embodiment of the present method was conducted to evaluate the efficacy of the method for treating patients suffering from chronic asthma and acute asthmatic attack.

10 patients with asthma were instructed to utilize six drops of a pharmaceutical composition comprising antipyrine ($\approx 54.0$ mg) and benzocaine ($\approx 14.0$ mg), in each ear in the morning, for two months.

A patient suffering from a severe acute asthma attack was also treated by immediately filling the patient's ear canal with the aforementioned pharmaceutical composition.

Results

Out of the 10 patients treated, 10 patients reported significant reduction in asthmatic attacks.

Further, the patient suffering from the severe asthma attack experienced a dramatic increase in the amount of oxygen reaching his lungs within 60 minutes of the treatment.

Example 4: Treatment of Obesity (i.e. a Method of Appetite Suppression)

Protocol

A test of a preferred embodiment of the present method was conducted to evaluate the efficacy of the method for treating patients suffering from obesity.

5 overweight patients were instructed to utilize six drops of a pharmaceutical composition comprising antipyrine ($\approx 54.0$ mg) and benzocaine ($\approx 14.0$ mg), in each ear in the morning, for an indefinite period of time.

Results

Out of the 5 patients treated, all 5 patients reported significant reduction in appetite while utilizing the treatment. The significant reduction in appetite led to weight loss.

Example 5: Treatment of Neurogenic Cough

Protocol

A test of a preferred embodiment of the present method was conducted to evaluate the efficacy of the method for treating patients suffering from neurogenic cough.

4 patients suffering from neurogenic cough were instructed to utilize six drops of a pharmaceutical composition comprising antipyrine ($\approx 54.0$ mg) and benzocaine ($\approx 14.0$ mg), in each ear two times per day, for a duration of seven days and then only as needed.

Results

Out of the 4 patients treated, all 4 patients reported significant reduction in cough.

Example 6: Treatment of Globus Hystericus

Protocol

A test of a preferred embodiment of the present method was conducted to evaluate the efficacy of the method for treating patients suffering from globus hystericus.

2 patients suffering from globus hystericus were instructed to utilize six drops of a pharmaceutical composition comprising antipyrine ($\approx 54.0$ mg) and benzocaine ($\approx 14.0$ mg), in each ear one time per day, for an indefinite period of time as needed.

Results

Out of the 2 patients treated, all 2 patients reported significant reduction in throat tightness.

Example 7: Treatment of Spasmodic Dysphonia

Protocol

A test of a preferred embodiment of the present method was conducted to evaluate the efficacy of the method for treating patients suffering from spasmodic dysphonia.

One (1) patient suffering from spasmodic dysphonia was instructed to utilize six drops of a pharmaceutical composition comprising antipyrine mg) and benzocaine mg), in each ear one time per day, for an indefinite period of time as needed.

Results

The patient reported significant reduction in throat hoarseness and vocal cord spasms almost immediately upon using the treatment.

Example 8: Treatment of Laryngeal Pain

Protocol

A test of a preferred embodiment of the present method was conducted to evaluate the efficacy of the method for treating patients suffering from laryngeal pain.

2 patients suffering from laryngeal pain were instructed to utilize six drops of a pharmaceutical composition comprising antipyrine mg) and benzocaine mg), in each ear one time per day, for an indefinite period of time as needed.

Results

Out of the 2 patients treated, all patients reported significant reduction in laryngeal pain.

Example 9: Treatment of Gastroesophageal Reflux Disease

Protocol

A test of a preferred embodiment of the present method was conducted to evaluate the efficacy of the method for treating patients suffering from Gastroesophageal Reflux Disease (GERD).

2 patients suffering from GERD were instructed to utilize six drops of a pharmaceutical composition comprising antipyrine mg) and benzocaine mg), in each ear one time per day, for an indefinite period of time as needed.

Results

Out of the 2 patients treated, all 2 patients reported significant reduction in acid reflux and heartburn.

The results from the aforementioned clinical experiments can be found below in Table 1.

TABLE 1

Clinical Experiments

| Disease Treated | Number of Subjects Treated | Treatment Protocol (1 mL ≈ 15-20 drops) | Amount of Time Treated | Number of Subjects Exhibiting Clinical Improvement in Symptoms | % of Subjects Exhibiting Clinical Improvement in Symptoms |
|---|---|---|---|---|---|
| Post-Tonsillectomy Pharyngeal or Oropharyngeal Pain | 500 | 6 drops per ear 3 times per day | For 10 days post operation | 495 | 99% |
| Post-Adenoidectomy Pharyngeal or Oropharyngeal Pain | 200 | 6 drops per ear 2 times per day | For 7 days post operation | 200 | 100% |
| Asthma | 10 | 6 drops per ear in the morning | For 2 months | 10 | 100% |
| Obesity via Appetite Suppression | 5 | 6 drops per ear in the morning | Daily | 5 | 100% |
| Neurogenic Cough | 4 | 6 drops per ear 2 times per day | 7 days and then as needed | 4 | 100% |
| Globus Hystericus | 2 | 6 drops per ear once a day | As needed | 2 | 100% |
| Spasmodic Dysphonia | 1 | 6 drops per ear once a day | As needed | 1 | 100% |
| Laryngeal Pain | 2 | 6 drops per ear once a day | As needed | 2 | 100% |
| Gastroesophageal Reflux Disease (GERD) | 2 | 6 drops per ear once a day | As needed | 2 | 100% |

Example 10: Treatment of Diseases

Protocol

A test of an embodiment of the present method was conducted to evaluate the efficacy of the method for treating patients suffering from a disease associated with a particular cranial nerve, wherein the disease is a neurology-psychiatry-related affliction, an ear-nose-throat (ENT)-related affliction, a Gastroenterology/Urology (GU)-related affliction, a gastrointestinal (GI)-related affliction, a cardiac-related affliction, a pulmonary-related affliction, or a metabolic-related affliction.

Patients suffering from a neurology-psychiatry-related affliction, an ear-nose-throat (ENT)-related affliction, a GU-related affliction, a gastrointestinal (GI)-related affliction, a cardiac-related affliction, a pulmonary-related affliction, or a metabolic-related affliction were instructed to utilize drops of a pharmaceutical composition comprising antipyrine (≈54.0 mg) and benzocaine (≈14.0 mg) (treatment protocol, "AB" Tmt Protocol) or drops of a pharmaceutical composition comprising lidocaine (≈40.0 mg) and tetracaine (≈5.0 mg) (treatment protocol, "LAT" Tmt Protocol), in one or both ears, at least one time per day (for example, either in the morning or at night), for a period of time as needed (Tmt Time). The LAT otic solution used in the tests comprises 4% Lidocaine, 0.5% Tetracaine, 1/100,000 Epinephrine, and Anhydrous Glycerine. The AB otic solution used in the tests comprises 5.4% Antipyrine, 1.4% Benzocaine, Oxyquinoline Sulfate, and Anhydrous Glycerine.

TABLE 2

Clinical Experiments with Neurology-psychiatry-related afflictions

| Neurology-psychiatry-related affliction | # of Subjects Treated | Tmt Protocol (1 mL ≈ 15-20 drops) | Tmt Time | # of Subjects Exhibiting Clinical Improvement in Symptoms | Improvement in Symptoms reported |
|---|---|---|---|---|---|
| Chronic Fatigue Syndrome | 5 | LAT: 6 drops per ear 1x/day | as needed | 4 | More energy More activity Less fatigue |
|  | 3 | AB: 6 drops per ear 1x/day | 4 wks | 2 | Less muscle and joint pain 70% reduction in symptoms w/both tmts |
| Fibromyalgia (chronic) | 5 | LAT: 6 drops per ear 1x/day | 4 wks | 4 | Less muscle and joint pain w/both tmts |

TABLE 2-continued

Clinical Experiments with Neurology-psychiatry-related afflictions

| Neurology-psychiatry-related affliction | # of Subjects Treated | Tmt Protocol (1 mL ≈ 15-20 drops) | Tmt Time | # of Subjects Exhibiting Clinical Improvement in Symptoms | Improvement in Symptoms reported |
|---|---|---|---|---|---|
| | 3 | AB: 6 drops per ear 1x/day | 4 wks | 2 | |
| Epilepsy (Absence Seizures) | 1 | LAT: 6 drops per ear 1x/day | 4 wks | 1 | less seizures by 90% w/both tmts |
| | 2 | AB: 6 drops per ear 1x/day | 4 wks | 1 | |
| Obsessive Compulsive Disorder | 3 | LAT: 6 drops per ear 1x/day | 4 wks | 3 | less repetitive behavior less vomiting in bulimics |
| Panic Attacks | 4 | LAT: 6 drops per ear 1x/day | 4 wks | 2 | 75% less panic attacks w/both tmts |
| | 4 | AB: 6 drops per ear 1x/day | 4 wks | 2 | |
| Post-Traumatic Stress Disorder | 1 | LAT: 6 drops per ear 1x/day | 4 wks | 1 | Better sleep Less anxiety Less nightmares |
| | 1 | AB: 6 drops per ear 1x/day | 4 wks | 1 | Decrease in startle reflex by >50% w/both tmts |
| Tourette's Syndrome | 1 | LAT: 6 drops per ear 1x/day | 4 wks | 1 | decreased tic activity and movement |
| Focal Dystonia | 1 | LAT: 6 drops per ear 1x/day | 4 wks | 1 | 50% less eye blinking w/both tmts |
| | 1 | AB: 6 drops per ear 1x/day | 4 wks | 1 | |
| Anxiety | 5 | LAT: 6 drops per ear 1x/day | 4 wks | 4 | 70% reduction in nervousness less need for anxiolytics |
| | 3 | AB: 6 drops per ear 1x/day | 4 wks | 2 | w/both tmts |
| Depression | 5 | LAT: 6 drops per ear 1x/day | 4 wks | 4 | Less depression Less fatigue 70% increase in activity |
| | 3 | AB: 6 drops per ear 1x/day | 4 wks | 2 | w/both tmts |
| Restless Leg Syndrome | 5 | LAT: 6 drops per ear 1x/day | 4 wks | 4 | ≥70% reduction in leg movements w/both tmts |
| | 3 | AB: 6 drops per ear 1x/day | 4 wks | 2 | |
| Dysautonomia | 5 | LAT: 6 drops per ear 1x/day | 4 wks | 4 | ≥70% reduction in parasympathetic and sympathetic symptoms |
| | 3 | AB: 6 drops per ear 1x/day | 4 wks | 2 | w/both tmts |
| Familial Tremor | 5 | LAT: 6 drops per ear 1x/day | 4 wks | 5 | ≥70% reduction in hand shaking/tremor w/both tmts |
| | 2 | AB: 6 drops per ear 1x/day | 4 wks | 1 | |
| Migraine pain | 5 | LAT: 6 drops per ear 1x/day | 4 wks | 4 | ≥70% reduction in migraine headaches per month (frequency, duration, and intensity) |
| | 3 | AB: 6 drops per ear 1x/day | 4 wks | 2 | w/both tmts |
| Autism spectrum disorder | 5 | LAT: 6 drops per ear 1x/day | 4 wks | 5 | Less outbursts Calmer Better speech |

TABLE 2-continued

Clinical Experiments with Neurology-psychiatry-related afflictions

| Neurology-psychiatry-related affliction | # of Subjects Treated | Tmt Protocol (1 mL ≈ 15-20 drops) | Tmt Time | # of Subjects Exhibiting Clinical Improvement in Symptoms | Improvement in Symptoms reported |
|---|---|---|---|---|---|
| | 3 | AB: 6 drops per ear 1x/day | 4 wks | 1 | More focused w/both tmts |
| Anxiety Headaches | 5 | LAT: 6 drops per ear 1x/day | 4 wks | 5 | ≥75% reduction in headaches per month (frequency, duration, and intensity) w/both tmts |
| | 5 | AB: 6 drops per ear 1x/day | 4 wks | 2 | |
| Sleeplessness | 5 | LAT: 6 drops per ear 1x/day | 4 wks | 4 | better and continuous sleep |
| Multiple Sclerosis | 1 | LAT: 6 drops per ear 1x/day | 4 wks | 1 | ≥50% reduction in muscle pain more muscle strength w/both tmts |
| | 1 | AB: 6 drops per ear 1x/day | 4 wks | 1 | |
| Peripheral Neuropathy | 5 | LAT: 6 drops per ear 1x/day | 4 wks | 4 | ≥50% reduction in peripheral pain w/both tmts |
| | 5 | AB: 6 drops per ear 1x/day | 4 wks | 4 | |
| Apraxia | 2 | LAT: 6 drops per ear 1x/day | 4 wks | 2 | 50% better speech as noted by parents (better word pronunciation) w/both tmts |
| | 2 | AB: 6 drops per ear 1x/day | 4 wks | 1 | |
| Neck and Shoulder Pain | 5 | LAT: 6 drops per ear 1x/day | 4 wks | 5 | ≥50% reduction in pain w/both tmts |
| | 3 | AB: 6 drops per ear 1x/day | 4 wks | 2 | |
| Parkinson's Disease | 2 | LAT: 6 drops per ear 1x/day | 4 wks | 2 | Less tremors and pain Better Balance w/both tmts |
| | 1 | AB: 6 drops per ear 1x/day | 4 wks | 1 | |
| General Somatic Afferent Pain-Neuromuscular Pain | 4 | LAT: 6 drops per ear 1x/day | 4 wks | 3 | less neck, back, arm, leg, shoulder, and chest pain w/both tmts |
| | 2 | AB: 6 drops per ear 1x/day | 4 wks | 1 | |
| General Somatic Afferent Pain-Joint Pain (nonspecific) | 4 | LAT: 6 drops per ear 1x/day | 4 wks | 3 | ≥50% reduction in pain requiring less pain medications w/both tmts |
| | 3 | AB: 6 drops per ear 1x/day | 4 wks | 2 | |
| General Somatic Afferent Pain-Sciatica pain | 4 | LAT: 6 drops per ear 1x/day | 4 wks | 3 | reduction in pain |
| General Somatic Afferent Pain-Arthritis pain | 4 | LAT: 6 drops per ear 1x/day | 4 wks | 3 | reduction in pain |
| General Somatic Afferent Pain-Shingles Pain | 4 | LAT: 6 drops per ear 1x/day | 4 wks | 3 | reduction in pain |
| General Somatic Afferent Pain-Reflex Sympathetic Dystrophy pain | 3 | LAT: 6 drops per ear 1x/day | 4 wks | 3 | ≥70% reduction in peripheral pain signals less electrical, sharp pain w/both tmts |
| | 1 | AB: 6 drops per ear 1x/day | 4 wks | 1 | |

TABLE 2-continued

Clinical Experiments with Neurology-psychiatry-related afflictions

| Neurology-psychiatry-related affliction | # of Subjects Treated | Tmt Protocol (1 mL ≈ 15-20 drops) | Tmt Time | # of Subjects Exhibiting Clinical Improvement in Symptoms | Improvement in Symptoms reported |
|---|---|---|---|---|---|
| General Visceral Afferent Pain | 5 | LAT: 6 drops per ear 1x/day | 4 wks | 4 | ≥70% reduction in esophageal, stomach, intestinal, bladder, and pelvic pain w/both tmts |
|  | 1 | AB: 6 drops per ear 1x/day | 4 wks | 1 |  |
| Opiate Withdrawal | 5 | LAT: 6 drops per ear 1x/day | 4 wks | 3 | Reduction of Muscle aches, back pains, Nausea, Vomiting, sweating, diarrhea w/both tmts |
|  | 5 | AB: 6 drops per ear 1x/day | 4 wks | 3 |  |
| Dysarthria | 5 | LAT: 6 drops per ear 1x/day | 4 wks | 3 | 50% better intelligible speech w/both tmts |
|  | 1 | AB: 6 drops per ear 1x/day | 4 wks | 1 |  |
| Attention Deficit Hyperactivity Disorder (ADHD) | 5 | LAT: 6 drops per ear 1x/day | 4 wks | 4 | Calmer More focused Less frequent long-lasting emotional outbursts w/both tmts |
|  | 3 | AB: 6 drops per ear 1x/day | 4 wks | 2 |  |
| Nonspecific hand tremors | 4 | LAT: 6 drops per ear 1x/day | 4 wks | 4 | 50% less tremors w/both tmts |
|  | 2 | AB: 6 drops per ear 1x/day | 4 wks | 2 |  |
| Stuttering | 2 | LAT: 6 drops per ear 1x/day | 4 wks | 2 | 50% less stuttering w/both tmts |
|  | 2 | AB: 6 drops per ear 1x/day | 4 wks | 2 |  |
| Cerebral Palsy | 1 | LAT: 6 drops per ear 1x/day | 4 wks | 1 | Neuromuscular modulation enhanced better balance walks straighter speech more intelligible w/both tmts |
|  | 1 | AB: 6 drops per ear 1x/day | 4 wks | 1 |  |
| Raynaud's Phenomenon | 2 | LAT: 6 drops per ear 1x/day | 4 wks | 2 | Better circulation 50% less discoloration 50% less cyanosis Better warmth to hand w/both tmts |
|  | 1 | AB: 6 drops per ear 1x/day | 4 wks | 1 |  |
| Excessive Sweating | 3 | LAT: 6 drops per ear 1x/day | 4 wks | 2 | ≥70% reduction in perspiration w/both tmts |
|  | 2 | AB: 6 drops per ear 1x/day | 4 wks | 1 |  |

TABLE 3

Clinical Experiments with ear-nose-throat (ENT)-related afflictions.

| ENT-related affliction | # of Subjects Treated | Tmt Protocol (1 mL ≈ 15-20 drops) | Tmt Time | # of Subjects Exhibiting Clinical Improvement in Symptoms | % of Subjects Exhibiting Clinical Improvement in Symptoms |
|---|---|---|---|---|---|
| Post Tonsillectomy Pain | 50 | LAT: 6 drops per ear 1x/day | 4 wks | 50 | ≥50% reduction in pain Reduction of pain |

TABLE 3-continued

Clinical Experiments with ear-nose-throat (ENT)-related afflictions.

| ENT-related affliction | # of Subjects Treated | Tmt Protocol (1 mL ≈ 15-20 drops) | Tmt Time | # of Subjects Exhibiting Clinical Improvement in Symptoms | % of Subjects Exhibiting Clinical Improvement in Symptoms |
|---|---|---|---|---|---|
| | 50 | AB: 6 drops per ear 1x/day | 4 wks | 50 | medications w/both tmts |
| Pharyngeal Pain | 50 | LAT: 6 drops per ear 1x/day | 4 wks | 50 | ≥70% reduction in throat pain w/both tmts |
| | 50 | AB: 6 drops per ear 1x/day | 4 wks | 50 | |
| Laryngeal Pain | 5 | LAT: 6 drops per ear 1x/day | 4 wks | 5 | ≥50% reduction in laryngeal pain w/both tmts |
| | 5 | AB: 6 drops per ear 1x/day | 4 wks | 5 | |
| Neurogenic Cough | 5 | LAT: 6 drops per ear 1x/day | 4 wks | 5 | ≥70% reduction in cough w/both tmts |
| | 5 | AB: 6 drops per ear 1x/day | 4 wks | 5 | |
| Globus Hystericus | 5 | LAT: 6 drops per ear 1x/day | 4 wks | 5 | ≥70% reduction in tightness of throat fullness w/both tmts |
| | 2 | AB: 6 drops per ear 1x/day | 4 wks | 2 | |
| Spasmodic Dysphonia | 5 | LAT: 6 drops per ear 1x/day | 4 wks | 4 | ≥70% reduction in dysphonia w/both tmts |
| | 1 | AB: 6 drops per ear 1x/day | 4 wks | 1 | |
| Snoring | 5 | LAT: 6 drops per ear 1x/day | 4 wks | 4 | ≥50% reduction in snoring w/both tmts |
| | 5 | AB: 6 drops per ear 1x/day | 4 wks | 4 | |
| Allergic Rhinitis | 5 | LAT: 6 drops per ear 1x/day | 4 wks | 4 | ≥50% reduction in sneezing, sniffling, and congestion w/both tmts |
| | 5 | AB: 6 drops per ear 1x/day | 4 wks | 4 | |
| Chronic Sinusitis | 5 | LAT: 6 drops per ear 1x/day | 4 wks | 4 | ≥50% reduction in mucous discharge, sneezing, and congestion w/both tmts |
| | 5 | AB: 6 drops per ear 1x/day | 4 wks | 4 | |
| Chronic Nasal Congestion | 5 | LAT: 6 drops per ear 1x/day | 4 wks | 4 | ≥50% reduction in airway obstruction w/both tmts |
| | 5 | AB: 6 drops per ear 1x/day | 4 wks | 4 | |
| Allergic Conjunctivitis | 5 | LAT: 6 drops per ear 1x/day | 4 wks | 5 | ≥50% reduction in burning, redness, and tearing w/both tmts |
| | 5 | AB: 6 drops per ear 1x/day | 4 wks | 5 | |
| Sneezing | 5 | LAT: 6 drops per ear 1x/day | 4 wks | 5 | ≥70% reduction in sneezing w/both tmts |
| | 5 | AB: 6 drops per ear 1x/day | 4 wks | 5 | |
| Hiccups (acute and chronic) | 5 | LAT: 6 drops per ear 1x/day | 4 wks | 4 | ≥70% reduction in hiccups w/both tmts |

TABLE 3-continued

Clinical Experiments with ear-nose-throat (ENT)-related afflictions.

| ENT-related affliction | # of Subjects Treated | Tmt Protocol (1 mL ≈ 15-20 drops) | Tmt Time | # of Subjects Exhibiting Clinical Improvement in Symptoms | % of Subjects Exhibiting Clinical Improvement in Symptoms |
|---|---|---|---|---|---|
| Rhinitis | 5 | AB: 6 drops per ear 1x/day | 4 wks | 4 | |
| | 5 | LAT: 6 drops per ear 1x/day | 4 wks | 4 | reduction of congestion, runny nose, and sneezing w/both tmts |
| Tinnitus | 5 | AB: 6 drops per ear 1x/day | 4 wks | 4 | |
| | 5 | LAT: 6 drops per ear 1x/day | 4 wks | 1 | Noticeable 50% reduction in ringing in ear |
| Dysphagia | 5 | LAT: 6 drops per ear 1x/day | 4 wks | 4 | 50% easier to swallow w/both tmts |
| | 3 | AB: 6 drops per ear 1x/day | 4 wks | 2 | |
| Ear Pain (acute and chronic) | 5 | LAT: 6 drops per ear 1x/day | 4 wks | 2 | 70% less ear pain w/both tmts |
| | 8 | AB: 6 drops per ear 1x/day | 4 wks | 5 | |
| Neck Pain | 3 | LAT: 6 drops per ear 1x/day | 4 wks | 2 | 50% less neck pain w/both tmts |
| | 3 | AB: 6 drops per ear 1x/day | 4 wks | 2 | |
| Dry Eye Syndrome | 4 | LAT: 6 drops per ear 1x/day | 4 wks | 3 | less redness, matting, and dry eyes w/both tmts |
| | 2 | AB: 6 drops per ear 1x/day | 4 wks | 1 | |
| Trigeminal Neuralgia Pain | 5 | LAT: 6 drops per ear 1x/day | 4 wks | 4 | 50% less facial pain w/both tmts |
| | 3 | AB: 6 drops per ear 1x/day | 4 wks | 2 | |
| Temporomandibular Joint Pain | 5 | LAT: 6 drops per ear 1x/day | 4 wks | 4 | ≥70% reduction of jaw pain w/both tmts |
| | 3 | AB: 6 drops per ear 1x/day | 4 wks | 2 | |

TABLE 4

Clinical Experiments with Gastroenterology/Urology (GU)-related afflictions

| GU-related affliction | # of Subjects Treated | Tmt Protocol (1 mL ≈ 15-20 drops) | Tmt Time | # of Subjects Exhibiting Clinical Improvement in Symptoms | % of Subjects Exhibiting Clinical Improvement in Symptoms |
|---|---|---|---|---|---|
| Overactive bladder | 5 | LAT: 6 drops per ear 1x/day | 4 wks | 5 | ≥50% reduction of urination frequency and urgency, and nocturia decreased bladder spasm w/both tmts |
| | 3 | AB: 6 drops per ear 1x/day | 4 wks | 2 | |

TABLE 4-continued

Clinical Experiments with Gastroenterology/Urology (GU)-related afflictions

| GU-related affliction | # of Subjects Treated | Tmt Protocol (1 mL ≈ 15-20 drops) | Tmt Time | # of Subjects Exhibiting Clinical Improvement in Symptoms | % of Subjects Exhibiting Clinical Improvement in Symptoms |
|---|---|---|---|---|---|
| Interstitial Cystitis | 2 | LAT: 6 drops per ear 1x/day | 4 wks | 2 | ≥50% reduction of burning, dysuria, and pressure |
|  | 1 | AB: 6 drops per ear 1x/day | 4 wks | 1 | ≥90% reduction in pain during urination w/both tmts |
| Dysmenorrhea | 5 | LAT: 6 drops per ear 1x/day | 4 wks | 5 | ≥50% reduction of menorrhea pain w/both tmts |
|  | 3 | AB: 6 drops per ear 1x/day | 4 wks | 2 |  |
| Pelvic Pain | 5 | LAT: 6 drops per ear 1x/day | 4 wks | 5 | ≥50% reduction of pelvic pain from infection, surgery or ovaries, and fibroids w/both tmts |
|  | 3 | AB: 6 drops per ear 1x/day | 4 wks | 2 |  |
| Chronic Prostatitis Pain | 1 | LAT: 6 drops per ear 1x/day | 4 wks | 1 | ≥50% reduction in pain and pressure w/both tmts |
|  | 1 | AB: 6 drops per ear 1x/day | 4 wks | 1 |  |
| eclampsia |  | LAT: 6 drops per ear 1x/day | 4 wks |  | expect to see Reduction of rapid weight gain from body fluids, abdominal pain, hpt, and urine output, nausea and vomiting, blurred vision w/both tmts |
|  |  | AB: 6 drops per ear 1x/day | 4 wks |  |  |
| Preeclampsia |  | LAT: 6 drops per ear 1x/day | 4 wks |  | expect to see Reduction of HPT, headaches, Nausea and Vomiting w/both tmts |
|  |  | AB: 6 drops per ear 1x/day | 4 wks |  |  |
| HELLP Syndrome |  | LAT: 6 drops per ear 1x/day | 4 wks |  | expect to see Reduction of HPT, abdominal pain, headaches, nausea and vomiting, shoulder pain, and swelling w/both tmts |
|  |  | AB: 6 drops per ear 1x/day | 4 wks |  |  |
| Cystitis Pain | 5 | LAT: 6 drops per ear 1x/day | 4 wks | 5 | ≥50% reduction in pain w/both tmts |
|  | 1 | AB: 6 drops per ear 1x/day | 4 wks | 1 |  |
| Kidney Pain (from stone, infection, tumor) | 2 | LAT: 6 drops per ear 1x/day | 4 wks | 2 | ≥50% reduction in pain from stone, infection, tumor, etc w/both tmts |
|  | 1 | AB: 6 drops per ear 1x/day | 4 wks | 1 |  |
| Enuresis | 5 | LAT: 6 drops per ear 1x/day | 4 wks | 5 | ≥50% reduction in bed wetting w/both tmts |
|  | 3 | AB: 6 drops per ear 1x/day | 4 wks | 3 |  |
| Dysuria | 5 | LAT: 6 drops per ear 1x/day | 4 wks | 5 | ≥50% reduction in pain with urination (e.g., bladder infection) w/both tmts |
|  | 2 | AB: 6 drops per ear 1x/day | 4 wks | 2 |  |

TABLE 4-continued

Clinical Experiments with Gastroenterology/Urology (GU)-related afflictions

| GU-related affliction | # of Subjects Treated | Tmt Protocol (1 mL ≈ 15-20 drops) | Tmt Time | # of Subjects Exhibiting Clinical Improvement in Symptoms | % of Subjects Exhibiting Clinical Improvement in Symptoms |
|---|---|---|---|---|---|
| Dyspareunia | 5 | LAT: 6 drops per ear 1x/day | 4 wks | 4 | ≥70% reduction in painful intercourse w/both tmts |
| | 3 | AB: 6 drops per ear 1x/day | 4 wks | 2 | |
| Encopresis | 1 | LAT: 6 drops per ear 1x/day | 4 wks | 1 | ≥75% reduction in episodes of defecation in clothing in children older than 3 w/both tmts |
| | 2 | AB: 6 drops per ear 1x/day | 4 wks | 2 | |
| Menorrhagia (Heavy Flow Periods) | 5 | LAT: 6 drops per ear 1x/day | 4 wks | 5 | ≥75% reduction in flow and all had decreased number of days (i.e. 2 days) w/both tmts |
| | 3 | AB: 6 drops per ear 1x/day | 4 wks | 2 | |
| Frequent Urination | 5 | LAT: 6 drops per ear 1x/day | 4 wks | 5 | ≥50% reduction in frequency (daily and nightly) w/both tmts |
| | 3 | AB: 6 drops per ear 1x/day | 4 wks | 2 | |
| Menometrorrhagia (Prolonged Vaginal Bleeding) | 4 | LAT: 6 drops per ear 1x/day | 4 wks | 4 | ≥50% reduction in bleeding from cycle period reduced by at least 2 days w/both treatments |
| | 2 | AB: 6 drops per ear 1x/day | 4 wks | 2 | |

TABLE 5

Clinical Experiments with Gastrointestinal (GI)-related afflictions

| GI-related affliction | # of Subjects Treated | Tmt Protocol (1 mL ≈ 15-20 drops) | Tmt Time | # of Subjects Exhibiting Clinical Improvement in Symptoms | % of Subjects Exhibiting Clinical Improvement in Symptoms |
|---|---|---|---|---|---|
| Irritable Bowel Syndrome | 5 | LAT: 6 drops per ear 1x/day | 4 wks | 5 | ≥50% reduction in diarrhea and constipation |
| | 3 | AB: 6 drops per ear 1x/day | 4 wks | 2 | —w/both treatments |
| Ulcerative Colitis | 2 | LAT: 6 drops per ear 1x/day | 4 wks | 2 | ≥50% reduction in pain, diarrhea, cramping, rectal bleeding, and joint pain |
| | 1 | AB: 6 drops per ear 1x/day | 4 wks | 1 | —w/both treatments |
| Gastroesophageal Reflux (Acid Reflux) | 5 | LAT: 6 drops per ear 1x/day | 4 wks | 5 | ≥50% reduction in bloating, gas, heartburn, and pain |
| | 5 | AB: 6 drops per ear 1x/day | 4 wks | 2 | —w/both treatments |
| Gastritis Pain | 5 | LAT: 6 drops per ear 1x/day | 4 wks | 5 | ≥50% reduction in stomach pain and burning |
| | 3 | AB: 6 drops per ear 1x/day | 4 wks | 2 | —w/both treatments |
| Gastroenteritis | 1 | LAT: 6 drops per | 4 wks | 1 | ≥50% reduction in nausea, vomiting, |

TABLE 5-continued

Clinical Experiments with Gastrointestinal (GI)-related afflictions

| GI-related affliction | # of Subjects Treated | Tmt Protocol (1 mL ≈ 15-20 drops) | Tmt Time | # of Subjects Exhibiting Clinical Improvement in Symptoms | % of Subjects Exhibiting Clinical Improvement in Symptoms |
|---|---|---|---|---|---|
| | | ear 1x/day | | | diarrhea, abdominal cramping |
| | 1 | AB: 6 drops per ear 1 x/day | 4 wks | 1 | ≥75% reduction in nausea and vomiting, abdominal cramping, diarrhea |
| Hyperemesis Gravidarum | 1 | LAT: 6 drops per ear 1 x/day | 4 wks | 1 | 25% reduction in nausea and vomiting |
| Pediatric Colic | 1 | LAT: 6 drops per ear 1x/day | 4 wks | 1 | ≥50% reduction in cramp pain and bowel movements |
| | 1 | AB: 6 drops per ear 1 x/day | 4 wks | 1 | —w/both treatments |
| Appetite Suppression | 5 | LAT: 6 drops per ear 1 x/day | 4 wks | 4 | at least 4 lb. weight loss per month less snacking decreased meal size intake |
| | 3 | AB: 6 drops per ear 1x/day | 4 wks | 2 | —w/both treatments |
| Gall Bladder Pain | 2 | LAT: 6 drops per ear 1x/day | 4 wks | 2 | ≥50% reduction in pain |
| | 2 | AB: 6 drops per ear 1x/day | 4 wks | 2 | —w/both treatments |
| Chronic constipation | 5 | LAT: 6 drops per ear 1x/day | 4 wks | 4 | At least 50% more bowel movements per week |
| | 3 | AB: 6 drops per ear 1x/day | 4 wks | 2 | —w/both treatments |
| Chronic diarrhea | 5 | LAT 6 drops per ear 1x/day | 4 wks | 4 | At least 50% less episodes of diarrhea |
| | 3 | AB: 6 drops per ear 1x/day | 4 wks | 2 | —w/both treatments |
| Pancreatitis pain | 4 | LAT: 6 drops per ear 1x/day | 4 wks | 3 | ≥50% reduction in abdominal pain |
| | 2 | AB: 6 drops per ear 1x/day | 4 wks | 1 | —w/both treatments |

TABLE 6

Clinical Experiments with Cardiac-related afflictions

| Cardiac-related affliction | # of Subjects Treated | Tmt Protocol (1 mL ≈ 15-20 drops) | Tmt Time | # of Subjects Exhibiting Clinical Improvement in Symptoms | % of Subjects Exhibiting Clinical Improvement in Symptoms |
|---|---|---|---|---|---|
| Paroxysmal, lone, vagal mediated atrial fibrillation | 1 | LAT: 6 drops per ear 1x/day | 4 wks | 1 | 50% less atrial fibrillation |
| Orthostatic (Neurogenic) Hypotension | 2 | LAT: 6 drops per ear 1x/day | 4 wks | 2 | 70% less episodes of drops of blood pressure |
| | 1 | AB: 6 drops per ear 1x/day | 4 wks | 1 | —w/both treatments |
| Reflex Asystolic Syncope | 1 | LAT: 6 drops per ear 1x/day | 4 wks | 1 | decreased seizures and spasms |
| Postural Orthostatic Tachycardia | 2 | LAT: 6 drops per ear | 4 wks | 2 | No drop in blood pressure No increase |

TABLE 6-continued

Clinical Experiments with Cardiac-related afflictions

| Cardiac-related affliction | # of Subjects Treated | Tmt Protocol (1 mL ≈ 15-20 drops) | Tmt Time | # of Subjects Exhibiting Clinical Improvement in Symptoms | % of Subjects Exhibiting Clinical Improvement in Symptoms |
|---|---|---|---|---|---|
| Syndrome (POTS) | 2 | 1x/day AB: 6 drops per ear 1x/day | 4 wks | 2 | in heart rate —w/both treatments |
| Vasovagal Reflex | 5 | LAT: 6 drops per ear 1x/day | 4 wks | 5 | 100% reduction in vasovagal reflex syncope |
|  | 5 | AB: 6 drops per ear 1x/day | 4 wks | 5 | —w/both treatments |
| Cough from cardiac surgery | 1 | LAT: 6 drops per ear 1x/day | 4 wks | 1 | decreased coughing incidents |
| Premature Atrial Contractions | 3 | LAT: 6 drops per ear 1x/day | 4 wks | 3 | normalization of heartbeats |
| Supra-ventricular Tachycardia | 3 | LAT: 6 drops per ear 1x/day | 4 wks | 3 | Decreased palpitations, chest discomfort, and lightheadedness |

TABLE 8

Clinical Experiments with Pulmonary-related afflictions

| Pulmonary-related affliction | # of Subjects Treated | Tmt Protocol (1 mL ≈ 15-20 drops) | Tmt Time | # of Subjects Exhibiting Clinical Improvement in Symptoms | % of Subjects Exhibiting Clinical Improvement in Symptoms |
|---|---|---|---|---|---|
| Asthma | 100 | LAT: 6 drops per ear 1x/day | 4 wks | 100 | Reduced cough Reduce inhaler usage |
|  | 100 | AB: 6 drops per ear 1x/day | 4 wks | 100 | —w/both treatments |
| COPD | 2 | LAT: 6 drops per ear 1x/day | 4 wks | 2 | Reduced cough Reduced chest pressure Decreased shortness of breath |
|  | 2 | AB: 6 drops per ear 1x/day | 4 wks | 2 | —w/both treatments |
| Congestive Heart Failure (CHF) |  | LAT: 6 drops per ear 1x/day AB: 6 drops per ear 1x/day | 4 wks 4 wks |  | Expect to see a decrease in coughing and wheezing; decreased water retention; and decreased dizziness and fatigue |
| Chronic Bronchitis symptoms | 5 | LAT: 6 drops per ear 1x/day | 4 wks | 5 | Decreased coughing and reduction of mucous Less chest tightness |
|  | 5 | AB: 6 drops per ear 1x/day | 4 wks | 5 | —w/both treatments |
| Asthmatic Bronchitis symptoms | 5 | LAT: 6 drops per ear 1x/day | 4 wks | 5 | Decreased coughing and reduction of mucous |
|  | 1 | AB: 6 drops per ear 1x/day | 4 wks | 1 | —w/both treatments |
| Cystic Fibrosis | 1 | LAT: 6 drops per ear 1x/day | 4 wks | 1 | Better breathing capability |

TABLE 7

Clinical Experiments with Metabolism-related afflictions

| Metabolism-related affliction | # of Subjects Treated | Tmt Protocol (1 mL ≈ 15-20 drops) | Tmt Time | # of Subjects Exhibiting Clinical Improvement in Symptoms | % of Subjects Exhibiting Clinical Improvement in Symptoms |
|---|---|---|---|---|---|
| Hypertension | 5 | LAT: 6 drops per ear 1x/day | 4 wks | 4 | 20% reduction in systolic pressure 10% reduction in diastolic pressure |
|  | 5 | AB: 6 drops per ear 1x/day | 4 wks | 4 | —w/both treatments |
| Diabetes | 5 | LAT: 6 drops per ear 1x/day | 4 wks | 4 | 20% reduction in a.m. fasting, less hunger |
|  | 5 | AB: 6 drops per ear 1x/day | 4 wks | 4 | —w/both treatments |
| Hyperglycemia | 5 | LAT: 6 drops per ear 1x/day | 4 wks | 4 | reduction in serum glucose levels to desired target |
| Hypercholesteremia | 5 | LAT: 6 drops per ear 1x/day | 4 wks | 3 | reduction in serum cholesterol levels to desired target |

The diseases that are treatable by the disclosed methodology are numerous. Any disease that is associated with an organ or bodily tissue that is innervated by the particular nerve could potentially be treated by the present methods. Particular mention of the following diseases treatable by the present methods is made: asthma, neurogenic cough, globus hystericus, spasmodic dysphonia, gastroesophageal reflux disease, and obesity. The present methods are also suitable for treating post-tonsillectomy or post-adenoidectomy pharyngeal pain, or oropharyngeal pain.

In yet other embodiments, the diseases treatable by the disclosed methodology include, but are not limited to: cardiac diseases, paroxysmal (lone) (vagal) atrial fibrillation, reflex systolic syncope, postural orthostatic tachycardia syndrome (POTS), excessive gag reflex, esophageal dysphagia, vomiting, nausea, odynophagia, esophageal pain, esophageal neuralgia, gastritis, dyspepsia, gall bladder disease, colecistitis pain, abdominal pain, esophageal motility disorder or esophageal dysmotility, spastic colon, pancreatic pain or spasms, pediatric colic, rectal spasms and pain, bladder spasm (overactive bladder), interstitial cystitis, dysmenorrhea, premature labor, pelvic pain, chronic pelvic pain, chronic prostatitis pain, eclampsia, preeclampsia, HELLP syndrome, cystitis pain, irritable bowel syndrome, Cohn's disease, ulcerative colitis, reflux disease, gastritis, gastroenteritis symptoms, hyperemesis gravidarum, pediatric colic, hepato-renal syndrome, appetite suppression, gall bladder pain, inflammation of the esophagus, inflammation of the stomach, inflammation of the colon, kidney pain (from stone, infection, or tumor), enuresis, dysuria, dyspareunia, encopresis, heavy flow periods, frequent urination, prolonged vaginal bleeding, inhibit erections, prevention of premature ejaculation, inhibit excessive sweating, ureteral spasms, menstrual cramps, uterine spasms, ovarian pain and spasms, fallopian tube pain and spasms, pediatric asthma, adult asthma, chronic obstructive pulmonary disease (COPD), bronchial mucus, acute bronchitis, asthmatic bronchitis, chronic bronchitis, bronchospasm, cystic fibrosis, inflammation of the lung, emphysema, pleuritic chest pain, intercostal muscle pain, nerve pain, bronchospasm secondary to intubation and extubation, angina pectoris, cardiac vagal blockage, vasovagal reflex blockage, bradycardia, hypotension, orthostatic hypotension, hypertension, diabetes, shock, septic shock, reduction of blood sugar, inflammation of the pancreas, syncope secondary to vagal or cardiac reasons, vasovagal syncope, bradyarrhythmias, vasodilation of the skin, neuralgia, laryngospasm, acute laryngitis, laryngeal pain, chronic laryngitis, post extubation and intubation laryngospasms, palatal myoclonus, post-tonsillectomy pain, snoring, allergic rhinitis, vasomotor rhinitis, inflammatory polyposis (nasal), chronic sinusitis, chronic nasal congestion, allergic conjunctivitis, sneezing, hiccups, rhinitis, tinnitus, dysphagia, croup, chronic fatigue syndrome, fibromyalgia (chronic), epilepsy, obsessive compulsive disorder, panic attacks, post-traumatic stress disorder, Tourette's syndrome, focal dystonia, tic doloreaux, bulimia, anxiety, depression, restless leg syndrome, dysautonomia, familial intentional tremor, migraines, autism spectrum, anxiety headaches, insomnia, multiple sclerosis, modulation of the reticular activating system, peripheral neuropathy, apraxia, neck and shoulder pain, and Parkinson's disease.

In particular, improvement was reported in over half of the patients treated in accordance with the above methods, where there were minimum of 5 patients treated for symptoms or conditions associated with the following diseases or disorders, vasovagal reflex blockage, chronic bronchitis, asthmatic bronchitis, hypotension, hypertension, diabetes, bladder spasm, dysmenorrhea, pelvic pain, cystitis pain, enuresis, dysuria, dyspareunia, heavy menstrual flow periods, frequent urination, spasmodic dysphonia, snoring, allergic rhinitis, vasomotor rhinitis, chronic sinusitis, chronic nasal congestion, allergic conjunctivitis, sneezing, hiccups, rhinitis, dysphagia, irritable bowel syndrome, gastritis, appetite suppression, chronic fatigue syndrome, fibromyalgia, anxiety, depression, restless leg syndrome, familial intentional tremor, migraines, autism spectrum, anxiety headaches, insomnia, sleep disorders, apraxia, and neck and shoulder pain. Similar positive results (i.e., positive results reported for all or more than half of all patients treated) also were seen with the other listed diseases or closely-related diseases.

While the methods for treating various diseases associated with the vagus and other cranial nerves have been described in the application in connection with various embodiments, the scope of the methods is not intended to be limited to the particular embodiments so disclosed. But on the contrary, the methods are intended to cover such alternatives, modifications, and equivalents, as may be included within the scope and spirit of the below claims.

Example 11—Treatment of Diseases

Embodiments of the invention comprise modulation of the general somatic afferent nerves and general visceral afferent nerves, by administering one or more anesthetic(s), (for example, either alone or in combination, such as Lidocaine or Bupivicaine) in solution with a carrier, such as an excipient, Polyetheylene Glycol. "Modulation" can refer to the ability of the compounds and/or compositions described herein to either enhance (i.e., stimulate) or inhibit (i.e., block) the activity of nerves, such as one or more of cranial nerves, general somatic afferent fibers, general visceral afferent fibers, and the like. For example, the general visceral afferent fibers (GVA) conduct sensory impulses (usually pain or reflex sensations) from the internal organs, glands, and blood vessels to the central nervous system. They are considered to be part of the autonomic nervous system. Embodiments described herein can modulate the general visceral afferent fibers, such as those of the vagus nerve.

The invention further provides for the modulation of the sympathetic and parasympathetic nervous systems, by auricular anesthesia to auricular branches of the vagus, glossopharyngeal, and facial nerves and their connections to the sympathetic ganglion. Anesthesia to the ganglion of cranial nerves 5, 7, 9 and 10, and the sympathetic nervous system results in their respective downward modulation. Overactive sympathetic and parasympathetic nervous systems are clearly implicated in the development and metastasis of certain types of malignancies, namely Prostate Cancer, Ovarian Cancer, Breast Cancer, and Lymphoblastic Leukemia.

Embodiments of the invention comprise treating, preventing, or providing symptomatic relief of infection-related afflictions. The term "infection-related affliction" can refer to an affliction that comprises or results from the invasion of a subject's body and/or body tissue by microorganisms, their multiplication, and the reaction of the subject's immune system to the microorganism. Non-limiting examples of infections as described herein comprise those of the Herpes Simplex virus (HSV type 1 or HSV type 2, for example) and the Varicella-zoster virus (VZV).

Embodiments of the invention comprise treating, preventing, or providing symptomatic relief of skin-related afflictions. The term "skin-related affliction" can refer to an affliction that comprises or affects the integumentary system which covers the entire surface of the body and is composed of skin, hair, nails, and related muscles and glands. Skin-related afflictions can be temporary or permanent. Non-limiting examples of skin conditions comprise facial flushing (such as Hot Flashes), facial blushing, Alopecia Areata, Atopic Dematitis, Chronic Eczema, Acne Vulgaris, Oily Skin, Rosacea, or Morgellons Disease.

Embodiments of the invention comprise treating, preventing, or providing symptomatic relief of cell proliferation-related afflictions. The term "cell proliferation-related affliction" can refer to an affliction that comprises or results from the uncontrollable proliferation of cells within a subject's tissues and the reaction of the subject's immune system to the cell proliferation and/or growth. Non-limiting examples of cell-proliferation related conditions comprise cancers (e.g., solid tumors and liquid cancers) and mastocytosis.

Embodiments of the invention comprise treating, preventing, or providing symptomatic relief of blood flow-related afflictions. The term "blood flow-related affliction" can refer to an affliction that is characterized by alterations in the flow of blood through a subject's vascular system and/or alters the flow of blood through a subject's vascular system. For example, a blood flow-related affliction can result in an increase in the flow of blood through a subject's vascular system. As another example, a blood flow-related affliction can result in a decrease in the flow of blood through a subject's vascular system. Non-limiting examples of blood flow-related afflictions comprise erectile dysfunction, sickle cell disease, or wound healing.

A test of an embodiment of the present method was conducted to evaluate the efficacy of the method for treating patients suffering from an infection-related affliction, cardiac-related afflictions, metabolism-related afflictions, gastroenterology/urology (GU)-related afflictions, skin-related afflictions, neurology-psychiatry-related, cell proliferation-related afflictions, and blood flow-related afflictions. Subjects suffering from such afflictions were instructed to utilize drops of a pharmaceutical composition comprising lidocaine (4%) and bupivacaine (2%), in one or both ears, at least one time per day (for example, either in the morning or at night), for a period of time as needed (Tmt Time).

TABLE 9

Clinical Experiments with Infection-related afflictions

| Infection-related afflictions | # of Subjects Treated | Tmt Protocol (XYZ) | Tmt Time | # of Subjects Exhibiting Clinical Improvement in Symptoms | Clinical Improvement |
|---|---|---|---|---|---|
| Herpes Simplex 1 | 1 | 6 drops per ear 1x/day | at least 2 weeks | 1 | Prevent the emergence of herpes cold sores |
| | 1 | 4% lidocaine; | | 1 | Shorten the course of herpes cold sores |
| | 1 | 2% Bupivacaine | | 1 | Reduction in pain of herpes cold sores |
| Herpes Simplex 2 | | 6 drops per ear 1x/day | at least 2 weeks | | Prevent the emergence of herpes cold sores |
| | | 4% lidocaine; | | | Shorten the course of herpes cold sores |
| | | 2% Bupivacaine | | | Reduction in pain of herpes cold sores |
| Varicella Zoster | 1 | 6 drops per ear 1x/day | at least 2 weeks | 1 | Prevent the emergence of Varicella infection |
| | 1 | 4% lidocaine; Bupivacaine | | 1 | Shorten the course of Varicella infection |

TABLE 9-continued

Clinical Experiments with Infection-related afflictions

| Infection-related afflictions | # of Subjects Treated | Tmt Protocol (XYZ) | Tmt Time | # of Subjects Exhibiting Clinical Improvement in Symptoms | Clinical Improvement |
|---|---|---|---|---|---|
| | 1 | 2% | | 1 | Reduction in pain of Varicella infection |

TABLE 10

Clinical Experiments with Cardiac-related afflictions

| Cardiac-related afflictions | # of Subjects Treated | Tmt Protocol (XYZ) | Tmt Time | # of Subjects Exhibiting Clinical Improvement in Symptoms | Clinical Improvement |
|---|---|---|---|---|---|
| premature atrial contraction and atrial tachycardia | 10 | 6 drops per ear 1x/day 4% lidocaine; 2% Bupivacaine | at least 2 weeks | 9 | Prevent the development of affliction |

TABLE 11

Clinical Experiments with Metabolism-related afflictions

| Metabolism-related affliction | # of Subjects Treated | Tmt Protocol (XYZ) | Tmt Time | # of Subjects Exhibiting Clinical Improvement in Symptoms | Clinical Improvement |
|---|---|---|---|---|---|
| Insulin Resistance | 10 | 6 drops per ear 1x/day 4% lidocaine; 2% Bupivacaine | at least 2 weeks | 9 | |

TABLE 12

Clinical Experiment with Gastroenterology/Urology (GU)-related afflictions

| Gastroenterology/Urology (GU)-related afflictions | # of Subjects Treated | Tmt Protocol (XYZ) | Tmt Time | # of Subjects Exhibiting Clinical Improvement in Symptoms | Clinical Improvement |
|---|---|---|---|---|---|
| Chronic Renal Failure | 3 | 6 drops per ear 1x/day 4% lidocaine; 2% Bupivacaine | at least 2 weeks | 3 | Increased blood flow |

TABLE 13

Clinical Experiment with Skin-related afflictions

| Skin-related affliction | # of Subjects Treated | Tmt Protocol (XYZ) | Tmt Time | # of Subjects Exhibiting Clinical Improvement in Symptoms | Clinical Improvement |
|---|---|---|---|---|---|
| facial flushing (Hot Flashes) | 9 | 6 drops per ear 1x/day 4% lidocaine; 2% Bupivacaine | at least 2 weeks | 10 | |
| facial blushing | 9 | 6 drops per ear 1x/day 4% lidocaine; 2% Bupivacaine | at least 2 weeks | 10 | |
| Alopecia Areata | 4 | 6 drops per ear 1x/day 4% lidocaine; 2% Bupivacaine | at least 2 weeks | 4 | |
| Atopic Dematitis | 2 | 6 drops per ear 1x/day 4% lidocaine; 2% Bupivacaine | at least 2 weeks | 2 | |
| Chronic Eczema | 2 | 6 drops per ear 1x/day 4% lidocaine; 2% Bupivacaine | at least 2 weeks | 2 | |
| Acne Vulgaris | 3 | 6 drops per ear 1x/day 4% lidocaine; 2% Bupivacaine | at least 2 weeks | 3 | |
| Oily Skin | 3 | 6 drops per ear 1x/day 4% lidocaine; 2% Bupivacaine | at least 2 weeks | 3 | |
| Rosacea | 2 | 6 drops per ear 1x/day 4% lidocaine; 2% Bupivacaine | at least 2 weeks | 2 | |
| Morgellons Disease | | 6 drops per ear 1x/day 4% lidocaine; 2% Bupivacaine | at least 2 weeks | | |

TABLE 14

Clinical Experiment with Neuropology-Psychiatry-related affliction

| Neurology-Psychiatry-related affliction | # of Subjects Treated | Tmt Protocol (XYZ) | Tmt Time | # of Subjects Exhibiting Clinical Improvement in Symptoms | Clinical Improvement |
|---|---|---|---|---|---|
| Reflex Sympathetic Dystrophy | 20 | 6 drops per ear 1x/day 4% lidocaine; 2% Bupivacaine | at least 2 weeks | 20 | |
| Sensory Processing Disorder | 1 | 6 drops per ear 1x/day 4% lidocaine; 2% Bupivacaine | at least 2 weeks | 1 | |
| Decreased Libido | 2 | 6 drops per ear 1x/day 4% lidocaine; 2% Bupivacaine | at least 2 weeks | 1 | |

TABLE 15

Clinical Experiment with Cell Proliferation-related afflictions

| Cell Proliferation-related afflictions | # of Subjects Treated | Tmt Protocol (XYZ) | Tmt Time | # of Subjects Exhibiting Clinical Improvement in Symptoms | Clinical Improvement |
|---|---|---|---|---|---|
| Cancer | 3 | 6 drops per ear 1x/day 4% lidocaine; 2% Bupivacaine | at least 2 weeks | 3 | Modulation of theSympathetic Nervous System and the prevention and spread of prostate cancer, lymphoblastic leukemia, ovarian cancer, breast cancer Prevention of side effects to chemotherapy (Side effects such as pain, fatigue, anxiety, and sympathetic nervous system overstimulation) |
| Mastocytosis | 1 | 6 drops per ear 1x/day 4% lidocaine; 2% Bupivacaine | at least 2 weeks | 1 | |

TABLE 16

Clinical Experiment with Blood Flow-related afflictions

| Blood Flow-related afflictions | # of Subjects Treated | Tmt Protocol (XYZ) | Tmt Time | # of Subjects Exhibiting Clinical Improvement in Symptoms | Clinical Improvement |
|---|---|---|---|---|---|
| Erectile Dysfunction | 1 | 6 drops per ear 1x/day 4% lidocaine; 2% Bupivacaine | at least 2 weeks | 1 | |
| Open Wound Healing | 1 | 6 drops per ear 1x/day 4% lidocaine; 2% Bupivacaine | at least 2 weeks | 1 | Increase in peripheral blood flow |
| Sickle Cell Disease | 1 | 6 drops per ear 1x/day 4% lidocaine; 2% Bupivacaine | at least 2 weeks | 1 | |

Example 12—Treatment of Pain

Embodiments of the invention further comprise treating pain, such as pain that results from a variety of diseases disclosed herein, by performing auricular anesthesia that indirectly anesthetizes paraspinal and paravertebral ganglion. Those respective ganglion receive general visceral afferent signals that are thus modulated. Those modulated signals travel from the paraspinal and paravertebral ganglion to the dorsal root ganglion, then to the dorsal grey horn of the spinal cord, where they meet with general somatic afferent signals. Modulated general visceral afferent signals modulate the general somatic afferent signals by this invention, thus modulates pain in both nervous system pathways.

Embodiments of the invention comprise methods of blocking pain from a variety of diseases that comprises performing auricular anesthesia of the ear canal and concha, resulting in anesthesia to branches of cervical nerves 2 and 3 (C2, C3) and cranial nerves 5, 7, 9, and 10. The tenth cranial nerve, or Vagus Nerve, has direct attachments to the eleventh (11) and twelfth (12) cranial nerves and the sympathetic ganglion.

As is known in the art, pain is typically treated by administering an anesthetic or analgesic directly to the site of the pain. For example, U.S. Pat. No. 6,093,417 (Petrus) teaches administration of a topical ear composition comprising a penetration enhancer directly to the ear itself for the purpose of reducing inflammation of the inner ear and providing pain relief of the inner ear. However, as described herein, the invention provided for a method for ameliorating pain in a subject comprising administering to the ear canal of a subject a pain relieving composition so as to ameliorate pain at a distal site (i.e, non-ear pain, away from the site of composition administration).

A test of an embodiment of the method described herein was conducted to evaluate the efficacy of the method for treating patients suffering from pain. Subjects suffering from pain were instructed to utilize drops of a pharmaceutical composition comprising antipyrine ($\approx 54.0$ mg) and benzocaine ($\approx 14.0$ mg) (treatment protocol, "AB" Tmt Protocol) or drops of a pharmaceutical composition comprising lidocaine ($\approx 40.0$ mg) and tetracaine ($\approx 5.0$ mg) (treatment protocol, "LAT" Tmt Protocol), in one or both ears, at least one time per day (for example, either in the morning or at night), for a period of time as needed (Tmt Time). The LAT otic solution used in the tests comprises 4% Lidocaine, 0.5% Tetracaine, 1/100,000 Epinephrine, and Anhydrous Glycerine. The AB otic solution used in the tests comprises 5.4% Antipyrine, 1.4% Benzocaine, Oxyquinoline Sulfate, and Anhydrous Glycerine.

TABLE 17

Clinical Experiment with Pain-related afflictions

| Pain-related afflictions | # of Subjects Treated | Tmt Protocol (XYZ) | Tmt Time | # of Subjects Exhibiting Clinical Improvement in Symptoms | Clinical Improvement |
|---|---|---|---|---|---|
| Post-Tonsillectomy Pharyngeal or Oropharyngeal Pain | 500 | 6 drops per ear 3 times per day | For 10 days post operation | 495 | |
| Post-Adenoidectomy Pharyngeal or Oropharyngeal Pain | 200 | 6 drops per ear 2 times per day | For 7 days post operation | 200 | |
| Laryngeal Pain | 2 | 6 drops per ear once a day | As needed | 2 | |
| Migraine Pain | 5 | LAT: 6 drops per ear 1x/day | 4 wks | 4 | ≥70% reduction in migraine headaches per month (frequency, duration, and intensity) |
| | 3 | AB: 6 drops per ear 1x/day | 4 wks | 2 | —w/both tmts |
| Anxiety Headaches | 5 | LAT: 6 drops per ear 1x/day | 4 wks | 5 | ≥75% reduction in headaches per month (frequency, duration, and intensity) |

TABLE 17-continued

Clinical Experiment with Pain-related afflictions

| Pain-related afflictions | # of Subjects Treated | Tmt Protocol (XYZ) | Tmt Time | # of Subjects Exhibiting Clinical Improvement in Symptoms | Clinical Improvement |
|---|---|---|---|---|---|
| | 5 | AB: 6 drops per ear 1x/day | 4 wks | 2 | —w/both tmts |
| Peripheral Neuropathy | 5 | LAT: 6 drops per ear 1x/day | 4 wks | 4 | ≥50% reduction in peripheral pain |
| | 5 | AB: 6 drops per ear 1x/day | 4 wks | 4 | —w/both tmts |
| Neck and Shoulder Pain | 5 | LAT: 6 drops per ear 1x/day | 4 wks | 5 | ≥50% reduction in pain |
| | 3 | AB: 6 drops per ear 1x/day | 4 wks | 2 | —w/both tmts |
| General Somatic Afferent Pain— Neuromuscular Pain | 4 | LAT: 6 drops per ear 1x/day | 4 wks | 3 | less neck, back, arm, leg, shoulder, and chest pain |
| | 2 | AB: 6 drops per ear 1x/day | 4 wks | 1 | —w/both tmts |
| General Somatic Afferent Pain—Joint Pain (nonspecific) | 4 | LAT: 6 drops per ear 1x/day | 4 wks | 3 | ≥50% reduction in pain requiring less pain medications |
| | 3 | AB: 6 drops per ear 1x/day | 4 wks | 2 | —w/both tmts |
| General Somatic Afferent Pain— Sciatica pain | 4 | LAT: 6 drops per ear 1x/day | 4 wks | 3 | reduction in pain |
| General Somatic Afferent Pain— Arthritis pain | 4 | LAT: 6 drops per ear 1x/day | 4 wks | 3 | reduction in pain |
| General Somatic Afferent Pain— Shingles Pain | 4 | LAT: 6 drops per ear 1x/day | 4 wks | 3 | reduction in pain |
| General Somatic Afferent Pain— Reflex Sympathetic Dystrophy pain | 3 | LAT: 6 drops per ear 1x/day | 4 wks | 3 | ≥70% reduction in peripheral pain signals less electrical, sharp pain |
| | 1 | AB: 6 drops per ear 1x/day | 4 wks | 1 | —w/both tmts |
| General Visceral Afferent Pain | 5 | LAT: 6 drops per ear 1x/day | 4 wks | 4 | ≥70% reduction in esophageal, stomach, intestinal, bladder, and pelvic pain |
| | 1 | AB: 6 drops per ear 1x/day | 4 wks | 1 | —w/both tmts |
| Post Tonsillectomy Pain | 50 | LAT: 6 drops per ear 1x/day | 4 wks | 50 | ≥50% reduction in pain Reduction of pain medications |
| | 50 | AB: 6 drops per ear 1x/day | 4 wks | 50 | —w/both tmts |

TABLE 17-continued

Clinical Experiment with Pain-related afflictions

| Pain-related afflictions | # of Subjects Treated | Tmt Protocol (XYZ) | Tmt Time | # of Subjects Exhibiting Clinical Improvement in Symptoms | Clinical Improvement |
|---|---|---|---|---|---|
| Pharyngeal Pain | 50 | LAT: 6 drops per ear 1x/day | 4 wks | 50 | ≥70% reduction in throat pain |
| | 50 | AB: 6 drops per ear 1x/day | 4 wks | 50 | —w/both tmts |
| Laryngeal Pain | 5 | LAT: 6 drops per ear 1x/day | 4 wks | 5 | ≥50% reduction in laryngeal pain |
| | 5 | AB: 6 drops per ear 1x/day | 4 wks | 5 | —w/both tmts |
| Ear Pain (acute and chronic) | 5 | LAT: 6 drops per ear 1x/day | 4 wks | 2 | 70% less ear pain |
| | 8 | AB: 6 drops per ear 1x/day | 4 wks | 5 | —w/both tmts |
| Neck Pain | 3 | LAT: 6 drops per ear 1x/day | 4 wks | 2 | 50% less neck pain |
| | 3 | AB: 6 drops per ear 1x/day | 4 wks | 2 | —w/both tmts |
| Trigeminal Neuralgia Pain | 5 | LAT: 6 drops per ear 1x/day | 4 wks | 4 | 50% less facial pain |
| | 3 | AB: 6 drops per ear 1x/day | 4 wks | 2 | —w/both tmts |
| Temporomandibular Joint Pain | 5 | LAT: 6 drops per ear 1x/day | 4 wks | 4 | ≥70% reduction of jaw pain |
| | 3 | AB: 6 drops per ear 1x/day | 4 wks | 2 | —w/both tmts |
| Pelvic Pain | 5 | LAT: 6 drops per ear 1x/day | 4 wks | 5 | ≥50% reduction of pelvic pain from infection, surgery or ovaries, and fibroids |
| | 3 | AB: 6 drops per ear 1x/day | 4 wks | 2 | —w/both tmts |
| Chronic Prostatitis Pain | 1 | LAT: 6 drops per ear 1x/day | 4 wks | 1 | ≥50% reduction in pain and pressure |
| | 1 | AB: 6 drops per ear 1x/day | 4 wks | 1 | —w/both tmts |
| Cystitis Pain | 5 | LAT: 6 drops per ear 1x/day | 4 wks | 5 | ≥50% reduction in pain |
| | 1 | AB: 6 drops per ear 1x/day | 4 wks | 1 | —w/both tmts |

TABLE 17-continued

Clinical Experiment with Pain-related afflictions

| Pain-related afflictions | # of Subjects Treated | Tmt Protocol (XYZ) | Tmt Time | # of Subjects Exhibiting Clinical Improvement in Symptoms | Clinical Improvement |
|---|---|---|---|---|---|
| Kidney Pain (from stone, infection, tumor) | 2 | LAT: 6 drops per ear 1x/day | 4 wks | 2 | ≥50% reduction in pain from stone, infection, tumor, etc |
| | 1 | AB: 6 drops per ear 1x/day | 4 wks | 1 | —w/both tmts |
| Gastritis Pain | 5 | LAT: 6 drops per ear 1x/day | 4 wks | 5 | ≥50% reduction in stomach pain and burning |
| | 3 | AB: 6 drops per ear 1x/day | 4 wks | 2 | —w/both treatments |
| Gall Bladder Pain | 2 | LAT: 6 drops per ear 1x/day | 4 wks | 2 | ≥50% reduction in pain |
| | 2 | AB: 6 drops per ear 1x/day | 4 wks | 2 | —w/both treatments |
| Pancreatitis pain | 4 | LAT: 6 drops per ear 1x/day | 4 wks | 3 | ≥50% reduction in abdominal pain |
| | 2 | AB: 6 drops per ear 1x/day | 4 wks | 1 | —w/both treatments |

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method for symptomatic relief of a subject suffering from an affliction associated with a particular cranial nerve, wherein the particular cranial nerve is the trigeminal nerve, the facial nerve, the glossopharyngeal nerve, the accessory nerve, the hypoglossal nerve, the vagus nerve, or a combination thereof, the method comprising administering to an ear canal of a subject an effective amount of a pharmaceutical composition consisting of at least one anesthetic of Formula I:

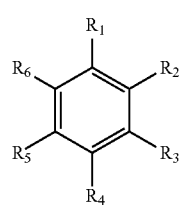

wherein $R_1$ is:

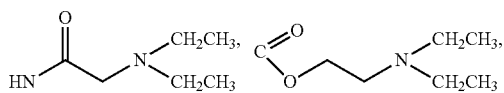

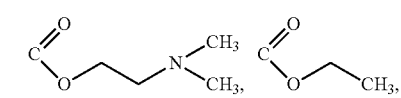

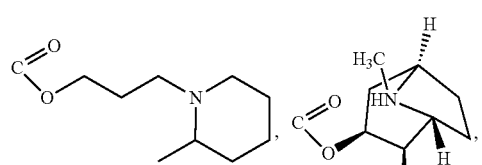

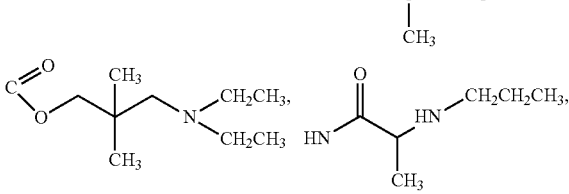

-continued

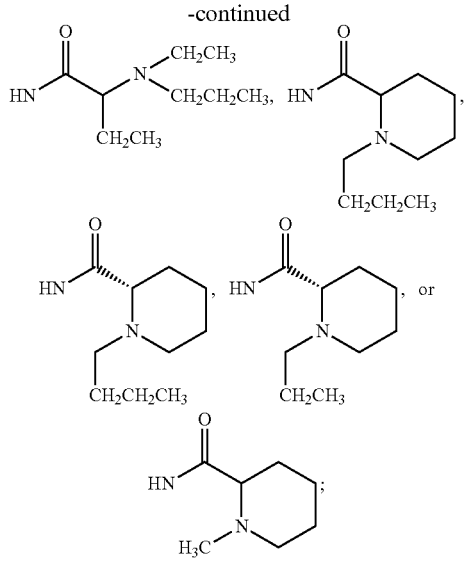

wherein $R_2$ is H, $CH_3$, Cl, or

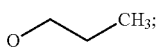

wherein $R_3$ is H or $NH_2$;
wherein $R_4$ is H, $NH_2$, $CH_3$,

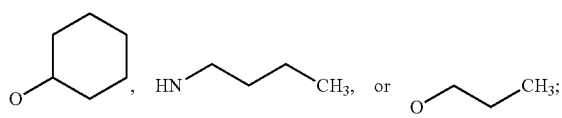

wherein $R_5$ is H; and wherein $R_6$ is H or $CH_3$
wherein the affliction is a neurology-psychiatry-related affliction, ear-nose-throat (ENT)-related affliction, Gastroenterology/Urology (GU)-related affliction, gastrointestinal (GI)-related affliction, cardiac-related affliction, pulmonary-related affliction, metabolic-related affliction, infection-related affliction, skin-related affliction, cell proliferation-related affliction, or blood flow-related affliction;
wherein the neurology-psychiatry-related affliction is at least one selected from the group consisting of: chronic fatigue syndrome, fibromyalgia, epilepsy, Obsessive Compulsive Disorder, panic attack, Post-Traumatic Stress Disorder, Tourette's Syndrome, Focal Dystonia, Tic Doloreaux, Bulimia, Anxiety, Depression, Restless Leg Syndrome, Dysautonomia, Familial Intentional Tremor, Migraine pain, Autism Spectrum Disorder, Anxiety Headache, sleeplessness, Reticular Activating System (RAS) dysregulation, Multiple Sclerosis, Peripheral Neuropathy, Apraxia, Neck and Shoulder Pain, Parkinson's Disease, General Somatic Afferent Pain, General Visceral, Afferent Pain, opiate withdrawal, Dysarthria, ADHD, Nonspecific hand tremor, Stuttering, cerebral palsy, Raynaud's Phenomenon, excessive sweating, reflex sympathetic dystrophy, sensory processing disorder, and decreased libido;
wherein the ear-nose-throat (ENT)-related affliction is at least one selected from the group consisting of: Palatal Myoclonus, Post Tonsillectomy Pain, Pharyngeal Pain, Laryngeal Pain, Neurogenic Cough, Globus Hystericus, Spasmodic Dysphonia, Snoring, Allergic Rhinitis, Chronic Sinusitis, Chronic Nasal Congestion, Allergic Conjunctivitis, Sneezing, Hiccups, Rhinitis, Dysphagia, neck pain, Dry Eye Syndrome, Trigeminal Neuralgia pain, and Temporomandibular Joint Pain;
wherein the Gastroenterology/Urology (GU)-related affliction is at least one selected from the group consisting of: bladder spasm, dysmenorrhea, pelvic pain, Premature Labor, interstitial cystitis, Prostatitis, Eclampsia, pre-eclampsia, HELLP Syndrome, cystitis, Kidney Pain, enuresis, dysuria, dyspareunia, encopresis, heavy flow menstruation, frequent urination, Prolonged Vaginal Bleeding, decreased renal blood flow, chronic renal failure;
wherein the gastrointestinal (GI)-related affliction is at least one selected from the group consisting of: irritable bowel syndrome (IBS), ulcerative colitis, acid reflux, Gastritis, Gastroenteritis, Hyperemesis Gravidarum, Pediatric Colic, Hepato-Renal Syndrome, Appetite Suppression, Gall Bladder Pain, Chronic constipation, Chronic diarrhea, and Pancreatitis;
wherein the cardiac-related affliction is at least one selected from the group consisting of: Paroxysmal (Lone) (Vagal) Atrial Fibrillation, Orthostatic (Neurogenic) Hypotension, Reflex Asystolic Syncope, Postural Orthostatic Tachycardia Syndrome (POTS), Vasovagal Reflex, cardiac surgery derived cough, heart block, Atrial Contractions, Tachycardia, Congestive Heart Failure, premature atrial contraction, and atrial tachycardia;
wherein the pulmonary-related affliction is at least one selected from the group consisting of: asthma, chronic obstructive pulmonary disease (COPD), bronchitis, cystic fibrosis, and Bronchospasm;
wherein the metabolic-related affliction is at least one selected from the group consisting of: hypertension, diabetes, septic shock, neurogenic shock, hyperglycemia, hypercholesteremia, and insulin resistance;
wherein the infection-related affliction is at least one selected from the group consisting of: Herpes Simplex 1 infection, Herpes, Simplex 2 infection, and Varicella Zoster infection;
wherein the skin-related affliction is at least one selected from the group consisting of: facial flushing, facial blushing, alopecia areata, atopic dermatitis, chronic eczema, acne vulgaris, oily skin, rosacea, and morgellons disease;
wherein the cell proliferation-related affliction is at least one selected from the group consisting of prostate cancer, lymphoblastic leukemia, ovarian cancer, breast cancer and mastocytosis; and
wherein the blood flow-related affliction is at least one selected from the group consisting of erectile dysfunction, open wound healing, and sickle cell disease; and
wherein the subject does not have an ear infection or ear pain;
wherein the pharmaceutical composition does not comprise an analgesic.

2. The method of claim 1, wherein the pharmaceutical composition further comprises one or more of a pharmaceutically acceptable carrier, an antibiotic, a vasoconstrictor, glycerin, epinephrine, or acetic acid.

3. The method of claim 1, wherein the anesthetic is benzocaine, chloroprocaine, cocaine, cyclomethycaine, dimethocaine, larocaine, piperocaine, propoxycaine, procaine, novocaine, proparacaine, tetracaine, amethocaine, articaine, bupivacaine, cinchocaine, dibucaine, etidocaine, levobupivacaine, lidocaine, lignocaine, mepivacaine, prilocaine, ropivacaine, farmocaine, trimecaine, or a combination of the anesthetics listed herein.

* * * * *